United States Patent
Zeitlin et al.

(10) Patent No.: US 10,104,880 B2
(45) Date of Patent: Oct. 23, 2018

(54) CELL COMPOSITION AND METHODS OF MAKING THE SAME

(75) Inventors: Andy Zeitlin, Basking Ridge, NJ (US); Gregory Russotti, Stirling, NJ (US); Shuyang He, Martinsville, NJ (US); Ajai Pal, Bridgewater, NJ (US); Hong J. Chen, Warren, NJ (US); Thomas Brieva, Manalapan, NJ (US); Ryan Shorr, Monroe, NY (US); Brian Murphy, New Jersey, NJ (US)

(73) Assignee: CELULARITY, INC., Warren, NJ (US)

(*) Notice: Subject to any disclaimer, the term of this patent is extended or adjusted under 35 U.S.C. 154(b) by 390 days.

(21) Appl. No.: 12/544,949

(22) Filed: Aug. 20, 2009

(65) Prior Publication Data

US 2010/0047213 A1 Feb. 25, 2010

Related U.S. Application Data

(60) Provisional application No. 61/090,577, filed on Aug. 20, 2008.

(51) Int. Cl.
| | |
|---|---|
| *A61K 35/12* | (2015.01) |
| *C12N 5/02* | (2006.01) |
| *C12N 5/071* | (2010.01) |
| *A01N 1/02* | (2006.01) |

(52) U.S. Cl.
CPC .................................. *A01N 1/0221* (2013.01)

(58) Field of Classification Search
None
See application file for complete search history.

(56) References Cited

U.S. PATENT DOCUMENTS

| | | | |
|---|---|---|---|
| 3,862,002 | A | 1/1975 | Sanders |
| 4,798,824 | A | 1/1989 | Belzer et al. |
| 4,829,000 | A | 5/1989 | Kleinman et al. |
| 5,004,681 | A | 4/1991 | Boyse et al. |
| 5,192,553 | A | 3/1993 | Boyse et al. |
| 5,197,985 | A | 3/1993 | Caplan et al. |
| 5,226,914 | A | 7/1993 | Caplan et al. |
| 5,272,071 | A | 12/1993 | Chappel |
| 5,284,766 | A | 2/1994 | Okano et al. |
| 5,364,756 | A * | 11/1994 | Livesey et al. ................... 435/2 |
| 5,372,581 | A | 12/1994 | Anderson |
| 5,385,901 | A | 1/1995 | Kaplan |
| 5,415,665 | A | 5/1995 | Hessel et al. |

(Continued)

FOREIGN PATENT DOCUMENTS

| | | |
|---|---|---|
| CN | 1407088 | 4/2003 |
| CN | 1548529 | 11/2004 |

(Continued)

OTHER PUBLICATIONS

Fuller, Barry J.; Grout, Brian W. W.; Clinical Applicantions of Cryobiology. 1st Edition, CRC Press, 1991.*

(Continued)

*Primary Examiner* — David W Berke-Schlessel
(74) *Attorney, Agent, or Firm* — Timothy L. Smith; Geoffry T. Knudsen

(57) ABSTRACT

Provided herein are improved methods for the formulation of compositions comprising placental stem cells, and improved compositions and cell formulations produced thereby.

22 Claims, 29 Drawing Sheets

(56) References Cited

U.S. PATENT DOCUMENTS

Figure 1:
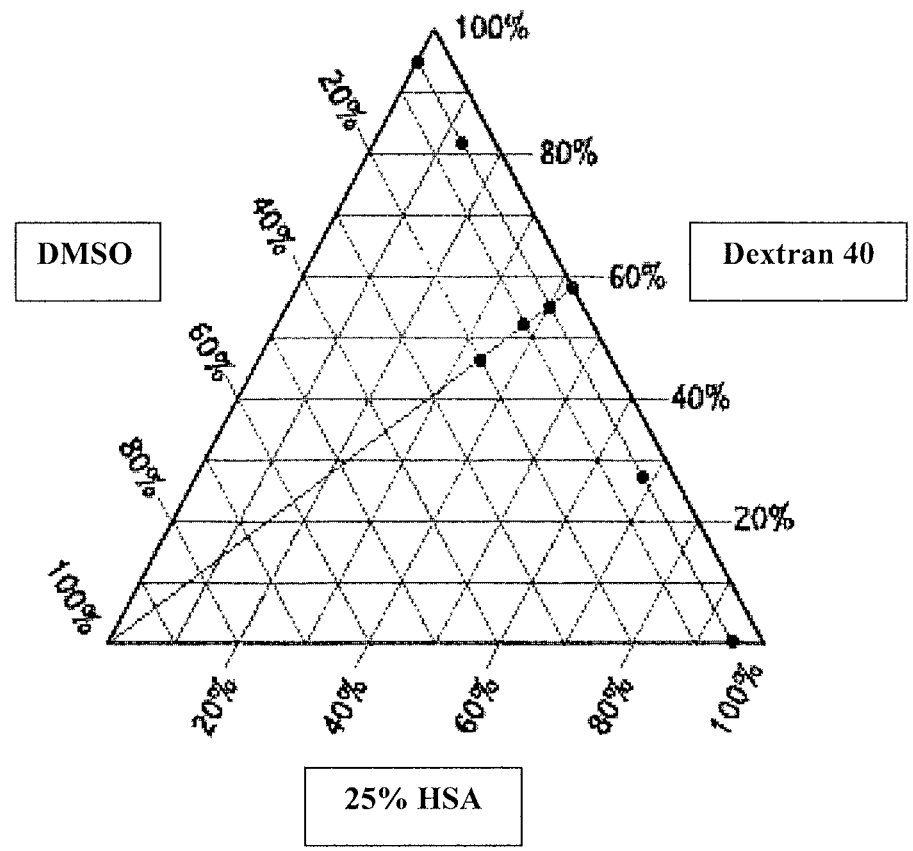

| | | |
|---|---|---|
| 5,436,151 A | 7/1995 | McGlave et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,580,777 A | 12/1996 | Bernard |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,846,807 A | 12/1998 | Goodwin |
| 5,849,553 A | 12/1998 | Anderson et al. |
| 5,855,619 A | 1/1999 | Caplan et al. |
| 5,858,782 A | 1/1999 | Long et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Varfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,820 A | 10/1999 | Zborowski et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakamam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,467,630 B1 | 10/2002 | Zborowski et al. |
| 6,497,875 B1 | 12/2002 | Sorrell et al. |
| 6,534,084 B1 | 3/2003 | Vyakamam et al. |
| 6,541,024 B1 | 4/2003 | Kadiyala et al. |
| 6,645,731 B2 | 11/2003 | Terstappen et al. |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,878,543 B1 | 4/2005 | Wahlberg et al. |
| 6,911,201 B1 | 6/2005 | Merchav et al. |
| 6,916,655 B2 | 7/2005 | Yasumoto |
| 7,015,037 B1 | 3/2006 | Furcht et al. |
| 7,029,666 B2 | 4/2006 | Bruder et al. |
| 7,045,148 B2 | 5/2006 | Hariri |
| 7,101,710 B2 | 9/2006 | Tsai et al. |
| 7,122,178 B1 | 10/2006 | Simmons et al. |
| 7,147,626 B2 | 12/2006 | Goodman et al. |
| 7,153,500 B2 | 12/2006 | Qasba et al. |
| 7,244,759 B2 | 7/2007 | Muller et al. |
| 7,255,729 B2 | 8/2007 | Yamada et al. |
| 7,255,879 B2 | 8/2007 | Hariri |
| 7,282,222 B2 | 10/2007 | Phillips |
| 7,311,904 B2 | 12/2007 | Hariri |
| 7,311,905 B2 | 12/2007 | Hariri |
| 7,399,632 B2 | 7/2008 | Simmons et al. |
| 7,413,734 B2 | 8/2008 | Mistry et al. |
| 7,422,736 B2 | 9/2008 | Hwang |
| 7,468,276 B2 | 12/2008 | Hariri |
| 7,498,171 B2 | 3/2009 | Hariri et al. |

(56) References Cited

U.S. PATENT DOCUMENTS

| | | | |
|---|---|---|---|
| 7,510,873 B2 | 3/2009 | Mistry et al. | |
| 7,514,074 B2 | 4/2009 | Pittenger et al. | |
| 7,524,489 B2 | 4/2009 | Messina et al. | |
| 7,534,606 B2 | 5/2009 | Chen et al. | |
| 7,534,609 B2 | 5/2009 | Merchav et al. | |
| 7,560,276 B2 | 7/2009 | Harmon et al. | |
| 7,569,385 B2 | 8/2009 | Haas | |
| 7,615,374 B2 | 11/2009 | Vodyanyk et al. | |
| 7,635,591 B2 | 12/2009 | Kim et al. | |
| 7,638,141 B2 | 12/2009 | Hariri et al. | |
| 7,659,118 B2 | 2/2010 | Furcht et al. | |
| 7,682,803 B2 | 3/2010 | Paludan et al. | |
| 7,700,090 B2 | 4/2010 | Heidaran et al. | |
| 7,909,806 B2 | 3/2011 | Goodman et al. | |
| 7,914,779 B2 | 3/2011 | Hariri | |
| 7,928,280 B2 | 4/2011 | Hariri et al. | |
| 7,976,836 B2 | 7/2011 | Hariri | |
| 7,993,918 B2 | 8/2011 | Paludan et al. | |
| 8,057,788 B2 * | 11/2011 | Hariri | 424/93.1 |
| 8,057,789 B2 | 11/2011 | Hariri | |
| 8,062,837 B2 * | 11/2011 | Chow | A61K 35/28 435/2 |
| 8,071,135 B2 | 12/2011 | Liu et al. | |
| 8,071,376 B2 | 12/2011 | Heidaran | |
| 8,105,634 B2 | 1/2012 | Liu et al. | |
| 2001/0005591 A1 | 6/2001 | Qasba et al. | |
| 2001/0038836 A1 | 11/2001 | During et al. | |
| 2002/0102239 A1 | 8/2002 | Koopmans | |
| 2002/0123141 A1 | 9/2002 | Hariri | |
| 2002/0132343 A1 | 9/2002 | Lum | |
| 2002/0160510 A1 | 10/2002 | Hariri | |
| 2003/0007954 A1 | 1/2003 | Naughton et al. | |
| 2003/0032179 A1 | 2/2003 | Hariri | |
| 2003/0036193 A1 | 2/2003 | Fallon et al. | |
| 2003/0044977 A1 | 3/2003 | Sakuragawa et al. | |
| 2003/0045552 A1 | 3/2003 | Robarge et al. | |
| 2003/0059414 A1 | 3/2003 | Ho et al. | |
| 2003/0235563 A1 | 4/2003 | Strom et al. | |
| 2003/0096841 A1 | 5/2003 | Robarge et al. | |
| 2003/0161818 A1 | 8/2003 | Weiss et al. | |
| 2003/0180269 A1 | 9/2003 | Hariri | |
| 2003/0187515 A1 | 10/2003 | Hariri et al. | |
| 2003/0235909 A1 | 12/2003 | Hariri | |
| 2004/0018617 A1 | 1/2004 | Hwang | |
| 2004/0028660 A1 | 2/2004 | Hariri et al. | |
| 2004/0033214 A1 | 2/2004 | Young et al. | |
| 2004/0048372 A1 | 3/2004 | Hariri | |
| 2004/0048796 A1 | 3/2004 | Hariri et al. | |
| 2004/0058412 A1 | 3/2004 | Ho et al. | |
| 2004/0107453 A1 | 6/2004 | Furcht et al. | |
| 2004/0161419 A1 | 6/2004 | Strom et al. | |
| 2004/0136967 A1 | 7/2004 | Weiss et al. | |
| 2004/0171147 A1 | 9/2004 | Hariri | |
| 2004/0180040 A1 | 9/2004 | Phillips et al. | |
| 2004/0219136 A1 | 11/2004 | Hariri | |
| 2004/0229351 A1 | 11/2004 | Rodriguez et al. | |
| 2004/0241144 A1 | 12/2004 | Kaps et al. | |
| 2005/0019865 A1 | 1/2005 | Kihm et al. | |
| 2005/0019908 A1 | 1/2005 | Hariri | |
| 2005/0019911 A1 | 1/2005 | Gronthos et al. | |
| 2005/0032209 A1 | 2/2005 | Messina et al. | |
| 2005/0037491 A1 | 2/2005 | Mistry et al. | |
| 2005/0042595 A1 | 2/2005 | Haas | |
| 2005/0054093 A1 | 3/2005 | Haas | |
| 2005/0054098 A1 | 3/2005 | Mistry et al. | |
| 2005/0058629 A1 | 3/2005 | Harmon et al. | |
| 2005/0058630 A1 | 3/2005 | Harris et al. | |
| 2005/0058631 A1 | 3/2005 | Kihm et al. | |
| 2005/0085543 A1 | 4/2005 | Wallimann et al. | |
| 2005/0089513 A1 | 4/2005 | Sakuragawa et al. | |
| 2005/0112104 A1 | 5/2005 | Pittenger et al. | |
| 2005/0118147 A1 | 6/2005 | Oh | |
| 2005/0118712 A1 | 6/2005 | Tsai et al. | |
| 2005/0118715 A1 | 6/2005 | Hariri et al. | |
| 2005/0124003 A1 | 6/2005 | Atala et al. | |
| 2005/0143420 A1 | 6/2005 | Moutouh-de Parseval et al. |
| 2005/0148034 A1 | 6/2005 | Hariri et al. |
| 2005/0148074 A1 | 7/2005 | Davies et al. |
| 2005/0158289 A1 | 7/2005 | Simmons et al. |
| 2005/0169896 A1 | 8/2005 | Li et al. |
| 2005/0176139 A1 | 8/2005 | Chen et al. |
| 2005/0181502 A1 | 8/2005 | Furcht et al. |
| 2005/0181504 A1 | 8/2005 | Merchav et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0249708 A1 | 11/2005 | Garbuzova-Davis et al. |
| 2005/0255588 A1 | 11/2005 | Young et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0030041 A1 | 2/2006 | Furcht et al. |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 7/2006 | Seyda et al. |
| 2006/0177924 A1 | 8/2006 | Rezania et al. |
| 2006/0182724 A1 | 8/2006 | Riordan |
| 2006/0188983 A1 | 8/2006 | Harris et al. |
| 2006/0210544 A1 | 9/2006 | Osamu et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0003530 A1 | 1/2007 | Pittenger et al. |
| 2007/0009494 A1 | 1/2007 | Mistry et al. |
| 2007/0010011 A1 | 1/2007 | Parsons et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0065938 A1 | 3/2007 | Gronthos et al. |
| 2007/0122903 A1 | 3/2007 | Rezania et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0116683 A1 | 5/2007 | Atala et al. |
| 2007/0116684 A1 | 5/2007 | Atala et al. |
| 2007/0122902 A1 | 5/2007 | Lee et al. |
| 2007/0128174 A1 | 6/2007 | Kleinsek et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0172465 A1 | 7/2007 | Low et al. |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0231297 A1 | 10/2007 | Smith et al. |
| 2007/0231309 A1 | 10/2007 | Ho et al. |
| 2007/0237751 A1 | 10/2007 | Sanberg et al. |
| 2007/0243172 A1 | 10/2007 | Ra et al. |
| 2007/0253931 A1 | 11/2007 | Varney et al. |
| 2007/0258963 A1 | 11/2007 | Danilkovitch et al. |
| 2007/0264269 A1 | 11/2007 | Harmon et al. |
| 2007/0275362 A1 | 11/2007 | Edinger et al. |
| 2007/0287176 A1 | 12/2007 | Rezania |

(56) References Cited

U.S. PATENT DOCUMENTS

| | | | |
|---|---|---|---|
| 2007/0292398 A1* | 12/2007 | Collins | C12N 5/0607 424/93.7 |
| 2007/0292399 A1 | 12/2007 | Heidaran et al. | |
| 2007/0292910 A1 | 12/2007 | Heidaran et al. | |
| 2008/0032401 A1 | 2/2008 | Edinger et al. | |
| 2008/0044392 A1 | 2/2008 | Kues et al. | |
| 2008/0044848 A1 | 2/2008 | Heidaran | |
| 2008/0050347 A1 | 2/2008 | Ichim | |
| 2008/0050814 A1 | 2/2008 | Allickson | |
| 2008/0064098 A1* | 3/2008 | Allickson | C12N 5/0605 435/366 |
| 2008/0069895 A1 | 3/2008 | Liu et al. | |
| 2008/0095749 A1 | 4/2008 | Aggarwal et al. | |
| 2008/0159998 A1 | 4/2008 | Ichim | |
| 2008/0102506 A1 | 5/2008 | Teplyashin | |
| 2008/0118477 A1 | 5/2008 | Christopherson | |
| 2008/0131405 A1 | 6/2008 | Jeun | |
| 2008/0131409 A1 | 6/2008 | Cataldo et al. | |
| 2008/0131410 A1 | 6/2008 | Hariri | |
| 2008/0131522 A1 | 6/2008 | Liu et al. | |
| 2008/0131966 A1 | 6/2008 | Hariri | |
| 2008/0145934 A1 | 6/2008 | Harris et al. | |
| 2008/0152624 A1 | 6/2008 | Paludan et al. | |
| 2008/0152629 A1 | 6/2008 | Edinger et al. | |
| 2008/0166328 A1 | 7/2008 | Harmon et al. | |
| 2008/0171019 A1 | 7/2008 | Michejda | |
| 2008/0171384 A1 | 7/2008 | Dzierzak et al. | |
| 2008/0175824 A1 | 7/2008 | Heidaran et al. | |
| 2008/0175829 A1 | 7/2008 | Cheng et al. | |
| 2008/0181935 A1 | 7/2008 | Bhatia et al. | |
| 2008/0181967 A1 | 7/2008 | Liu et al. | |
| 2008/0206343 A1 | 8/2008 | Edinger et al. | |
| 2008/0208158 A1 | 8/2008 | Goodman et al. | |
| 2008/0213227 A1 | 9/2008 | Aggarwal et al. | |
| 2008/0213228 A1 | 9/2008 | Edinger et al. | |
| 2008/0226595 A1 | 9/2008 | Edinger et al. | |
| 2008/0226612 A1 | 9/2008 | Treves et al. | |
| 2008/0241171 A1 | 10/2008 | Gentry et al. | |
| 2008/0248005 A1 | 10/2008 | Phan | |
| 2008/0254005 A1 | 10/2008 | Riordan et al. | |
| 2008/0254538 A1 | 10/2008 | Messina et al. | |
| 2008/0260694 A1 | 10/2008 | Gronthos et al. | |
| 2008/0260703 A1 | 10/2008 | Riordan et al. | |
| 2008/0260704 A1 | 10/2008 | Riordan et al. | |
| 2008/0274087 A1 | 11/2008 | Li et al. | |
| 2008/0279956 A1 | 11/2008 | Lin | |
| 2008/0286249 A1 | 11/2008 | Varney et al. | |
| 2008/0286267 A1 | 11/2008 | Sing et al. | |
| 2008/0292597 A1 | 11/2008 | Steenblock | |
| 2008/0292600 A1 | 11/2008 | Song et al. | |
| 2008/0292601 A1 | 11/2008 | Song | |
| 2008/0299090 A1 | 12/2008 | Weiss et al. | |
| 2008/0305148 A1 | 12/2008 | Fu | |
| 2008/0311087 A1 | 12/2008 | Gosiewska et al. | |
| 2008/0311088 A1 | 12/2008 | Chang et al. | |
| 2009/0004738 A1 | 1/2009 | Merchav et al. | |
| 2009/0016999 A1 | 1/2009 | Cohen et al. | |
| 2009/0053182 A1 | 2/2009 | Ichim et al. | |
| 2009/0053805 A1 | 2/2009 | Hariri | |
| 2009/0060885 A1 | 3/2009 | Ha et al. | |
| 2009/0068155 A1 | 3/2009 | Frey et al. | |
| 2009/0074728 A1 | 3/2009 | Gronthos et al. | |
| 2009/0074731 A1 | 3/2009 | Librach et al. | |
| 2009/0075381 A1 | 3/2009 | Clarke et al. | |
| 2009/0081171 A1 | 3/2009 | Fu et al. | |
| 2009/0136457 A1 | 3/2009 | Sing et al. | |
| 2009/0092653 A1 | 4/2009 | Colter et al. | |
| 2009/0104158 A1 | 4/2009 | Young et al. | |
| 2009/0104163 A1 | 4/2009 | Deans et al. | |
| 2009/0104164 A1 | 4/2009 | Zhang et al. | |
| 2009/0123437 A1 | 5/2009 | Takebe | |
| 2009/0124007 A1 | 5/2009 | Cho | |
| 2009/0126482 A1 | 5/2009 | Heidaran et al. | |
| 2009/0136471 A1 | 5/2009 | Heidaran et al. | |
| 2009/0142831 A1 | 6/2009 | Hariri | |
| 2009/0149371 A1 | 6/2009 | Mistry et al. | |
| 2009/0169522 A1 | 7/2009 | Danilkovitch et al. | |
| 2009/0169597 A1 | 7/2009 | Brown et al. | |
| 2009/0170200 A1 | 7/2009 | Yeh et al. | |
| 2009/0186005 A1 | 7/2009 | Kim et al. | |
| 2009/0186006 A1 | 7/2009 | Murphy | |
| 2009/0202479 A1 | 8/2009 | Shi et al. | |
| 2009/0208463 A1 | 8/2009 | Pittenfer et al. | |
| 2009/0214484 A1 | 8/2009 | Mironov | |
| 2009/0214493 A1 | 8/2009 | Pittenger et al. | |
| 2009/0220464 A1 | 9/2009 | Aggarwal et al. | |
| 2009/0226406 A1 | 9/2009 | Hariri | |
| 2009/0232781 A1 | 9/2009 | Fu | |
| 2009/0232782 A1 | 9/2009 | Fu | |
| 2009/0238801 A1 | 9/2009 | Woodbury et al. | |
| 2009/0252710 A1 | 10/2009 | Zhang et al. | |
| 2009/0257989 A1 | 10/2009 | Vanguri et al. | |
| 2009/0274665 A1 | 11/2009 | Akabutu et al. | |
| 2009/0280093 A1 | 11/2009 | Friedlander | |
| 2009/0285842 A1 | 11/2009 | Davies et al. | |
| 2009/0291061 A1 | 11/2009 | Riordan et al. | |
| 2009/0304639 A1 | 12/2009 | Yokoo et al. | |
| 2009/0305406 A1 | 12/2009 | Pytlik et al. | |
| 2009/0311223 A1 | 12/2009 | Ichim | |
| 2009/0311782 A1 | 12/2009 | Chiou et al. | |
| 2009/0324609 A1 | 12/2009 | Lodie et al. | |
| 2010/0008890 A1 | 1/2010 | Mays et al. | |
| 2010/0008992 A1 | 1/2010 | Ichim | |
| 2010/0015705 A1 | 1/2010 | Vodyanyk et al. | |
| 2010/0015712 A1 | 1/2010 | Skuragawa et al. | |
| 2010/0021434 A1 | 1/2010 | Melamed et al. | |
| 2010/0028306 A1 | 2/2010 | Clarke et al. | |
| 2010/0028997 A1 | 2/2010 | Lin | |
| 2010/0047214 A1 | 2/2010 | Abramson et al. | |
| 2010/0047351 A1 | 2/2010 | Zeitlin et al. | |
| 2010/0068191 A1 | 3/2010 | Danilkovich et al. | |
| 2010/0120015 A1 | 5/2010 | Hariri | |
| 2010/0124569 A1 | 5/2010 | Abbot | |
| 2010/0143312 A1 | 6/2010 | Hariri | |
| 2010/0172830 A1 | 7/2010 | Heidaran | |
| 2010/0183571 A1 | 7/2010 | Paludan et al. | |
| 2010/0260847 A1 | 10/2010 | Hariri | |
| 2010/0291679 A1 | 11/2010 | Edinger et al. | |
| 2010/0297689 A1 | 11/2010 | Edinger et al. | |
| 2010/0323446 A1 | 12/2010 | Barnett | |
| 2011/0003387 A1 | 1/2011 | Abbot et al. | |
| 2011/0206645 A1 | 8/2011 | Zhang et al. | |
| 2011/0217271 A1 | 9/2011 | Hariri | |
| 2011/0217272 A1 | 9/2011 | Hariri | |
| 2011/0223141 A1 | 9/2011 | Hariri | |
| 2011/0250182 A1 | 10/2011 | Abbot et al. | |
| 2011/0250185 A1 | 10/2011 | Paludan et al. | |
| 2011/0280843 A1 | 11/2011 | Edinger et al. | |
| 2011/0280845 A1 | 11/2011 | Edinger et al. | |
| 2011/0280849 A1 | 11/2011 | Zhang et al. | |
| 2011/0311491 A1 | 12/2011 | Edinger et al. | |
| 2011/0318401 A1 | 12/2011 | Hariri et al. | |
| 2012/0020936 A1 | 1/2012 | Hariri | |
| 2012/0034195 A1 | 2/2012 | Hariri | |
| 2012/0058089 A1 | 3/2012 | Hariri | |
| 2012/0121550 A1 | 5/2012 | Heidaran | |
| 2012/0148553 A1 | 6/2012 | Hariri et al. | |

FOREIGN PATENT DOCUMENTS

| | | |
|---|---|---|
| CN | 1597937 | 3/2005 |
| CN | 1786154 | 6/2006 |
| CN | 1810959 | 8/2006 |
| CN | 100344757 C | 10/2007 |
| CN | 101210232 | 7/2008 |
| CN | 101270349 | 9/2008 |
| CN | 101418284 | 4/2009 |
| CN | 101451124 | 6/2009 |
| CN | 101469322 | 7/2009 |
| CN | 101480410 | 7/2009 |
| CN | 101492654 | 7/2009 |
| CN | 101525594 | 9/2009 |
| CN | 101575590 | 11/2009 |
| CN | 101591643 | 12/2009 |

(56) References Cited

FOREIGN PATENT DOCUMENTS

| | | |
|---|---|---|
| CN | 101591644 | 12/2009 |
| CN | 101608174 | 12/2009 |
| EP | 0333328 | 9/1989 |
| EP | 0529751 | 3/1993 |
| EP | 0552380 | 7/1993 |
| EP | 1264877 | 12/2002 |
| EP | 1442115 | 5/2003 |
| EP | 1405649 | 4/2004 |
| EP | 1641915 | 1/2005 |
| EP | 1727892 | 12/2006 |
| EP | 1974016 | 10/2008 |
| EP | 2014767 | 1/2009 |
| EP | 2083071 | 7/2009 |
| JP | 2003235549 | 12/2002 |
| JP | 2005151907 | 11/2003 |
| JP | 2005034030 | 2/2005 |
| JP | 2009065879 | 4/2009 |
| KR | 2004 0024170 | 3/2004 |
| KR | 100791487 B1 | 12/2007 |
| KR | 100818214 | 4/2008 |
| KR | 2009055691 | 6/2009 |
| KR | 2009065814 | 6/2009 |
| KR | 2009076483 | 7/2009 |
| KR | 2009090850 | 8/2009 |
| WO | WO 1991/001140 | 2/1991 |
| WO | WO 1991/0006667 | 5/1991 |
| WO | WO 1993/004169 | 3/1993 |
| WO | WO 1995/022611 | 8/1995 |
| WO | WO 1996/034035 | 10/1996 |
| WO | WO 1996/039101 | 12/1996 |
| WO | WO 1998/037903 | 9/1998 |
| WO | WO 1999/003973 | 1/1999 |
| WO | WO 1999/064566 | 12/1999 |
| WO | WO 2000/017325 | 3/2000 |
| WO | WO 2000/027999 | 5/2000 |
| WO | WO 2000/038762 | 7/2000 |
| WO | WO 2000/073421 | 12/2000 |
| WO | WO 2001/093909 | 12/2001 |
| WO | WO 2002/0046373 | 6/2002 |
| WO | WO 2002/0063962 | 8/2002 |
| WO | WO 2002/064755 | 8/2002 |
| WO | WO 2003/0068937 | 8/2003 |
| WO | WO 2003/086373 | 10/2003 |
| WO | WO 2003/087333 | 10/2003 |
| WO | WO 2003/087392 | 10/2003 |
| WO | WO 2003/102151 | 12/2003 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/097190 | 10/2005 |
| WO | WO 2005/105992 | 11/2005 |
| WO | WO 2005/0055929 | 1/2006 |
| WO | WO 2006/015214 | 2/2006 |
| WO | WO 2006/111706 | 10/2006 |
| WO | WO 2007/047465 | 4/2007 |
| WO | WO 2007/047468 | 4/2007 |
| WO | WO 2007/073552 | 6/2007 |
| WO | WO 2007/079183 | 7/2007 |
| WO | WO 2007/087292 | 8/2007 |
| WO | WO 2007/087293 | 8/2007 |
| WO | WO 2007/089627 | 8/2007 |
| WO | WO 2007/091255 | 8/2007 |
| WO | WO 2007/108003 | 9/2007 |
| WO | WO 2007/121443 | 10/2007 |
| WO | WO 2007/123363 | 11/2007 |
| WO | WO 2007/0124594 | 11/2007 |
| WO | WO 2008/0019148 | 2/2008 |
| WO | WO 2008/036374 | 3/2008 |
| WO | WO 2008/036447 | 3/2008 |
| WO | WO 2008/051568 | 5/2008 |
| WO | WO 2008/060541 | 5/2008 |
| WO | WO 2008/066330 | 6/2008 |
| WO | WO 2008/088738 | 7/2008 |
| WO | WO 2008/100497 | 8/2008 |
| WO | WO 2008/129563 | 10/2008 |
| WO | WO 2008/144820 | 12/2008 |
| WO | WO 2008/151846 | 12/2008 |
| WO | WO 2008/152640 | 12/2008 |
| WO | WO 2008/156659 | 12/2008 |
| WO | WO 2009/007979 | 1/2009 |
| WO | WO 2009/023246 | 2/2009 |
| WO | WO 2009/028870 | 3/2009 |
| WO | WO 2009/031606 | 3/2009 |
| WO | WO 2009/035612 | 3/2009 |
| WO | WO 2009/037690 | 3/2009 |
| WO | WO 2009/046346 | 4/2009 |
| WO | WO 2009/046377 | 4/2009 |
| WO | WO 2009/052132 | 4/2009 |
| WO | WO 2009/092092 | 7/2009 |
| WO | WO 2009/114860 | 9/2009 |
| WO | WO 2009/134429 | 11/2009 |
| WO | WO 2009/134532 | 11/2009 |
| WO | WO 2009/144718 | 12/2009 |
| WO | WO 2009/144720 | 12/2009 |
| WO | WO 2009/152186 | 12/2009 |
| WO | WO 2012/0009422 | 1/2012 |

OTHER PUBLICATIONS

Meyer, T.P.H.; et al; "Analysis and Cryopreservation of hematopoietic stem and progenitor cells from umbilical cord blood." Cytotheraby, 8, 265-276, 2006.*
Berz, David; et al; "Cryopreservation of Hematopoietic Stem Cells." American Journal of Hematology, 82, 463-472, 2007.*
Brooke, Gary; et al; "Manufacture of human placenta-derived mesenchymal stem cells for clinical trials" British Journal of Haematology, 144, 571-579, 2008 (Year: 2008).*
ISA, PCT International Search Report dated Feb. 24, 2010 for application No. PCT/US2009/004740.
U.S. Appl. No. 12/618,664, filed Nov. 13, 2009, Hariri.
U.S. Appl. No. 12/624,359, filed Nov. 23, 2009, Hariri.
U.S. Appl. No. 12/687,851, filed Jan. 10, 2010, Paludan et al.
Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Anker In't P, et al., "Isolation of Mesenchymal Stem Cells of Fetal or Maternal Origin from Human Placenta," Stem Cells, 2004; 22:1338-45.
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Belvedere, et al., "Increased Blood Volume and CD34(+)CD38(−) Progenitor Cell Recovery Using a Novel Umbilical Cord Blood Collection System," Stem Cells 18(4):245-251 (2000).
Bornstein, et al., "A Modified Cord Blood Collection Method Acheives Sufficient Cell Levels for Transplantation in Most Adult Patients," Stem Cells (2005) 23, 324-334.
Campagnoli, et al., "Identification of Mesenchymal Stem/Progenitor Cells in Human First-Trimester Fetal Blood, Liver, and Bone Marrow." Blood 98(8):2396-402 (2001).
Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).

(56) References Cited

OTHER PUBLICATIONS

Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol. , 50(3):187-195 (2003).
Cosma, et al., "Use and Application of Stem Cells in Toxicology," SOT 2003 Annual Meeting, p. 4, Abstract 19.
Czarneski, et al., "Effects of Cord Blood Transfer on the Hematopoietic Recovery Following Sublethal Irradiation in MRL lpr/lpr Mice," Proc. Soc. Exp. Biol. Med. 220(2):79-87 (1999).
Database WPI Week 200357 Derwent Publications Ltd., London, GB, AN 2003-59905 & CN 1 407 888 A (Zhou S) Apr. 2, 2003 (Apr. 2, 2003).
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood, 2000; 96(13): 4096-4102.
Davila, et al., "Use and Application of Stem Cells in Toxicology," Toxicological Sciences 79:214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).
Edinger, et al., "Characterization of Placental Derived Adherent Cells (PDAC): A Novel Type of Stem Cells Isolated from Human Placenta," Blood, Journal of the American Society of Hematology, vol. 108, No. 11, Nov. 2006, 480a, Abstract # 1685.
Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Ende, et al., "Human Umbilical Cord Blood Cells Amerliorate Alzheimer's Disease in Transgenic Mice, " J. Med. 32(3-4):241-7 (2001).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2001).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Fasouliotis, et al., "Human umbilical cord blood banking and transplantation: a state of the art," Eur. J. Obstet. Gynecol. Reprod. Biol. 90(1):13-25 (2000).
Frank H G, et al., "Cell culture models of human trophoblast: primary culture of trophoblast—a workshop report." Placent Apr. 2001, vol. 22 Suppl A, Apr. 2001 (Apr. 2001), pp. S107-S109, XP002443188 ISSN: 0143-4004.
Gluckman, et al., "Cord Blood Heamatopoietic Stem Cells: Biology and Transplantation," In: Hematology, American Society of Hematology Education Program Book (1998) p. 1-14.
Gluckman, et al., "Results of Unrelated Umbilical Cord Blood Hematipoeietic Stem Cell Transplant," Transfusion Cinique et Biologique 8(3):146-154 (2001).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Hatzopoulos, et al. "Isolation and characterization of endothelial progenitor cells from mouse embryos," Development. 125(8):1457-68 (1998).
Herrera, et al., "Mesenchymal Stem Cells Contribute to the Renal Repair of Acute Tubular Epithelial Injury,"• Int. J. Mol. Med., 2004: 14(6):1035-41.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000 (Dec. 1, 2000), pp. 1768-1771, XP002263649 ISSN:0036-8075.
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells,"• Biochemical and Biophysical Research Communications, 2007; 362:347-53.
Huss, "Isolation of Primary and Immortalized CD34– Hematopoietic and Mesenchymal Stem Cells from Various Sources," Stem Cells 18:1-9 (2000).
Huss, "Perspectives on the Morphology and Biology of CD34-Negative Stem Cells," J. Hemather. Stem. Cell Res. 9(6):783-793 (2000).

(56) References Cited

OTHER PUBLICATIONS

Igura, et al., "Isolation and Characterization of Mesencymal Progenitor Cells from Chorionic Villi of Human Placenta," Cytotherapy 6(6): 543-553 (2004).
International Preliminary Report on Patentability from PCT/US2006/049491 dated Jan. 14, 2008.
International Search Report and Written Opinion from PCT/US2009/004740 dated Feb. 24, 2010.
Iwasaki, "Recent Advances in the Treatment of Graft-Versus-Host Disease,"• Clin. Med. Res., 2004; 2(4):243-52.
Jaiswal, et al., "Osteogenic Differentiation of Purified, Culture-Expanded Human Mesenchymal Stem Cells in vitro," J. Cell Biochem. 64(2):295-312 (1997).
Jones, et al., "Isolation and Characterization of Bone Marrow Multipotential Mesenchymal Progenitor Cells," Arthritis Rheum. 46(12):3349-3360 (2002).
Kawata, et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.
Kolf, et al., "Biology of adult mesenchymal stem cells: regulation of niche, self-renewal and differentiation," Arthritis Research & Therapy 2007, 9:204.
Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Surce of Hmatopoietic Sem Cells for Transplantation into Unrelated Recipients," N. Engl. J. Med. 335:157-166 (1996).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Lebkowski, et al., "Serum and Plasma Levels of FGF-2 and VEGF in Healthy Blood Donors," Cancer J. 7(Suppl 2):S83-S93 (2001).
Le Blanc, et al., "Treatment of Severe Acute Graft-Versus-Host Disease With Third Party Haploidentical Mesenchvmal Stem Cells," Lancet, 2004; 363(9419):1439-41.
Leonard, et al., "The Role of ABC Transporters in Clinical Practice," Oncologist. 8:411-424 (2003).
Li, et al., "Mesenchymal Stem Cells Derived from Human Placenta Suppress Allogenic Umbilical Cord Blood Lymphocyte Proliferation." Cell Res. 15: 539-547 (2005).
Lin, et al. "Murine CD200(+)CK7(+) trophoblasts in a poly (I:C)-induced embryo resorption model." Reproduction (Cambridge), vol. 130, No. 4, Oct. 2005 (Oct. 2005), pp. 529-537, XP002443406 ISSN: 1470-1626.
Lipinski et al., "Human Trophoblast Cell-Surface Antigen Defined by Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Ma, et al., "Development of an in vitro Human Placenta Model by the Cultivation of Human Trophoblasts in a Fiber-Based Bioreactor System," Tissue Engineering 5, 91-102 (1999).

Ma, et al., "Human Umbilical Cord Wharton's Jelly-Derived Mesenchymal Stem Cells Differentiation into Nerve-Like Cells," Chinese Med. Jour., 118(23):1987-93 (2005).
Mackay, et al., "Chondrogenic Differentiation of Cultured Human Mesenchymal Stem Cells from Marrow," Tissue Engineering, 1998; 4(4):415-28.
Mariotti, et al., "Comarative Characteristics of Mesenchymal Stem Cells from Human Bone Marrow and Placenta: CD10, CD49d, and CD56 Make a Difference," Stem Cells and Development 17:1039-1042 (2008).
McKay, Ron, "Stem cells—hype and hope," Nature, vol. 406, Jul. 27, 2000.
McMaster et al, "Human Placental HLA-G Expression is Restricted to Differentiated Cytotrophoblasts," J. Immunol. 154(8):3771-3778 (1995).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki, et al., "Isolation of Multipotent Stem Cells from Placenta." AASLD Abstracts, Hepatology, Oct. 2003, Abstract 279, p. 290A.
Miki, et al., "Production of Hepatocytes from Human Amniotic Stem Cells." Hepatology, Abstract 20, vol. 36, No. 4, Pt. 2, 2002.
Miki, et al., "Stem Cell Characteristics of Amniotic Epithelial Cells." Stem Cells Express, published online Aug. 9, 2005; doi:10.1634/stemcells.2004-0357.
Moreau et al., "Myofibroblastic Stromal Cells Isolated From Human Bone Marrow Indue the Proliferation of Both Early Myeloid and B-Lymphoid Cells," Blood 82:2396-2405 (1993).
Morgan et al., "Human Placental Cell Culture," Biochemical Society Transactions 12 (1984).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol., 2004; 15(7):1794-1804.
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(I1):4200-06.
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Paludan, et al., "Immune Suppression by Placenta Derived Adherent Cells (PDAC) Correlate with Monocyte Chemoattractant Protein-1 and 1L-2 Secretion," Blood 108 (2006) (abstract only).
Paludan, et al., "Placental Derived Stem Cells (PDAC) Suppress the Allo-MLR and the EBV Regression Assay," http://www.call4abstract.com/hem/finalpreview.php?absnum=552996 (2006).
Panepucci, et al., "Comparison of Gene Expression of Umbilical Cord Vein and Bone Marrow-Derived Mesenchvmal Stem Cells," Stem Cells, 2004; 22(7):1263-78.
Papaioannou, et al., "Stem Cells from Early Mammalian Embryos" Stem Cells Handbook:19-31 (2004).
Pera, et al., "Human Embryonic Stem Cells," J. Cell. Sci. 113:5-10 (2000).

(56) References Cited

OTHER PUBLICATIONS

Pountos, et al., "Mesenchymal Stem Cell Tissue Engineering: Techniques for Isolation, Expansion and Application," Injury Int. J. Care Injured, 2007; 38(Supp. 4):S23-33.
Reyes, et al. Origin of endothelial progenitors in human postnatal bone marrow.J Clin Invest. 109(3):337-46 (2002).
Reyes, et al., "Purification and ex vivo Expansion of Postnatal Human Marrow Mesodermanl Progenitor Cells," Blood 98(9):2615-2625 (2001).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Rojewski, et al., "Phenotypic Characterization of Mesenchymal Stem Cells from Various Tissues," Transfusion Medicine and Hemotherapy, 2008;35:168-184.
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Russo, "Fighting Darwin's Battles. Symposium Marks Evolutionist Victory, Anti-Evolution Growth" The Scientist 15:6 (2001).
Saito et al., "Effect of washing procedures on cord blood transplantation: Engraftment of human CD45+ cells in NOD/SCID mice transplanted with cord blood stem cells with or without washing out of DMSO after cryopreservation," Database Biosis, Biosciences Information Service, Philadelphia, PA, US; Nov. 16, 2000; XP-002567840; Database accession No. PREV200100322062 Abstract.
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Secco, et al., "Gene Expression Profile of Mesenchymal Stem Cells from Paired Umbilical Cord Units: Cord is Different from Blood," Stem Cell Rev and Rep (2009) 5:387-401.
Schutz, et al., "Isolation and Cultivation of Endothelial Cells Derived from Human Placenta," Eur. J. Cell Biol. 395-401 (1996).
ScienCell—Human Amniotic Epithelial Cells, Catalogue No. 7100. http://www.sciencellonline.com/site/products/7100.php.
ScienCell—Human Villous Mesenchymal Fibroblasts (HVMF), Catalogue No. 7130. http://www.seincecellonline.com/site/products/7130.php.
Shamblott, et al., "Derivation of Pluripotent Stem Cells from Cultured Human Primordial Germ Cells," Proc. Natl. Acad. Sci. USA 95(23):13726-13731 (1998).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Southard, et al., "Important Components of the UW Solution$^{1,2}$," Transplantation 49(2): 251-257 (1990).
Stanworth, et al., "Stem Cells: Progress in Research and Edging towards the Clinical Setting," Clin. Med. 1(5):378-382 (2001).
Tarrade et al., "Characterization of Human Villous and Extravillous Trophoblasts Isolated from First Trimester Placenta," Laboratory Investigation 81(9):1199-1211 (2001).

Thomson, et al., Embryonic stem cell lines derived from human blastocysts. Science. 282 (5391): 1145-7 (1998).
Toma, et al., "Human Mesenchymal Stem Cells Differentiate to a Cardiomyocyte Phenotype in the Adult Murine Heart," Circulation, 2002; 105:93-98.
Truman et al., "Human Placental Cytotrophoblast Cells: Identification and Culture," Arch Gynecol. Obstet. 246:39-49 (1989).
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering, 2005; 100(1):12-27.
Viacord, Umblicical cord blood can save lives (Informational brochure), Boston: ViaCell Centr-Bro R1 Oct. 2001 (2001).
Wang, et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe, et al, "Multilineage Potential of Human Placenta-Derived Mesenchymal Cells," Blood 100(11):517a, Abstract 2022 (2002).
Woods, et al., "Osomometric and permeability characteristics of human placental/umbilical cord blood CD34+ cells and their application to cryopreservation," J. Hematother. Stem Cell Res. 9(2):161-173 (2000).
Ye, et al., "Recovery of Placental-Derived Adherent Cells with Mesenchymal Stem Cell Characteristics," Blood 98(11/1):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen, B. Linju et al, "Isolation of multipotent cells from human term placenta" Stem Cells (Dayton, Ohio) 2005, vol. 23, No. 1, Jan. 2005 (Jan. 2005), pp. 3-9, XP002443187 ISSN: 1065-5099.
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol., 2003; 47(1):109-16.
Zhang, et al., "Human Placenta-Derived Mesenchymal Progenitor Cells Support Culture Expansion of Long-Term Culture-Initiating Cells from Cord Blood CD34+ Cells." Exp. Hematol. 32: 657-664 (2004).
Zimmermann, et al., "Lack of telomerase activity in human mesenchymal stem cells," Leukemia 92003) 17, 1146-1149.
Notice of Allowance dated Sep. 15, 2005 in U.S. Appl. No. 10/004,942, now U.S. Pat. No. 7,045,148.
Office Action dated Dec. 16, 2004 in U.S. Appl. No. 10/004,942, now U.S. Pat. No. 7,045,148.
Office Action dated Dec. 5, 2003 in U.S. Appl. No. 10/004,942, now U.S. Pat. No. 7,045,148.
Office Action dated Jun. 15, 2004 in U.S. Appl. No. 10/004,942, now U.S. Pat. No. 7,045,148.
Office Action dated Jun. 20, 2005 in U.S. Appl. No. 10/004,942, now U.S. Pat. No. 7,045,148.
Office Action dated May 7, 2003 in U.S. Appl. No. 10/004,942, now U.S. Pat. No. 7,045,148.
Notice of Allowance dated Aug. 16, 2007 in U.S. Appl. No. 10/074,976, now U.S. Pat. No. 7,311,904.
Office Action dated Jan. 5, 2006 in U.S. Appl. No. 10/074,976, now U.S. Pat. No. 7,311,904.
Office Action dated Mar. 22, 2007 in U.S. Appl. No. 10/074,976, now U.S. Pat. No. 7,311,904.
Office Action dated Sep. 20, 2006 in U.S. Appl. No. 10/074,976, now U.S. Pat. No. 7,311,904.
Office Action dated Sep. 23, 2004 in U.S. Appl. No. 10/074,976, now U.S. Pat. No. 7,311,904.
Notice of Allowance dated Sep. 10, 2007 in U.S. Appl. No. 10/366,671, now U.S. Pat. No. 7,311,905.

(56) References Cited

OTHER PUBLICATIONS

Office Action dated Jan. 19, 2006 in U.S. Appl. No. 10/366,671, now U.S. Pat. No. 7,311,905.
Office Action dated May 14, 2007 in U.S. Appl. No. 10/366,671, now U.S. Pat. No. 7,311,905.
Office Action dated Oct. 10, 2006 in U.S. Appl. No. 10/366,671, now U.S. Pat. No. 7,311,905.
Notice of Allowance dated Oct. 30, 2008 in U.S. Appl. No. 10/411,655, now U.S. Pat. No. 7,498,171.
Office Action dated Feb. 28, 2008 in U.S. Appl. No. 10/411,655, now U.S. Pat. No. 7,498,171.
Office Action dated Jul. 11, 2007 in U.S. Appl. No. 10/411,655, now U.S. Pat. No. 7,498,171.
Office Action dated May 18, 2006 in U.S. Appl. No. 10/411,655, now U.S. Pat. No. 7,498,171.
Office Action dated Nov. 20, 2006 in U.S. Appl. No. 10/411,655, now U.S. Pat. No. 7,498,171.
Office Action dated Apr. 26, 2007 in U.S. Appl. No. 10/449,248.
Office Action dated Aug. 29, 2006 in U.S. Appl. No. 10/449,248.
Office Action dated Feb. 7, 2008 in U.S. Appl. No. 10/449,248.
Office Action dated Aug. 4, 2006 in U.S. Appl. No. 10/511,355.
Office Action dated Dec. 6, 2005 in U.S. Appl. No. 10/511,355.
Office Action dated Sep. 5, 2007 in U.S. Appl. No. 10/511,355.
Notice of Allowance May 21, 2007 in U.S. Appl. No. 10/640,428, now U.S. Pat. No. 7,255,879.
Office Action dated Jan. 19, 2006 in U.S. Appl. No. 10/640,428, now U.S. Pat. No. 7,255,879.
Office Action dated Oct. 18, 2006 in U.S. Appl. No. 10/640,428, now U.S. Pat. No. 7,255,879.
Office Action dated Dec. 28, 2006 in U.S. Appl. No. 10/721,144.
Office Action dated Feb. 5, 2008 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Jun. 27, 2007 in U.S. Appl. No. 10/721,144.
Office Action dated Oct. 4, 2005 in U.S. Appl. No. 10/721,144.
Final Office Action dated Apr. 2, 2009 in U.S. Appl. No. 10/721,144.
Final Office Action dated Nov. 7, 2005 in U.S. Appl. No. 10/779,369.
Office Action dated Mar. 29, 2005 in U.S. Appl. No. 10/779,369.
Notice of Allowance dated Oct. 14, 2008 in U.S. Appl. No. 10/874,828, now U.S. Pat. No. 7,468,276.
Office Action dated Apr. 6, 2007 in U.S. Appl. No. 10/874,828, now U.S. Pat. No. 7,468,276.
Office Action dated Dec. 13, 2007 in U.S. Appl. No. 10/874,828, now U.S. Pat. No. 7,468,276.
Office Action dated Jun. 12, 2006 in U.S. Appl. No. 10/874,828, now U.S. Pat. No. 7,468,276.
Office Action dated Sep. 9, 2008 in U.S. Appl. No. 10/874,828, now U.S. Pat. No. 7,468,276.
Notice of Allowance dated Aug. 12, 2009 in U.S. Appl. No. 11/187,400, now U.S. Pat. No. 7,638,141.
Office Action dated Apr. 20, 2007 in U.S. Appl. No. 11/187,400, now U.S. Pat. No. 7,638,141.
Office Action dated Jan. 4, 2008 in U.S. Appl. No. 11/187,400, now U.S. Pat. No. 7,638,141.
Office Action dated May 22, 2008 in U.S. Appl. No. 11/187,400, now U.S. Pat. No. 7,638,141.
Office Action dated Feb. 20, 2009 in U.S. Appl. No. 11/187,400, now U.S. Pat. No. 7,638,141.
Final Office Action dated Dec. 9, 2009 in U.S. Appl. No. 11/593,348.
Office Action dated May 15, 2009 in U.S. Appl. No. 11/593,348.
Notice of Allowance dated Dec. 1, 2009 in U.S. Appl. No. 11/648,802.
Office Action dated Dec. 3, 2008 in U.S. Appl. No. 11/648,802.
Restriction Requirement dated Mar. 23, 2009 in U.S. Appl. No. 11/648,804.
Non-Final Office Action dated Oct. 21, 2009 in U.S. Appl. No. 11/648,804.
Office Action dated Jan. 26, 2009 in U.S. Appl. No. 11/648,813.
Final Office Action dated Oct. 27, 2009 in U.S. Appl. No. 11/648,813.
Request to Record a Change in the Request dated Jun. 17, 2008 in International Application No. PCT/US2006/049491.
U.S. Appl. No. 13/340,528, filed Dec. 29, 2011, Abramson.
Barlogie et al., "High-dose therapy immunomodulatory drugs in multiple myeloma," Seminars in Oncology, 2002, 29 (6):26-33.
Nagayama et al., "Immunological reconstitution after cord blood transplantation for an adult patient", Bone Marrow Transplantation 24: 211-213 (1999).
Potgens et al., "Human Trophoblast Contains an Intracellular Protein Reactive with and Antibody against CD133—A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
U.S. Appl. No. 13/340,550, filed Dec. 29, 2011, Abramson et al.
U.S. Appl. No. 13/340,557, filed Dec. 29, 2011, Abramson et al.
U.S. Appl. No. 13/340,589, filed Dec. 29, 2011, Abbot et al.
U.S. Appl. No. 13/473,509, filed May 16, 2012, Edinger et al.
U.S. Appl. No. 13/480,370, filed May 24, 2012, Edinger et al.
Final Office Action dated Dec. 15, 2011 in U.S. Appl. No. 10/721,144.
Non Final Office Action dated Feb. 1, 2011 in U.S. Appl. No. 10/721,144.
Final Office Action dated Sep. 14, 2010 in U.S. Appl. No. 10/721,144.
Office Action dated Mar. 18, 2010 in U.S. Appl. No. 10/721,144.
Advisory Action dated Oct. 7, 2009 in U.S. Appl. No. 10/721,144.
Office Action dated May 9, 2012 in U.S. Appl. No. 11/648,804.
Final Office Action dated Oct. 31, 2011 in U.S. Appl. No. 11/648,804.
Non-Final Office Action dated Apr. 21, 2011 in U.S. Appl. No. 11/648,804.
Notice of Allowance dated Sep. 29, 2011 in U.S. Appl. No. 11/648,813.
Final Office Action dated Jul. 20, 2010 in U.S. Appl. No. 11/648,824.
U.S. Appl. No. 13/081,415, filed Apr. 6, 2011, Abbot.
U.S. Appl. No. 13/081,422, filed Apr. 6, 2011, Edinger.
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).
Notice of Allowance dated Jan. 10, 2011 in U.S. Appl. No. 11/648,813.
Non Final Office Action dated Jun. 7, 2010 in U.S. Appl. No. 11/648,813.
Final Office Action dated May 20, 2010 in U.S. Appl. No. 11/648,804.

* cited by examiner

CELL COMPOSITION AND METHODS OF MAKING THE SAME

This application claims benefit under 35 U.S.C. § 119(e) of U.S. Provisional Application No. 61/090,577, filed Aug. 20, 2008, which is hereby incorporated by reference in its entirety.

1. FIELD

Provided herein are improved compositions, e.g., pharmaceutical compositions, comprising cells, e.g., stem cells and placental cells, such as isolated human adherent placental multipotent cells, e.g., the placental multipotent cells described in section 5.3, or cells isolated from placental perfusate, e.g., total nucleated cells isolated from placental perfusate, and improved methods for making the compositions.

2. BACKGROUND

Cell compositions, e.g., stem cell compositions, have become an attractive therapy for a number of physiological deficiencies, e.g., bone marrow replacement. A need exists for improved formulations of cells, e.g., stem cells, that are to be administered to individuals in need of such compositions.

3. SUMMARY

Provided herein are improved methods of making compositions comprising cells, e.g., isolated placental cells, such as placental stem cells, placental multipotent cells, placental cells that can be expanded and have the potential to differentiate into at least two different cell types, e.g., osteogenic and chondrogenic cell types, or cells isolated from placental perfusate, e.g., total nucleated cells isolated from placental perfusate, and compositions comprising such cells, e.g., that are suitable for administration to an individual. The improved methods use specific steps and specific compositions for the pre-cryopreservation treatment, cryopreservation, and thawing of cells. In certain embodiments, the improved methods reduce or eliminate post-thaw clumping of cryopreserved cells. In preferred embodiments, the improved compositions comprise placental multipotent cells.

In one embodiment, provided herein is a method of making a composition comprising: (a) contacting cells with a solution comprising dextran and human serum albumin (HSA) to form a cell-containing solution; (b) filtering the cell-containing solution to form a filtered cell-containing solution; (c) optionally diluting the filtered cell-containing solution to about 1 to $50\times10^6$, 1 to $40\times10^6$, 1 to $30\times10^6$, 1 to $20\times10^6$, 1 to $15\times10^6$, or 1 to $10\times10^6$ cells per milliliter with a first dilution solution comprising dextran; and (d) optionally diluting the filtered cell-containing solution with a second dilution solution comprising dextran. In some embodiments, step (c) is performed where the filtered cell-containing solution in (b) comprises greater than about $15\times10^6$ cells per milliliter, wherein said diluting in step (c) is to about $15\times10^6$ cells per milliliter. In particular embodiments, step (c) is performed where the filtered cell-containing solution in (b) comprises greater than about $10\pm3\times10^6$ cells per milliliter, wherein said diluting in step (c) is to about $10\pm3\times10^6$ cells per milliliter. In some embodiments, step (c) is performed where the filtered cell-containing solution in (b) comprises greater than about $7.5\times10^6$ cells per milliliter, wherein said diluting in step (c) is to about $7.5\times10^6$ cells per milliliter. In a specific embodiment, the solution comprising dextran of step (d) does not comprise human serum albumin. In a specific embodiment, the cells of the filtered cell-containing composition are cryopreserved prior to step (d). In certain embodiments, if the number of cells is less than about $10\pm3\times10^6$ cells per milliliter following step (a), filtration is optional. In certain embodiments, if the number of cells is less than about $7.5\times10^6$ cells per milliliter following step (a), filtration is optional.

In some embodiments, said dextran in said first dilution solution or said second solution is 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran. In some embodiments, said dextran in said first dilution solution or said second solution is about 11%, 12%, 13%, 14%, 15%, 16%, 17%, 18%, 19% or 20% dextran. The dextran in the first dilution solution or second dilution solution can be dextran of any molecular weight, e.g., dextran having a molecular weight of from about 1 kDa to about 150 kDa, about 1 kDa to about 125 kDa, about 1 kDa to about 100 kDa, about 1 kDa to about 75 kDa, about 1 kDa to about 50 kDa, or about 1 kDa to about 25 kDa. In some embodiments, the dextran in the first dilution solution or second dilution solution has a molecular weight of about 1 kDA to about 10 kDa, about 30 kDa to about 50 kDa, or about 60 kDa to about 80 kDa. In another specific embodiment, said dextran in said first dilution solution or said second dilution solution is dextran 1. In another specific embodiment, said dextran in said first dilution solution and said second dilution solution is dextran 1. In another specific embodiment, said dextran in said first dilution solution or said second dilution solution is dextran 70. In another specific embodiment, said dextran in said first dilution solution and said second dilution solution is dextran 70. In another specific embodiment, said dextran in said first dilution solution or said second dilution solution is dextran 40. In another specific embodiment, said dextran in said first dilution solution and said second dilution solution is dextran 40. In another specific embodiment, said dextran 40 in said first dilution or said second dilution solution is 2.5% to 10% dextran 40. In some embodiments, said dextran 40 in said first dilution solution or said second solution is about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran 40. In some embodiments, said dextran in said first dilution solution or said second solution is about 11%, 12%, 13%, 14%, 15%, 16%, 17%, 18%, 19% or 20% dextran 40. In another specific embodiment, said dextran 40 in said first dilution solution is 5.0% dextran 40. In another specific embodiment, said dextran 40 in said first dilution solution is 5.5% dextran 40. In another specific embodiment, said dextran 40 in said second dilution solution is 10% dextran 40.

In other embodiments, said first and/or second dilution solutions may comprise a polysaccharide in addition to or other than, i.e., in place of, dextran. For example, in some embodiments, said first and/or second dilution solutions comprises maltodextran (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% maltodextrin), trehalose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% trehalose), or hetastarch (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% hetastarch). In other embodiments, said first and/or second dilution solutions comprises sucrose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% sucrose), heparin (e.g., 55 USP units/mL heparin), or glycogen (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% glycogen). In a particular embodiment, said first and/or second dilution solutions comprises maltodextran in addition to or other than, i.e., in place of, dextran. In another particular embodiment, said first and/or second dilution solutions comprises trehalose in addition to or other than, i.e., in place of, dextran. In another particular embodiment, said first and/or second dilution solutions comprises hetastarch in addition to or other than, i.e., in place of, dextran.

In another specific embodiment, said HSA in said solution comprising HSA is about 1 to 17% HSA. In another specific embodiment, said HSA in said solution comprising HSA is about 1%, 2%, 3%, 4%, 5%, 6%, 7%, 8%, 9%, 10%, 11%, 12%, 13%, 14%, 15%, 16% or 17% HSA. In another specific embodiment, said HSA in said solution comprising HSA is about 4 to 10% HSA. In another specific embodiment, said HSA in said solution comprising HSA is about 3.125% HSA. In another specific embodiment, said HSA in said solution comprising HSA is about 5% HSA. In another specific embodiment, said HSA in said solution comprising HSA is about 10% HSA. In another specific embodiment, said HSA in said solution comprising HSA is about 16.875% HSA. In another specific embodiment, said HSA in said first dilution solution is about 1 to 17% HSA. In another specific embodiment, said HSA in said first dilution solution is about 1%, 2%, 3%, 4%, 5%, 6%, 7%, 8%, 9%, 10%, 11%, 12%, 13%, 14%, 15%, 16% or 17% HSA. In another specific embodiment, said HSA in said first dilution solution is about 4 to 10% HSA. In another specific embodiment, said HSA in said first dilution solution is about 3.125% HSA. In another specific embodiment, said HSA in said first dilution solution is about 5% HSA. In another specific embodiment, said HSA in said first dilution solution is about 10% HSA. In another specific embodiment, said HSA in said first dilution is about 16.875% HSA.

In other embodiments, bovine serum albumin (BSA)(e.g., about 1%, 2%, 3%, 4%, 5%, 6%, 7%, 8%, 9%, 10%, 11%, 12%, 13%, 14% or 15% BSA) or fetal bovine serum (FBS) (e.g., about 1%, 2%, 3%, 4%, 5%, 6%, 7%, 8%, 9%, 10%, 11%, 12%, 13%, 14% or 15% FBS) may be used in addition to or in place of, i.e., instead of HSA in said solution.

In some embodiments, the ratio of HSA to dextran, e.g., dextran 1, dextran 40 or dextran 70, in the first solution is between about 6:1 HSA:dextran to about 1:2.6 HSA:dextran. In some embodiments, the ratio of HSA to dextran is about 6:1, 5.5:1, 5:1, 4.5:1, 4:1, 3.5:1, 3:1, 2.5:1, 2.0:1, 1.5:1, 1:1, 1:1.5, 1:2 or 1:2.6 HSA:dextran. In some embodiments, the ratio of HSA to dextran, e.g., dextran 1, dextran 40 or dextran 70, in the first solution is about 3.13% HSA/8.25% dextran. In some embodiments, the ratio of HSA to dextran, e.g., dextran 1, dextran 40 or dextran 70, in the first solution is about 16.88% HSA/2.75% dextran. In particular embodiments, the ratio of HSA to dextran, e.g., dextran 1, dextran 40 or dextran 70, in the first solution is about 10% HSA/ 5.5% dextran, e.g., dextran 1, dextran 40 or dextran 70.

In another specific embodiment, said solution in step (a) or cell-containing solution comprises a cryoprotectant. In a more specific embodiment, said cryoprotectant is dimethylsulfoxide (DMSO). In a particular embodiment, the solution recited in step (a) comprises about 1% to about 15%, about 2.5% to about 15%, about 2.5% to about 10%, about 5% to about 15%, about 5% to about 10% or about 10% to about 15% DMSO. In a particular embodiment, the solution recited in step (a) comprises about 1%, 2%, 3%, 4%, 5%, 6%, 7%, 8%, 9%, 10%, 11%, 12%, 13%, 14% or 15% DMSO. In a particular embodiment, the solution recited in step (a) comprises about 5% DMSO. In another specific embodiment, said first dilution solution further comprises a cryoprotectant. In a more specific embodiment, said cryoprotectant is dimethylsulfoxide (DMSO). In a particular embodiment, said first dilution solution further comprises about 1% to about 15%, about 2.5% to about 15%, about 2.5% to about 10%, about 5% to about 15%, about 5% to about 10% or about 10% to about 15% DMSO. In a particular embodiment, said first dilution solution further comprises about 1%, 2%, 3%, 4%, 5%, 6%, 7%, 8%, 9%, 10%, 11%, 12%, 13%, 14% or 15% DMSO. In a particular embodiment, said first dilution solution further comprises about 5% DMSO.

In a specific embodiment, said first dilution solution comprises about 5.5% dextran 40, about 10% HSA, and about 5% DMSO.

In a particular embodiment, said method produces a composition comprising cells and about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran, e.g., dextran 1, dextran 40 or dextran 70. In another particular embodiment, said method produces a composition comprising cells and about 7.5% to about 9% dextran, e.g., dextran 40. In another specific embodiment, said method produces a composition comprising about $1.5 \times 10^6$ cells per milliliter to about $3.75 \times 10^6$ cells per milliliter. In another specific embodiment, said method produces a composition comprising about $1.0 \pm 0.3 \times 10^6$ cells per milliliter to about $5.0 \pm 1.5 \times 10^6$ cells per milliliter. In other specific embodiments, the method produces a composition comprising between about $1.0 \times 10^6$ cells per milliliter and $15 \times 10^6$ cells per milliliter, e.g., between about $7.5 \times 10^6$ cells per milliliter and about $15 \times 10^6$ cells per milliliter. In another specific embodiment, said method produces a composition comprising from about 1% HSA to about 15% HSA. In another specific embodiment, said method produces a composition comprising from about 1% HSA to about 10% HSA.

Further provided herein is a method of making a composition, comprising: (a) filtering a plurality of cells in a solution comprising 5.5% dextran 40 and 10% HSA through a 70 μM-150 μM filter to form a filtered cell-containing solution; (b) optionally diluting the filtered cell-containing solution with 5.5% dextran 40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (c) cryopreserving the cells; (d) thawing the cells; and (e) diluting the filtered cell-containing solution with 10% dextran 40 to produce said composition. In some embodiments, step (b) is performed where the filtered cell-containing solution in (a)

comprises greater than about $15 \times 10^6$ cells per milliliter, wherein said diluting in step (b) is to about $15 \times 10^6$ cells per milliliter. In certain embodiments, if the filtered cell-containing solution in (a) comprises less than about $15 \times 10^6$ cells per milliliter, filtration is optional. In some embodiments, step (b) is performed where the filtered cell-containing solution in (a) comprises greater than about $10 \pm 3 \times 10^6$ cells per milliliter, wherein said diluting in step (b) is to about $10 \pm 3 \times 10^6$ cells per milliliter. In certain embodiments, if the filtered cell-containing solution in (a) comprises less than about $10 \pm 3 \times 10^6$ cells per milliliter, filtration is optional. In some embodiments, step (b) is performed where the filtered cell-containing solution in (a) comprises greater than about $7.5 \times 10^6$ cells per milliliter, wherein said diluting in step (b) is to about $7.5 \times 10^6$ cells per milliliter. In certain embodiments, if the filtered cell-containing solution in (a) comprises less than about $7.5 \times 10^6$ cells per milliliter, filtration is optional. In some embodiments, step (e) comprises diluting the filtered cell-containing solution 1:1 to 1:5 (v/v) with 10% dextran 40. In some embodiments, step (e) comprises diluting the filtered cell-containing solution 1:1 to 1:11 (v/v) with 10% dextran 40. In a more specific embodiment, the cell-containing solution of step (a) additionally comprises a cryoprotectant, e.g., DMSO, e.g., about 2% to about 15% DMSO. In a particular embodiment, the solution recited in step (a) additionally comprises about 1%, 2%, 3%, 4%, 5%, 6%, 7%, 8%, 9%, 10%, 11%, 12%, 13%, 14% or 15% DMSO. In a particular embodiment, the solution recited in step (a) additionally comprises about 5% DMSO. In a preferred embodiment, the filter in step (a) is a 70 μM to 100 μM filter.

In another embodiment, provided herein is a method of making a composition, comprising: (a) centrifuging a plurality of cells to collect the cells; (b) resuspending the cells in 5.5% dextran 40; (c) centrifuging the cells to collect the cells; (d) resuspending the cells in a 5.5% dextran 40 solution that comprises 10% HSA to produce a cell-containing solution; (e) filtering the cell-containing solution through a 40 μM to 150 μM filter to produce a filtered cell-containing solution; (f) optionally diluting the filtered cell-containing solution in 5.5% dextran 40, 10% HSA, and a cryoprotectant, e.g., DMSO, e.g., 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (g) cryopreserving the cells; (h) thawing the cells; and (i) diluting the cell-containing solution 1:1 to 1:11 (v/v) with 10% dextran 40 to produce said composition. In some embodiments, step (f) is performed where the filtered cell-containing solution in (e) comprises greater than about $15 \times 10^6$ cells per milliliter, wherein said diluting in step (f) is to about $15 \times 10^6$ cells per milliliter. In particular embodiments, step (f) is performed where the filtered cell-containing solution in (e) comprises greater than about $10 \pm 3 \times 10^6$ cells per milliliter, wherein said diluting in step (f) is to about $10 \pm 3 \times 10^6$ cells per milliliter. In some embodiments, step (e) is performed where the filtered cell-containing solution in (e) comprises greater than about $7.5 \times 10^6$ cells per milliliter, wherein said diluting in step (f) is to about $7.5 \times 10^6$ cells per milliliter. In certain embodiments, if the number of cells is less than about $10 \pm 3 \times 10^6$ cells per milliliter following step (d), filtration is optional. In certain embodiments, if the number of cells is less than about $7.5 \times 10^6$ cells per milliliter following step (d), filtration is optional. In a particular embodiment, if the recited resuspending in step (d) would result in a cell-containing solution comprising less than about $10 \pm 3 \times 10^6$ cells per milliliter, the solution recited in step (d) comprises a cryoprotectant, e.g., DMSO, e.g., about 2% to about 15% DMSO, and step (f) is not performed. In a preferred embodiment, the filter in step (e) is a 70 μM to 100 μM filter.

Also provided herein is a method of making a composition, comprising: (a) filtering a solution comprising isolated placental cells, 5.5% dextran 40 and 10% human serum albumin (HSA) with a filter that removes visible cell clumps to produce a filtered isolated placental cell-containing solution; (b) optionally diluting said filtered isolated placental cell-containing solution with an amount of a solution comprising 5.5% dextran 40, 10% HSA and 5% dimethylsulfoxide (DMSO) sufficient to bring said filtered isolated placental cell-containing solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; and (c) diluting said filtered isolated placental cell-containing solution with 10% dextran 40 to produce said composition. In some embodiments, step (b) is performed where the filtered cell-containing solution in (a) comprises greater than about $15 \times 10^6$ cells per milliliter, wherein said diluting in step (b) is to about $15 \times 10^6$ cells per milliliter. In particular embodiments, step (b) is performed where the filtered cell-containing solution in (a) comprises greater than about $10 \pm 3 \times 10^6$ cells per milliliter, wherein said diluting in step (b) is to about $10 \pm 3 \times 10^6$ cells per milliliter. In some embodiments, step (b) is performed where the filtered cell-containing solution in (a) comprises greater than about $7.5 \times 10^6$ cells per milliliter, wherein said diluting in step (b) is to about $7.5 \times 10^6$ cells per milliliter. In some embodiments, step (c) comprises diluting said filtered isolated placental cell-containing solution with 10% dextran 40 at a ratio of about 1:1 to about 1:11 isolated placental cell-containing solution:dextran 40 (v/v). In some embodiments, step (c) comprises diluting said filtered isolated placental cell-containing solution with 10% dextran 40 at a ratio of about 1:1 to about 1:5 isolated placental cell-containing solution:dextran 40 (v/v). In certain embodiments, if the number of cells is less than about $10 \pm 3 \times 10^6$ cells per milliliter, filtration is optional. In certain embodiments, if the number of cells following step (a) is less than about $7.5 \times 10^6$ cells per milliliter, filtration is optional. In a specific embodiment, said filter is a 70 μM filter. In another specific embodiment, said filter is a 100 μM filter. In another specific embodiment, the filter in step (a) is a 70 μM to 100 μM filter.

In a specific embodiment of any of the above methods, the composition is a pharmaceutical composition.

In another specific embodiment of any of the above methods, the method further comprises concentrating the resulting cell composition to about $5 \times 10^6$ cells per milliliter to $1 \times 10^8$ cells per milliliter. Such a composition is useful, for example, for subcutaneous administration of the composition to an individual in need thereof.

In another aspect, provided herein are compositions, e.g., pharmaceutical compositions comprising cells, e.g., stem cells, isolated placental cells, e.g., placental stem cells or placental multipotent cells. In certain embodiments, the compositions are made by any of the methods described herein. In one embodiment, provided herein is a composition, e.g., a solution, comprising a plurality of cells, e.g., stem cells, isolated placental cells, for example, placental stem cells or placental multipotent cells, wherein said composition comprises between about $1.0 \pm 0.3 \times 10^6$ cells per milliliter to about $5.0 \pm 1.5 \times 10^6$ cells per milliliter, and wherein said composition comprises no visible cell clumps (i.e., no macro cell clumps), or substantially no such visible clumps. In certain other embodiments, the composition comprises between about $1.0 \times 10^6$ cells per milliliter and $15 \times 10^6$ cells per milliliter, e.g., between about $7.5 \times 10^6$ cells per milliliter and about 15×10⁶ cells per milliliter. In certain other embodiments, the composition comprises less than about 20×10⁶ cells per milliliter.

In some embodiments, said composition comprises about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran, e.g., dextran 1, dextran 40 or dextran 70. In a specific embodiment, said composition comprises about 7.5% to about 9% dextran 40. In a specific embodiment, said composition comprises about 5.5% dextran 40.

In other embodiments, said composition comprises a polysaccharide in addition to or other than, i.e., in place of, dextran. In certain embodiments, the polysaccharide is a polymer of glucose that does not comprise non-glucose saccharide subunits. In other embodiments, said composition comprises maltodextrin (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% maltodextrin), trehalose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% trehalose), or hetastarch (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% hetastarch). In other embodiments, said composition comprises sucrose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% sucrose), heparin (e.g., 55 USP/ml heparin), or glycogen (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% glycogen). In a particular embodiment, said composition comprises maltodextran in addition to or other than, i.e., in place of, dextran. In another particular embodiment, said composition comprises trehalose in addition to or instead of dextran. In another particular embodiment, said composition comprises hetastarch in addition to or instead of dextran.

In another specific embodiment, said composition comprises about 1% to about 17% HSA. In some embodiments, said composition comprises about 1%, 2%, 3%, 4%, 5%, 6%, 7%, 8%, 9%, 10%, 11%, 12%, 13%, 14%, 15%, 16%, or about 17% HSA. In some embodiments, said composition comprises about 3.125% HSA. In some embodiments, said composition comprises about 5% HSA. In some embodiments, said composition comprises about 10% HSA. In some embodiments, said composition comprises about 16.875% HSA.

In other embodiments, said composition comprises bovine serum albumin (BSA)(e.g., about 1%, 2%, 3%, 4%, 5%, 6%, 7%, 8%, 9%, 10%, 11%, 12%, 13%, 14% or 15% BSA) or fetal bovine serum (FBS) (e.g., about 1%, 2%, 3%, 4%, 5%, 6%, 7%, 8%, 9%, 10%, 11%, 12%, 13%, 14% or 15% FBS) in addition to or instead of HSA.

In some embodiments, said composition comprises a cryoprotectant, e.g., DMSO, e.g., about 1% to about 15% DMSO. In some embodiments, said composition comprises about 1% to about 5% DMSO. In some embodiments, said composition comprises about 1% to about 15%, about 2.5% to about 15%, about 2.5% to about 10%, about 5% to about 15%, about 5% to about 10% or about 10% to about 15% DMSO. In some embodiments, said composition comprises about 1%, 2%, 3%, 4%, 5%, 6%, 7%, 8%, 9%, 10%, 11%, 12%, 13%, 14% or 15% DMSO. In a particular embodiment, the composition comprises about 5% DMSO.

In a specific embodiment, said cells have been cryopreserved and thawed. In another specific embodiment, said cells have been filtered through a 70 μM to 100 μM filter. In another specific embodiment, said composition comprises no visible cell clumps. In another specific embodiment, said composition comprises fewer than about 200 cell clumps per 10⁶ cells, wherein said cell clumps are visible only under a microscope, e.g., a light microscope.

In another specific embodiment, said composition comprises fewer than about 150 cell clumps per 10⁶ cells, wherein said cell clumps are visible only under a microscope, e.g., a light microscope. In another specific embodiment, said composition comprises fewer than about 100 cell clumps per 10⁶ cells, wherein said cell clumps are visible only under a microscope, e.g., a light microscope.

In a specific embodiment of any of the methods or compositions described herein, the cells are stem cells, for example, stem cells isolated from a human postpartum placenta that has been drained of blood. In certain embodiments, such cells have been expanded. In another specific embodiment of any of the above embodiments, the cells are adherent cells, that is, cells that adhere to a tissue culture surface, e.g., tissue culture plastic (either uncoated or coated with, e.g., fibronectin, laminin, or the like). Examples of adherent cells include, e.g., adherent placental stem cells, as described herein; bone marrow-derived mesenchymal stem cells, fibroblasts, or the like. In another embodiment, the cells are human cells.

In another embodiment, said cells are cells obtained from (e.g., isolated from) placental perfusate. In a more specific embodiment, said cells are nucleated cells, e.g., total nucleated cells, obtained from placental perfusate. In certain embodiments, the placenta from which total nucleated placental cells are obtained by perfusion is drained of blood and perfused to remove residual blood prior to perfusion to collect total nucleated placental cells. In certain other embodiments, the placenta from which total nucleated placental cells are obtained by perfusion is drained of blood but is not perfused to remove residual blood prior to perfusion to collect total nucleated placental cells. In certain other embodiments, the placenta from which total nucleated placental cells are obtained by perfusion is neither drained of blood nor perfused to remove residual blood prior to perfusion to collect total nucleated placental cells.

In another specific embodiment of the method, said cells are stem cells. In more specific embodiments, the stem cells are adult stem cells, somatic stem cells, embryonic stem cells, embryonic germ cells, umbilical cord stem cells, amniotic fluid stem cells, bone marrow-derived mesenchymal stem cells, cord blood-derived mesenchymal stem cells, peripheral blood-derived mesenchymal stem cells, adipose-derived mesenchymal stem cells or periosteum-derived mesenchymal stem cells. In another embodiment, said cells are natural killer cells.

In another specific embodiment, said cells are isolated placental cells. In certain embodiments, the isolated placental cells are isolated placental stem cells. In certain other embodiments, the isolated placental cells are isolated placental multipotent cells.

In certain embodiments, the isolated placental cells are isolated placental stem cells. In certain other embodiments, the isolated placental cells are isolated placental multipotent cells. In a specific embodiment, the isolated placental cells are CD34$^-$, CD10$^+$ and CD105$^+$ as detected by flow cytometry. In a more specific embodiment, the isolated CD34$^-$, CD10$^+$, CD105$^+$ placental cells are placental stem cells. In another more specific embodiment, the isolated CD34$^-$, CD 10$^+$, CD 105$^+$ placental cells are multipotent placental cells. In another specific embodiment, the isolated CD34$^-$, CD 10$^+$, CD 105$^+$ placental cells have the potential to differentiate into cells of a neural phenotype, cells of an osteogenic phenotype, or cells of a chondrogenic phenotype. In a more specific embodiment, the isolated CD34$^-$, CD10$^+$, CD105$^+$ placental cells are additionally CD200$^+$. In another more specific embodiment, the isolated CD34$^-$, CD10$^+$, CD105$^+$ placental cells are additionally CD90$^+$ or CD45$^-$, as detected by flow cytometry. In another more specific embodiment, the isolated CD34$^-$, CD10$^+$, CD105$^+$ placental cells are additionally CD90$^+$ or CD45$^-$, as detected by flow cytometry. In a more specific embodiment, the CD34$^-$, CD10$^+$, CD105$^+$, CD200$^+$ placental cells are additionally CD90$^+$ or CD45$^-$, as detected by flow cytometry. In another more specific embodiment, the CD34$^-$, CD10$^+$, CD105$^+$, CD200$^+$ cells are additionally CD90$^+$ and CD45$^-$, as detected by flow cytometry. In another more specific embodiment, the CD34$^-$, CD10$^+$, CD105$^+$, CD200$^+$, CD90$^+$, CD45$^-$ cells are additionally CD80$^-$ and CD86$^-$, as detected by flow cytometry.

In a more specific embodiment, the CD34$^-$, CD10$^+$, CD105$^+$ cells are additionally one or more of CD29$^+$, CD38$^-$, CD44$^+$, CD54$^+$, CD80$^-$, CD86$^-$, SH3$^+$ or SH4$^+$. In another more specific embodiment, the cells are additionally CD44$^+$. In a specific embodiment of any of the isolated CD34$^-$, CD10$^+$, CD105$^+$ placental cells above, the cells are additionally one or more of CD117$^-$, CD133$^-$, KDR$^-$ (VEGFR2$^-$), HLA-A,B,C$^+$, HLA-DP,DQ,DR$^-$, and/or Programmed Death-1 Ligand (PDL1)$^+$.

In other embodiments, the isolated placental cells are CD200+ and HLA-G$^+$; CD73$^+$, CD105$^+$, and CD200$^+$; CD200$^+$ and OCT-4$^+$; CD73$^+$, CD105$^+$ and HLA-G$^+$; CD73$^+$ and CD105$^+$ and facilitate the formation of one or more embryoid-like bodies in a population of placental cells comprising said isolated placental cells when said population is cultured under conditions that allow the formation of an embryoid-like body; or OCT-4$^+$ and facilitate the formation of one or more embryoid-like bodies in a population of placental cells comprising the isolated placental cells when said population is cultured under conditions that allow formation of embryoid-like bodies; or any combination thereof. In a specific embodiment, said CD200$^+$, HLA-G$^+$ placental cells are CD34$^-$, CD38$^-$, CD45$^-$, CD73$^+$ and CD105$^+$. In another specific embodiment, said CD73$^+$, CD105$^+$, and CD200$^+$ placental cells are CD34$^-$, CD38$^-$, CD45$^-$, and HLA-G$^+$. In another specific embodiment, said CD200$^+$, OCT-4$^+$ placental cells are CD34$^-$, CD38$^-$, CD45$^-$, CD73$^+$, CD105$^+$ and HLA-G$^+$. In another specific embodiment, said CD73$^+$, CD105$^+$ and HLA-G+placental cells are CD34$^-$, CD45$^-$, OCT-4$^+$ and CD200$^+$. In another specific embodiment, said CD73$^+$ and CD105$^+$ placental cells are OCT-4$^+$, CD34$^-$, CD38$^-$ and CD45$^-$. In another specific embodiment, said placental cells are CD73$^+$, CD105$^+$, CD200$^+$, CD34$^-$, CD38$^-$, and CD45$^-$.

In certain embodiments, the isolated placental cells are one or more of CD10$^+$, CD29$^+$, CD34$^-$, CD38$^-$, CD44$^+$, CD45$^-$, CD54$^+$, CD80$^-$, CD86$^-$, CD90$^+$, CD117$^-$, CD133$^-$, CD200$^+$, SH2$^+$, SH3$^+$, SH4$^+$, SSEA3$^-$, SSEA4$^-$, OCT-4$^+$, MHC-I$^+$, KDR$^-$ (VEGFR2$^-$), HLA-A,B,C$^+$, HLA-DP,DQ, DR$^-$, PDL1$^+$ or ABC-p$^+$, where ABC-p is a placenta-specific ABC transporter protein (also known as breast cancer resistance protein (BCRP) and as mitoxantrone resistance protein (MXR)). In a specific embodiment, the isolated placental cells are CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$-$, SSEA4$^-$, and OCT-4$^+$. In another embodiment, the isolated placental cells are CD10$^+$, CD29$^+$, CD34$^-$, CD38$^-$, CD45$^-$, CD54$^+$, SH2$^+$, SH3$^+$, and SH4$^+$. In another embodiment, the isolated placental cells are CD10$^+$, CD29$^+$, CD34$^-$, CD38$^-$, CD45$^-$, CD54$^+$, SH2$^+$, SH3$^+$, SH4$^+$ and OCT-4$^+$. In another embodiment, the isolated placental cells are CD10$^+$, CD29$^+$, CD34$^-$, CD38$^-$, CD44$^+$, CD45$^-$, CD54$^+$, CD90$^+$, HLA-1$^+$, SH2$^+$, SH3$^+$, SH4$^+$. In another embodiment, the isolated placental cells are OCT-4$^+$ and ABC-p$^+$. In another embodiment, the isolated placental cells are SH2$^+$, SH3$^+$, SH4$^+$ and OCT-4$^+$. In another embodiment, the isolated placental cells are OCT-4$^+$, CD34$^-$, SSEA3$^-$, and SSEA4$^-$. In a specific embodiment, said OCT-4$^+$, CD34$^-$, SSEA3$^-$, and SSEA4$^-$ cells are additionally CD10$^+$, CD29$^+$, CD34$^-$, CD44$^+$, CD45$^-$, CD54$^+$, CD90$^+$, SH2$^+$, SH3$^+$, and SH4$^+$. In another embodiment, the isolated placental cells are OCT-4$^+$ and CD34$^-$, and either SH3$^+$ or SH4$^+$. In another embodiment, the isolated placental cells are CD34$^-$ and either CD10$^+$, CD29$^+$, CD44$^+$, CD54$^+$, CD90$^+$, or OCT-4$^+$. In certain embodiments, the isolated placental cells are CD10$^+$, CD34$^-$, CD105$^+$ and CD200$^+$.

In another embodiment, the isolated placental cells useful in the methods of treatment described herein are one or more of CD10$^+$, CD29$^-$, CD44$^+$, CD45$^-$, CD54/ICAM$^-$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a specific embodiment, the isolated placental cells are at least CD29$^-$ and CD54$^-$. In another specific embodiment, the isolated placental cells are at least CD44$^+$ and CD106$^+$. In another specific embodiment, the isolated placental cells are at least CD29$^+$.

In another specific embodiment, said isolated placental cells express one or more genes at a detectably higher level than an equivalent number of bone marrow-derived mesenchymal stem cells, wherein said one or more genes are one or more of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN$^2$, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow-derived mesenchymal stem cells have undergone a number of passages in culture equivalent to the number of passages said isolated placental cells have undergone. In a more specific embodiment, said isolated placental cells express said one or more genes when cultured for about 3 to about 35 population doublings in a medium comprising 60% Dulbecco's Modified Eagle's Medium (DMEM)-LG (preferably from Gibco) and 40% MCDB-201 (preferably from Sigma); 2% fetal calf serum (preferably from Hyclone Labs.); 1× insulin-transferrin-selenium (ITS); 1× linoleic acid-bovine serum albumin (LA-BSA); 10$^{-9}$ M dexamethasone (preferably from Sigma); 10$^{-4}$ M ascorbic acid 2-phosphate (preferably from Sigma); epidermal growth factor 10 ng/mL (preferably from R&D Systems); and platelet-derived growth factor (PDGF-BB) 10 ng/mL (preferably from R&D Systems). In a more specific embodiment, said isolated placental cells express said one or more genes when cultured for from about 3 to about 35 population doublings in a medium comprising 60% DMEM-LG (preferably from Gibco) and 40% MCDB-201 (preferably from Sigma); 2% fetal calf serum (preferably from Hyclone Labs.); 1× insulin-transferrin-selenium (ITS); 1× linoleic acid-bovine serum albumin (LA-BSA); $10^{-9}$ M dexamethasone (preferably from Sigma); $10^{-4}$ M ascorbic acid 2-phosphate (preferably from Sigma); epidermal growth factor 10 ng/mL (preferably from R&D Systems); and platelet-derived growth factor (PDGF-BB) 10 ng/mL (preferably from R&D Systems).

In another specific embodiment, said placental stem cells express the neurotrophic growth factors glial cell derived neurotrophic factor (GDNF), brain-derived neurotrophic factor (BDNF), hepatocyte growth factor (HGF), placental growth factor (PGF) and vascular endothelial growth factor (VEGF).

In another specific embodiment, said isolated placental cells are contained within a population of cells, at least 50% of the cells of which are said isolated placental cells. In another specific embodiment, said isolated placental cells are contained within a population of cells, at least 70% of the cells of which are said isolated placental cells. In another specific embodiment, said isolated placental cells are contained within a population of cells, at least 80% of the cells of which are said isolated placental cells. In another specific embodiment, said isolated placental cells are contained within a population of cells, at least 90% of the cells of which are said isolated placental cells. In certain other embodiments, the placental cells in said population of cells are substantially free of cells having a maternal genotype; e.g., at least 40%, 45%, 50%, 55%, 60%, 65%, 70%, 75%, 80%, 85%, 90%, 95%, 98% or 99% of the placental cells in said population have a fetal genotype, i.e., are fetal in origin. In certain other embodiments, the population of cells comprising said placental cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype, i.e., are fetal in origin.

In certain embodiments, the isolated placental cells are CD34$^+$ placental cells, e.g., hematopoietic placental cells. Such cells are obtainable from placental tissue, e.g., from a placenta that has been drained of cord blood and perfused to remove residual blood. In certain embodiments, the CD34$^+$ placental cells are CD38$^+$. In certain embodiments, the CD34$^+$ placental cells are CD38$^-$. In certain other embodiments, the CD34$^+$ placental cells are CD45$^+$. In a specific embodiment, the placental cells are CD34$^+$, CD38$^-$ and CD45$^+$.

In any of the above embodiments of isolated placental cells, the isolated placental cells generally do not differentiate during culturing in growth medium, i.e., medium formulated to promote proliferation, e.g., during proliferation in growth medium. In another specific embodiment, said isolated placental cells do not require a feeder layer in order to proliferate. In another specific embodiment, said isolated placental cells do not differentiate in culture as the result of culture in the absence of a feeder cell layer.

In another more specific embodiment, said isolated placental cells are obtained by perfusion of a post-partum placenta that has been drained of blood and perfused to remove residual blood; drained of blood but not perfused to remove residual blood; or neither drained of blood nor perfused to remove residual blood. In another more specific embodiment, said isolated placental cells are obtained by physical and/or enzymatic disruption of placental tissue.

In certain embodiments of the above method, isolated placental cells are filtered and cryopreserved as part of the construction of a placental cell bank. For example, isolated placental cells are isolated from a placenta, or placental tissue, and, after culturing, are resuspended in a solution comprising, e.g., dextran, e.g., dextran 40, e.g., 5.5% dextran 40. In more specific embodiments, the solution additionally comprises HSA and/or DMSO, in preparation for cryopreservation. Cryopreserved isolated placental cells in the bank are, as needed, thawed and diluted with, e.g., a solution comprising 10% dextran 40 as described herein. In certain embodiments of the method, the filtration and dilution method described herein is not a part of the initial isolation of isolated placental cells.

In certain embodiments, said isolated placental cells are obtained by perfusion of a post-partum placenta that has been drained of blood and perfused to remove residual blood. In another more specific embodiment, said isolated placental cells are obtained by physical and/or enzymatic disruption of placental tissue.

4. BRIEF DESCRIPTION OF THE FIGURES

FIG. 1 presents a ternary diagram depicting solution space of HSA, Dextran 40 and DMSO and experimental design for assessing the effect of varying component concentration on cell viability and proliferation.

Figure 2:
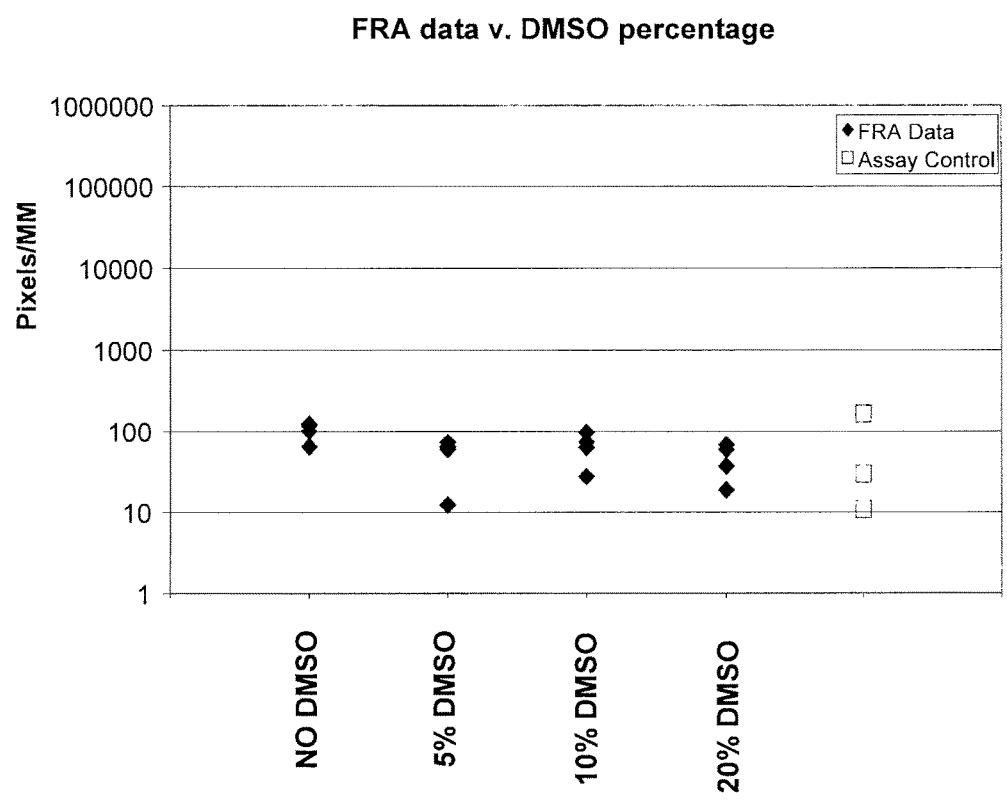

FIG. 2 presents Filter Retention Assay (FRA) data for formulations comprising different percentages of DMSO. Data are expressed in pixels per million cells loaded (px/MM) as read on a Vi-Cell cell viability analyzer. Assay control=100% dextran 40 solution, with cell stain, without cells.

Figure 3:
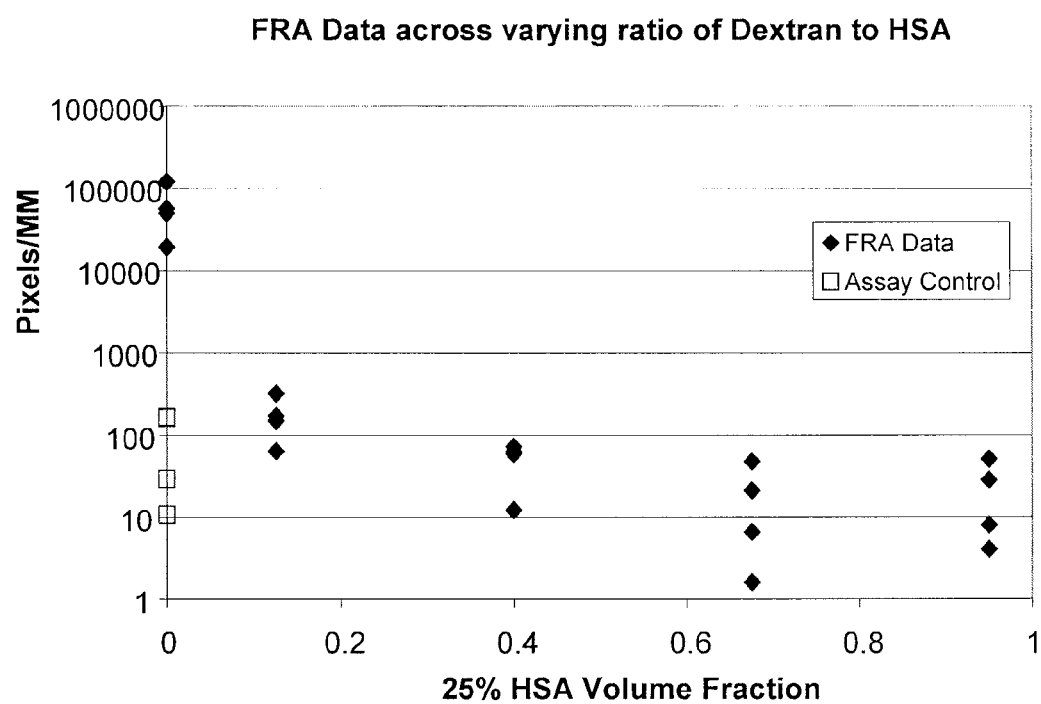

FIG. 3 presents FRA data for cell formulations comprising different volume fractions of HSA. Data are expressed in pixels per million cells loaded (px/MM) as read on a Vi-Cell cell viability analyzer. Assay control=100% dextran 40 solution, with cell stain, without cells.

Figure 4:
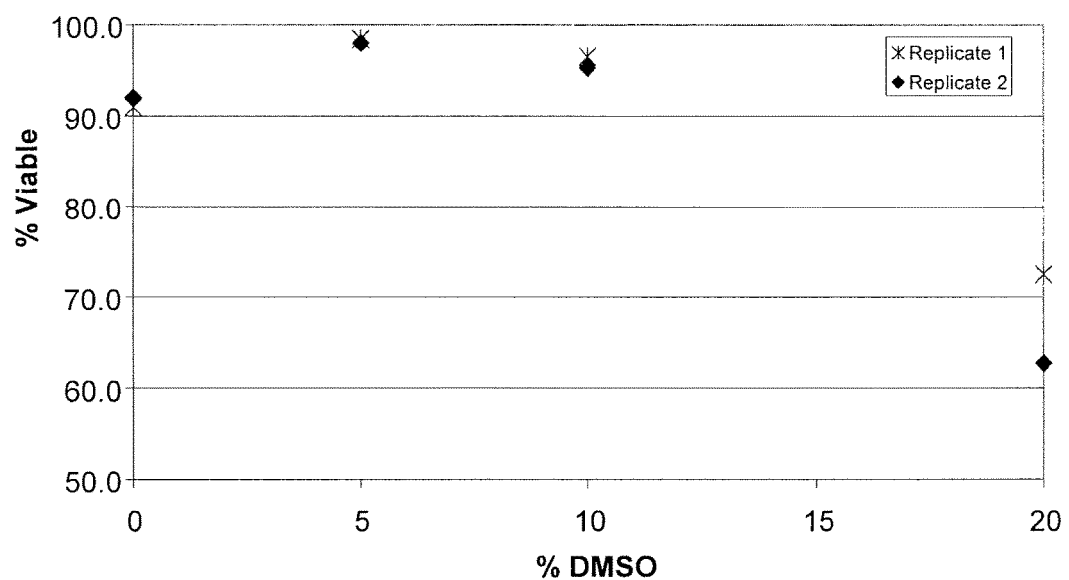

FIG. 4 presents post thaw trypan blue viability for cell formulations comprising different percentages of DMSO (0-20%).

Figure 5:
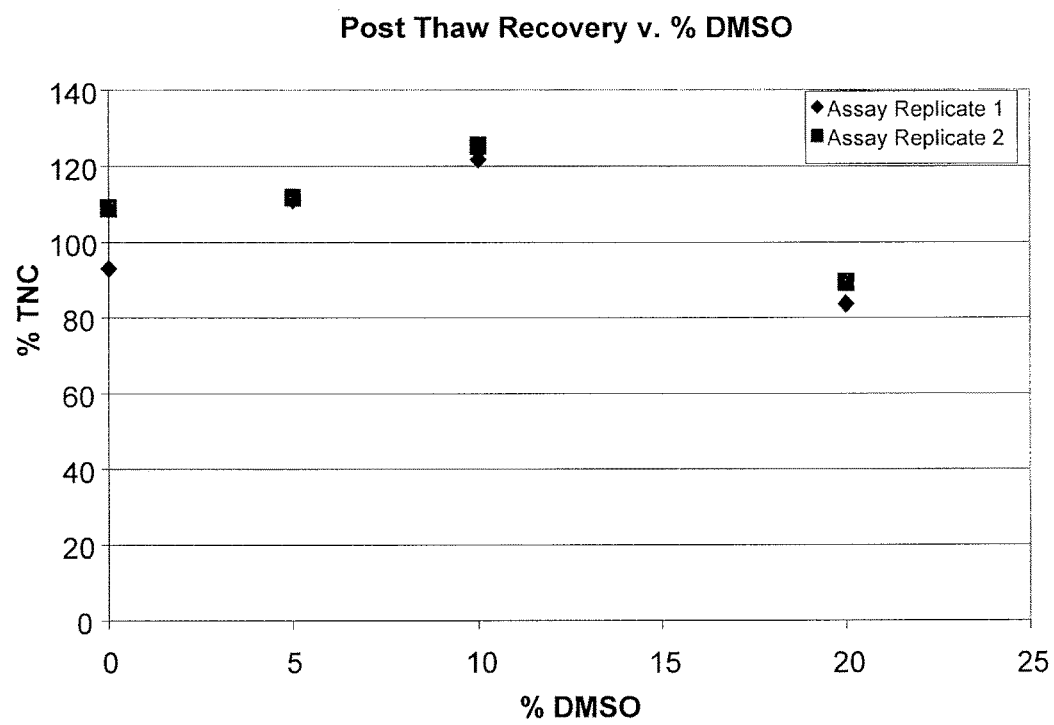

FIG. 5 presents post thaw total cell recovery as a function of varying concentrations of DMSO (0-20%).

Figure 6:
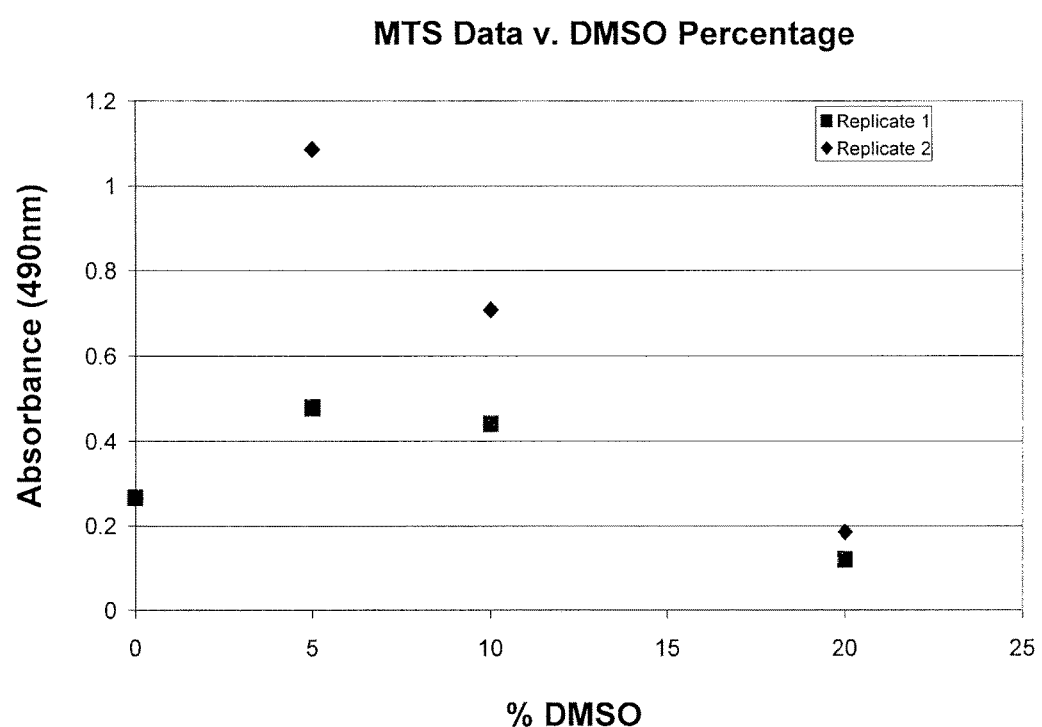

FIG. 6: Culture re-establishment as a function of varying formulations comprising different percentages of DMSO, as assessed by the MTS assay (see Section 6.3.1, below).

Figure 7:
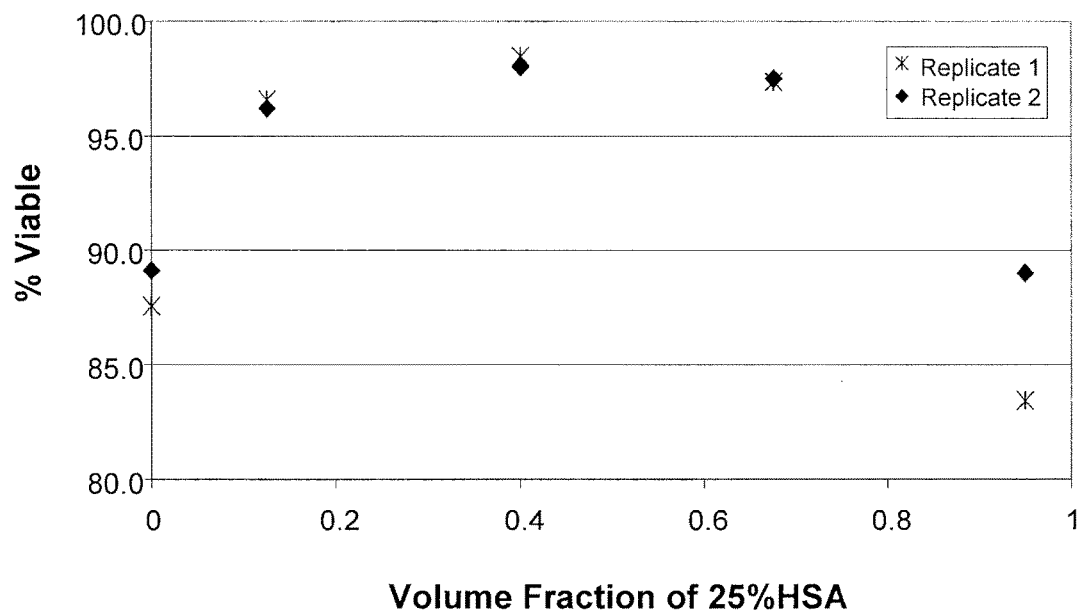

FIG. 7 presents post thaw cell viability of cell formulations comprising different volume fractions of 25% HSA.

Figure 8:
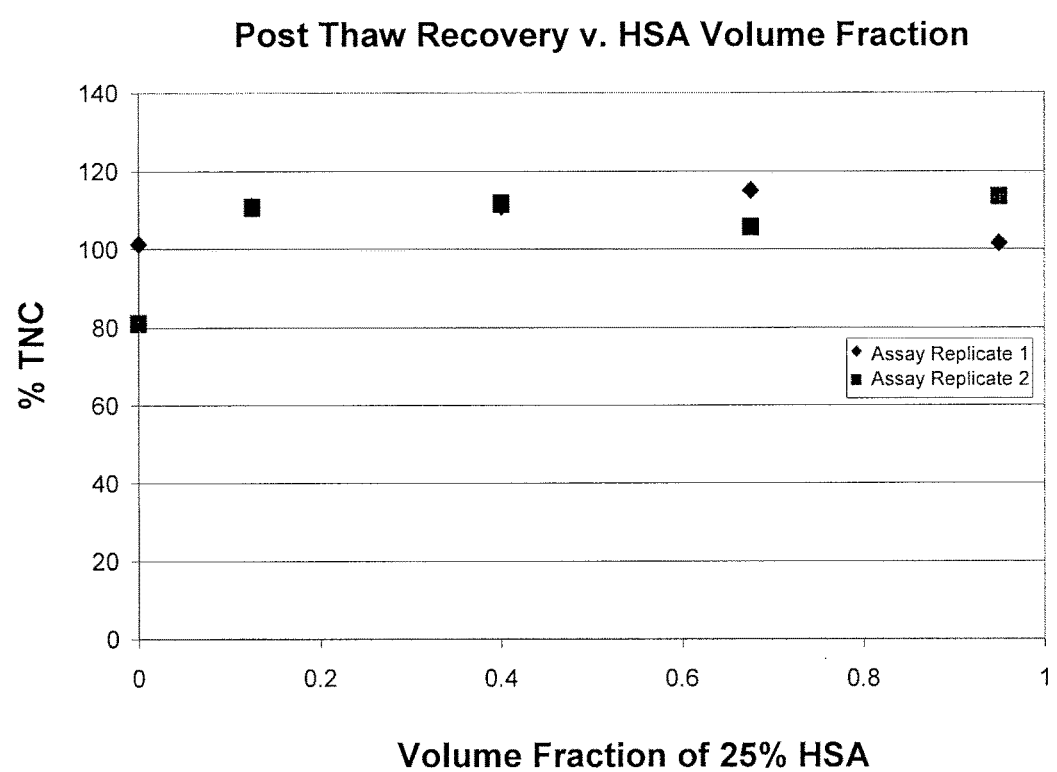

FIG. 8 presents post thaw total cell recovery as a function of HSA volume fraction.

Figure 9:
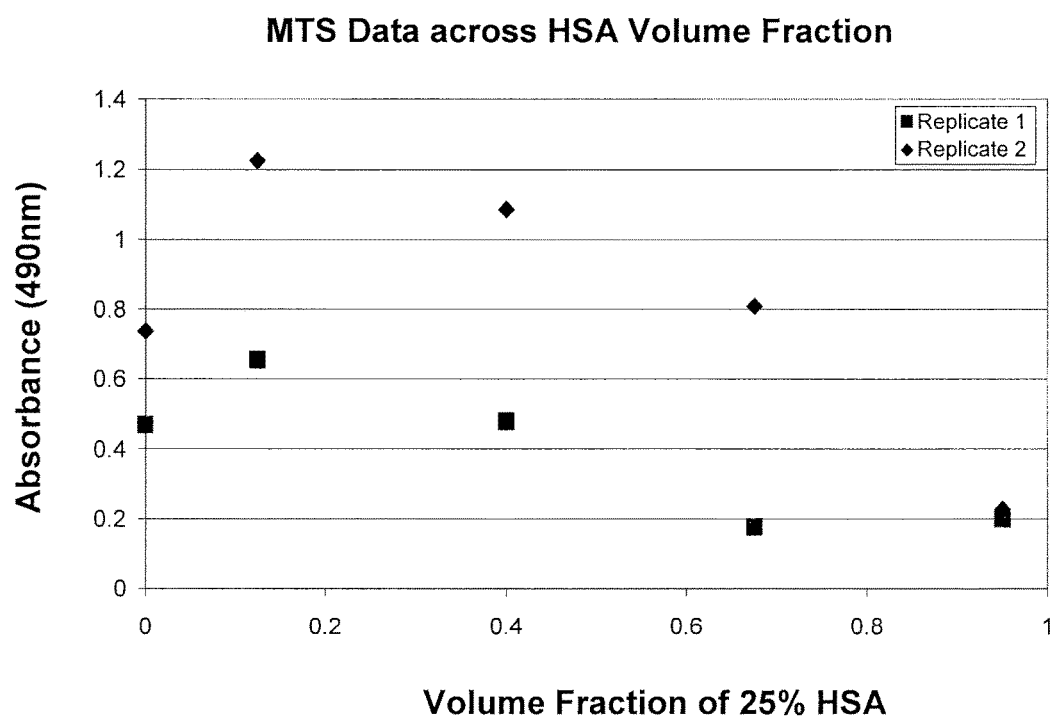

FIG. 9 presents data assessing culture re-establishment as a function of different fractions of HSA, generated through use of a Cell Titer 96® Aqueous Non-Radioactive Cell Proliferation Assay (Promega, Madison, Wis.).

Figure 10:
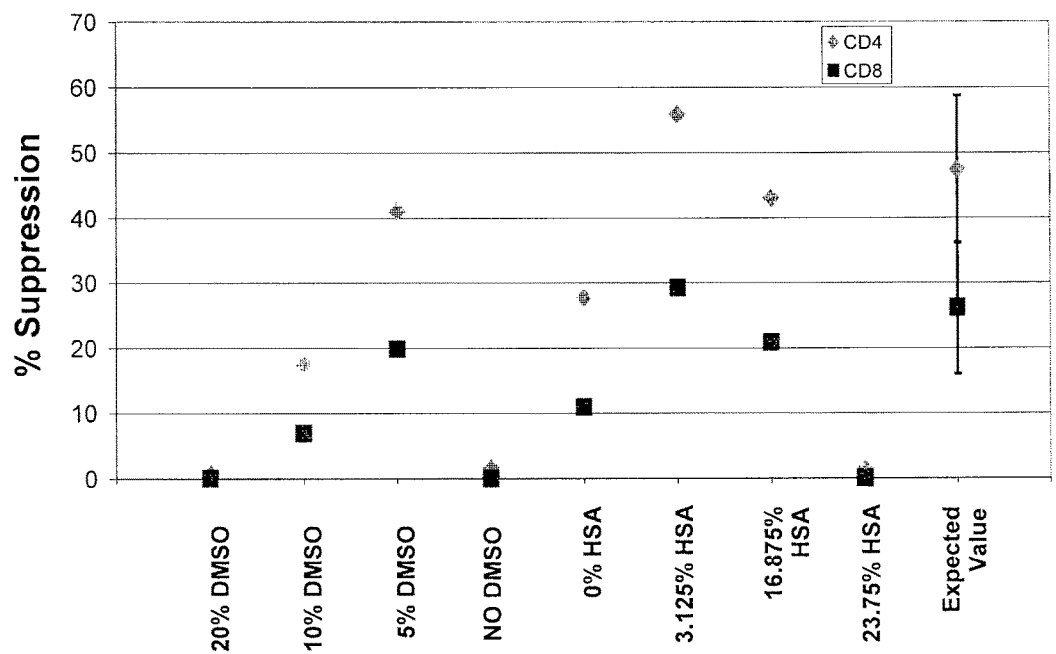

FIG. 10: Levels of immunosuppression as assessed by a Bead Reaction Assay for formulations comprising different concentrations of formulation components.

Figure 11:
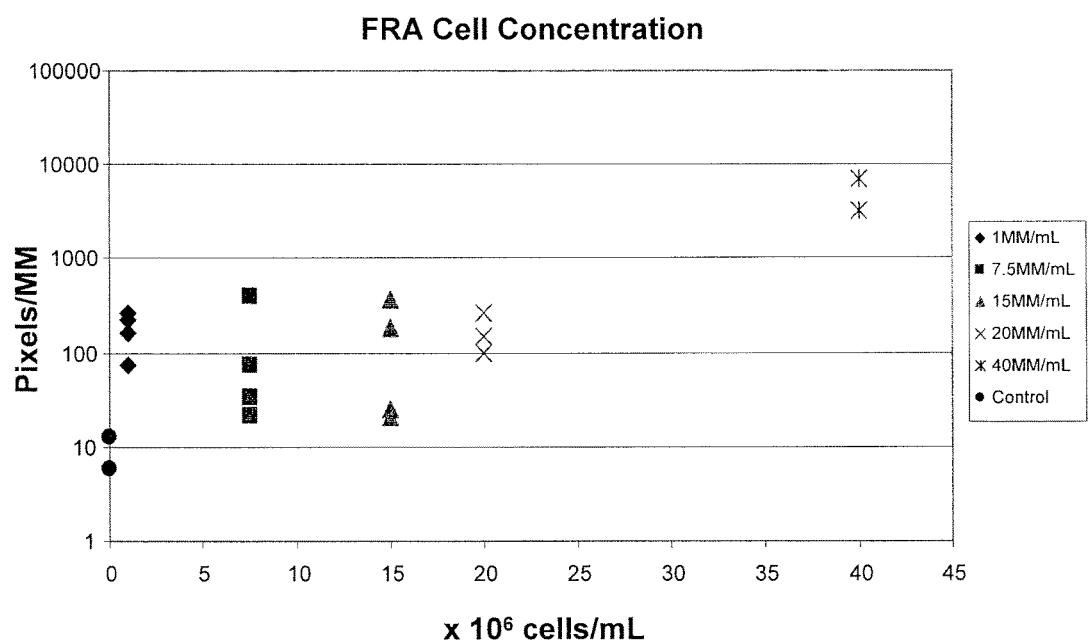

FIG. 11: Cellular aggregation as a function of varying freezing cell densities (1–40×10$^6$ cells/mL), as determined by FRA assay. Data are expressed in pixels per million cells loaded (px/MM) as read on a Vi-Cell cell viability analyzer.

Figure 12:
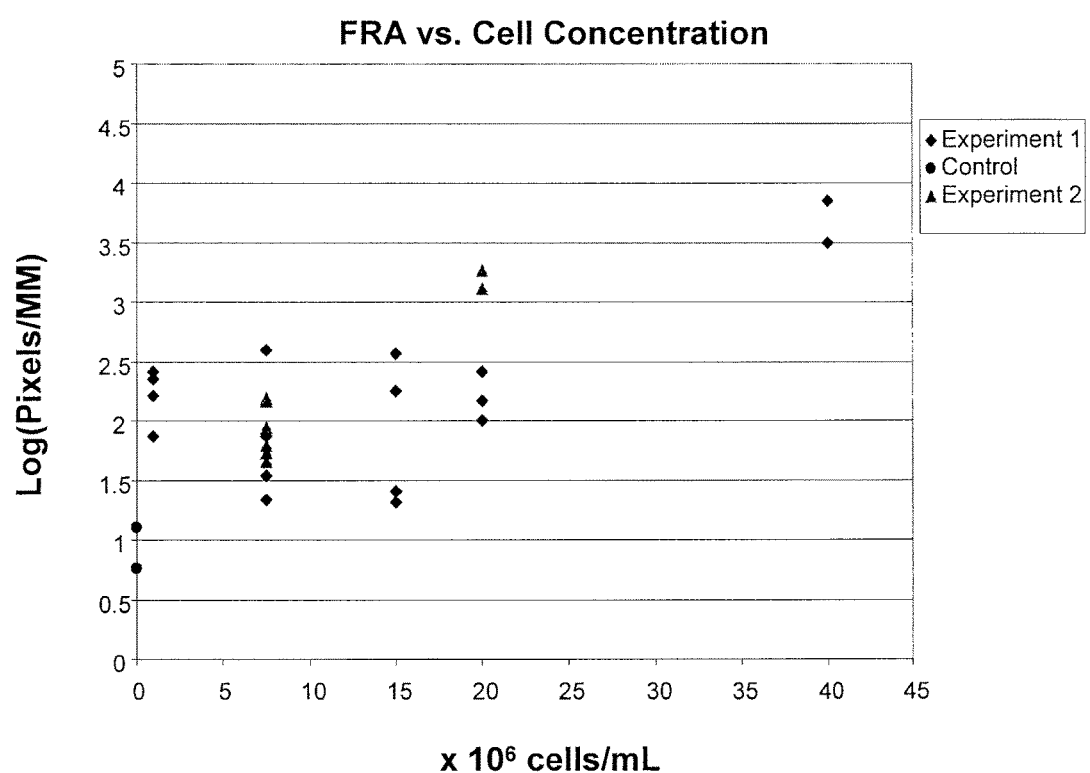

FIG. 12 Cellular aggregation as a function of freezing cell densities (1-40 million cells/mL). Data are expressed in pixels per million cells loaded (px/MM) as read on a Vi-Cell cell viability analyzer.

Figure 13:
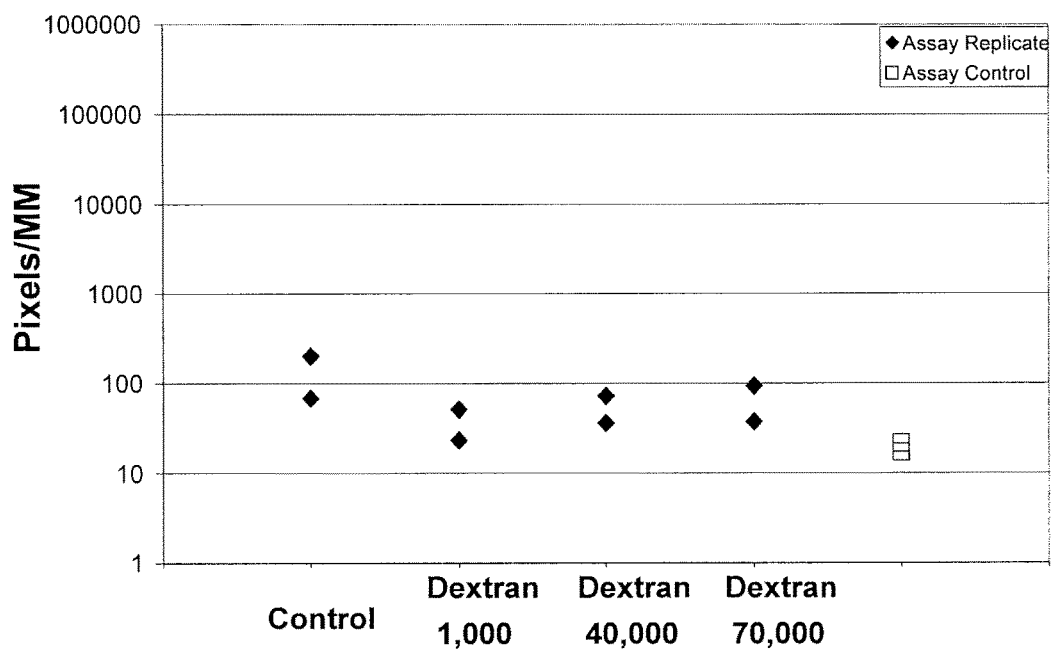

FIG. 13: Cellular aggregation as a function of varying molecular weights of dextran, as determined by FRA assay.

FRA signal equivalent across dextran 1,000, 40,000 and 70,000 (i.e., dextran 1, dextran 40 and dextran 70, respectively). Data are expressed in pixels per million cells loaded (px/MM). Assay control=100% dextran 40 solution, with cell stain, without cells.

Figure 14:
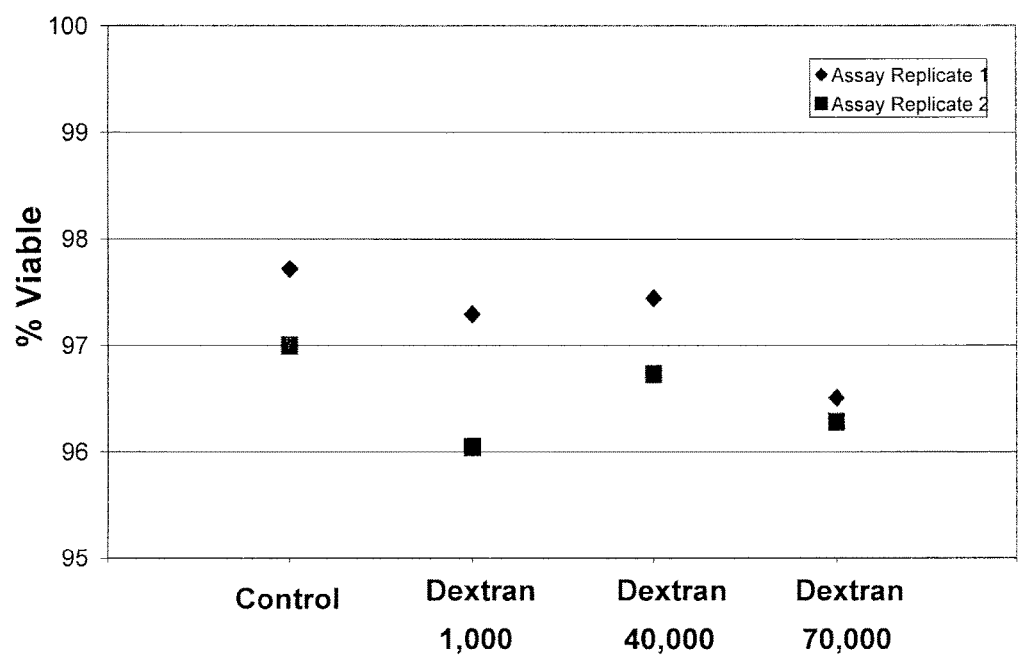

FIG. 14 presents post thaw viability across formulations comprising different molecular weights of dextran.

Figure 15:
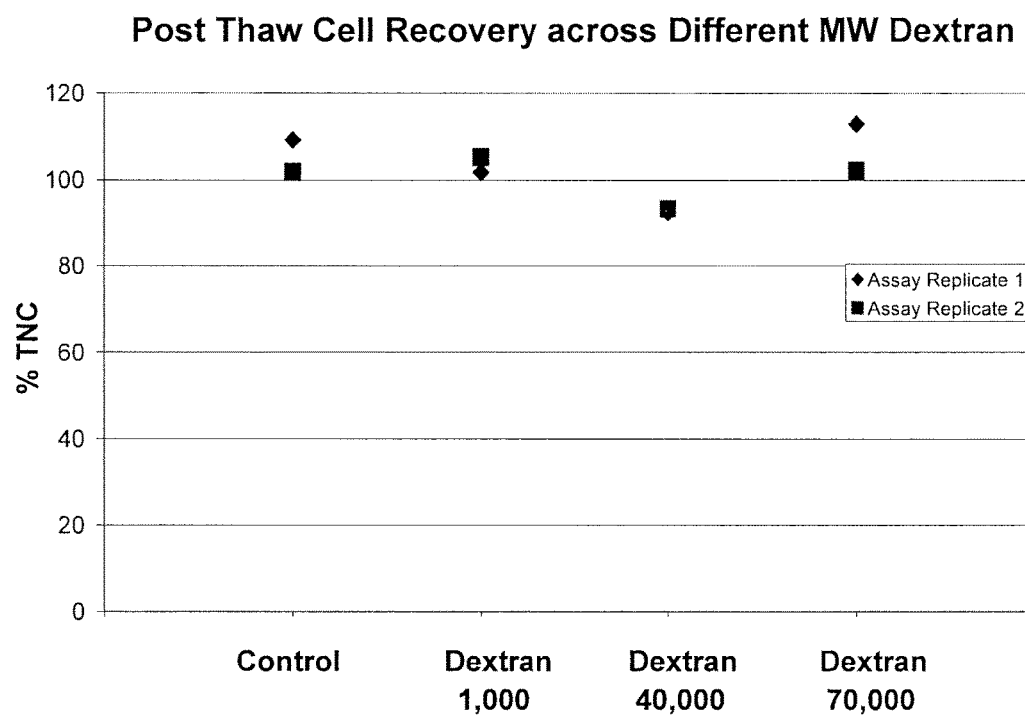

FIG. 15 presents cell recovery across formulations comprising different molecular weights of dextran.

Figure 16:
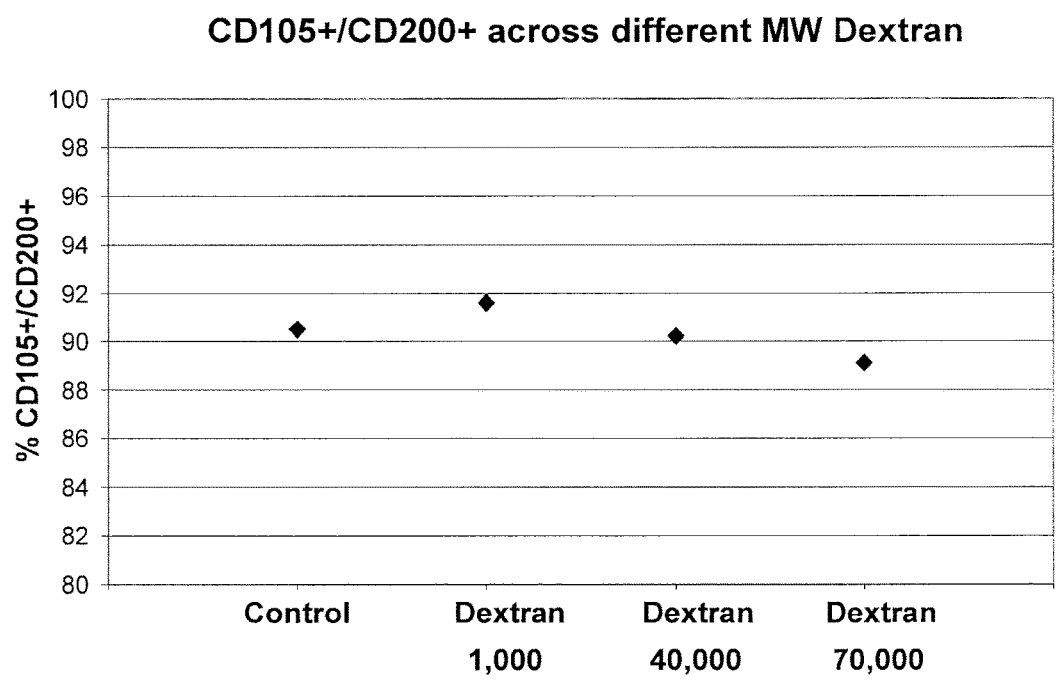

FIG. 16 presents $CD105^+/CD200^+$ across formulations comprising different molecular weights of dextran.

Figure 17:
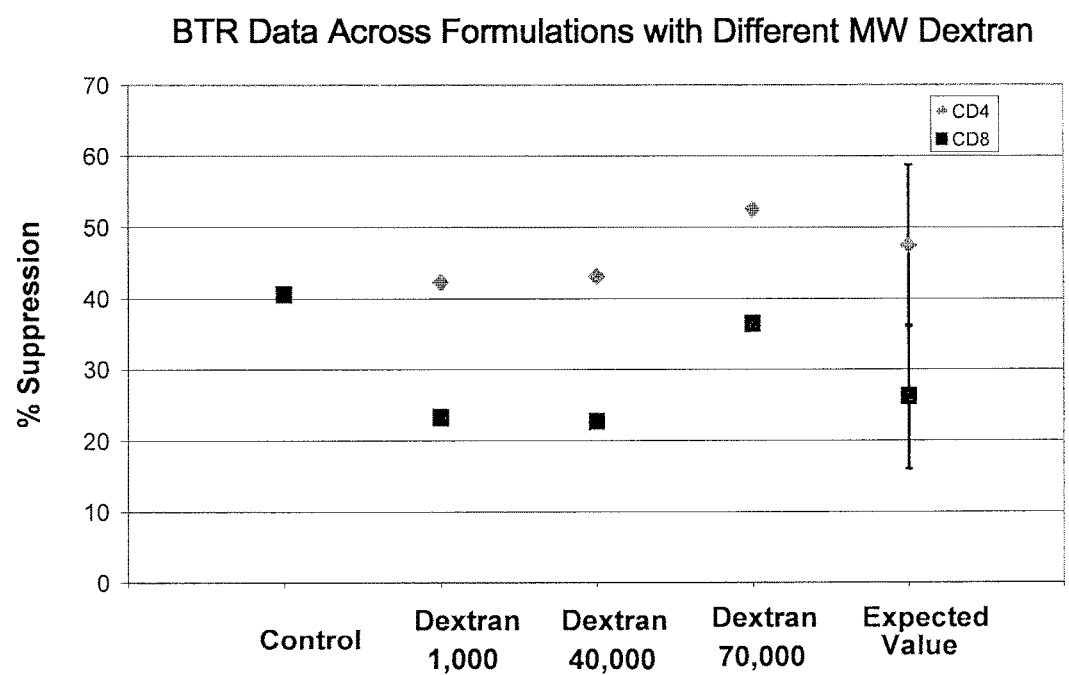

FIG. 17 presents bead T cell reaction (BTR) data across formulations comprising different molecular weights of dextran.

Figure 18:
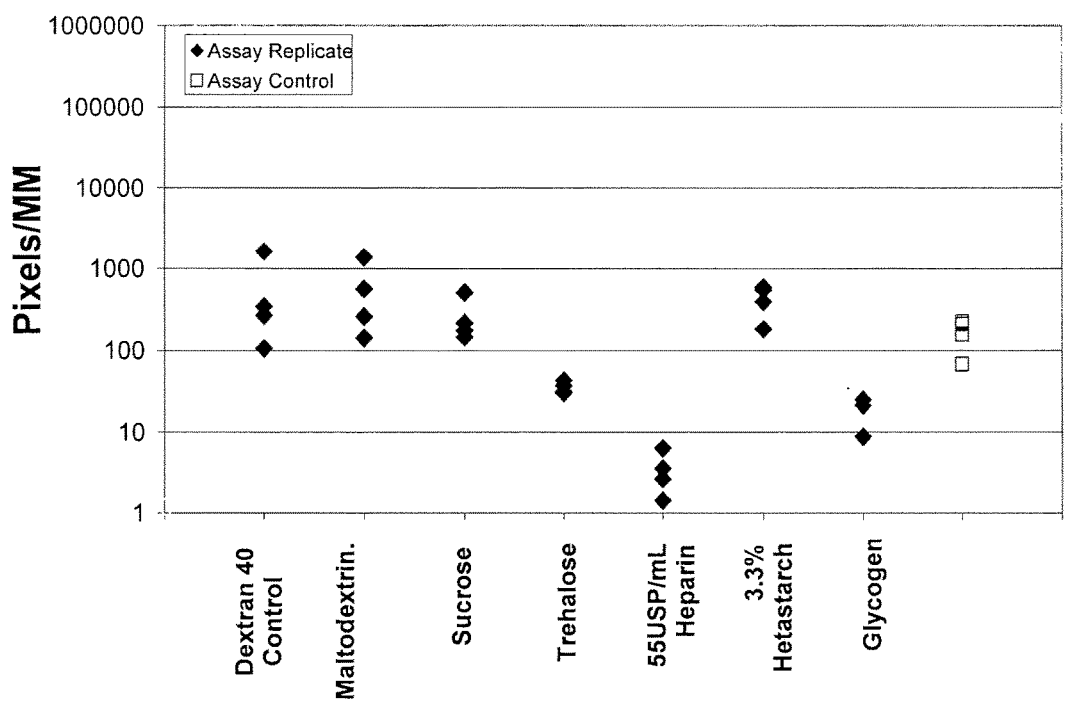

FIG. 18 presents cellular aggregation measured by FRA across formulations comprising different polysaccharides. Assay control=100% dextran 40 solution, with cell stain, without cells.

Figure 19:
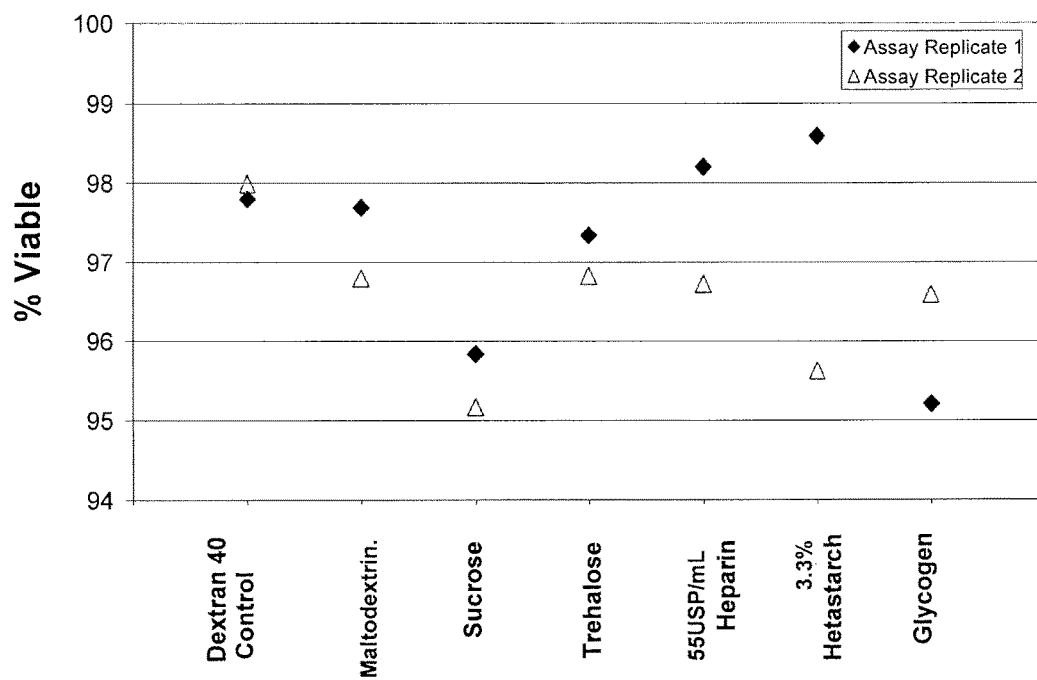

FIG. 19 presents post-thaw viability of cells formulated with non-dextran 40 polysaccharides. Data are expressed in pixels per million cells loaded (px/MM).

Figure 20:
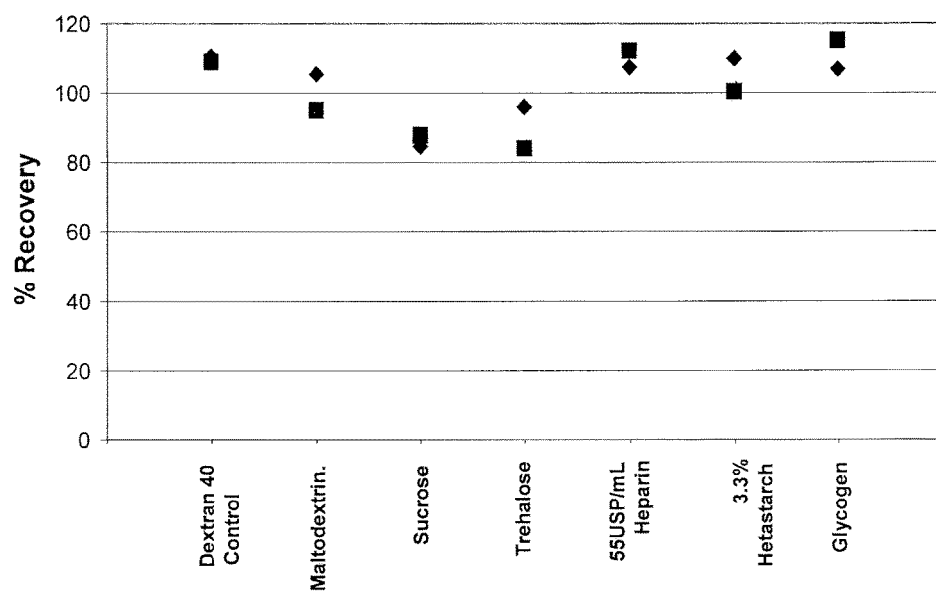

FIG. 20: Viable cell recovery as a function of formulations comprising different polysaccharides.

Figure 21:
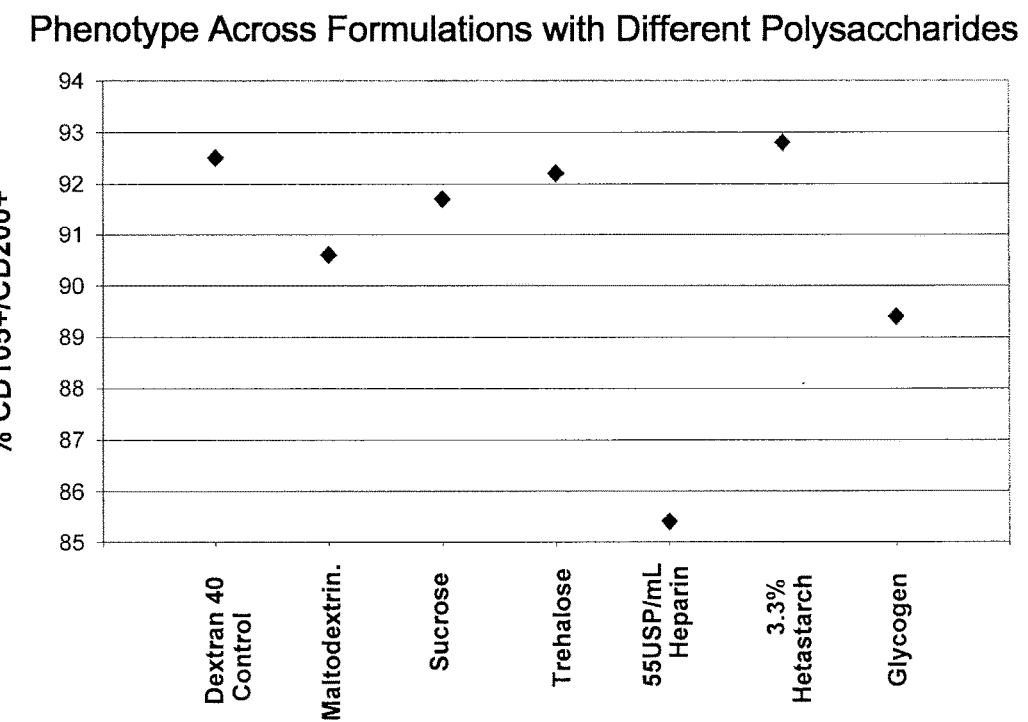

FIG. 21 presents $CD105^+/CD200^+$ expression in cell formulations comprising dextran 40, or maltodextrin, sucrose, trehalose, heparin, hetastarch or glycogen instead of dextran 40.

Figure 22:
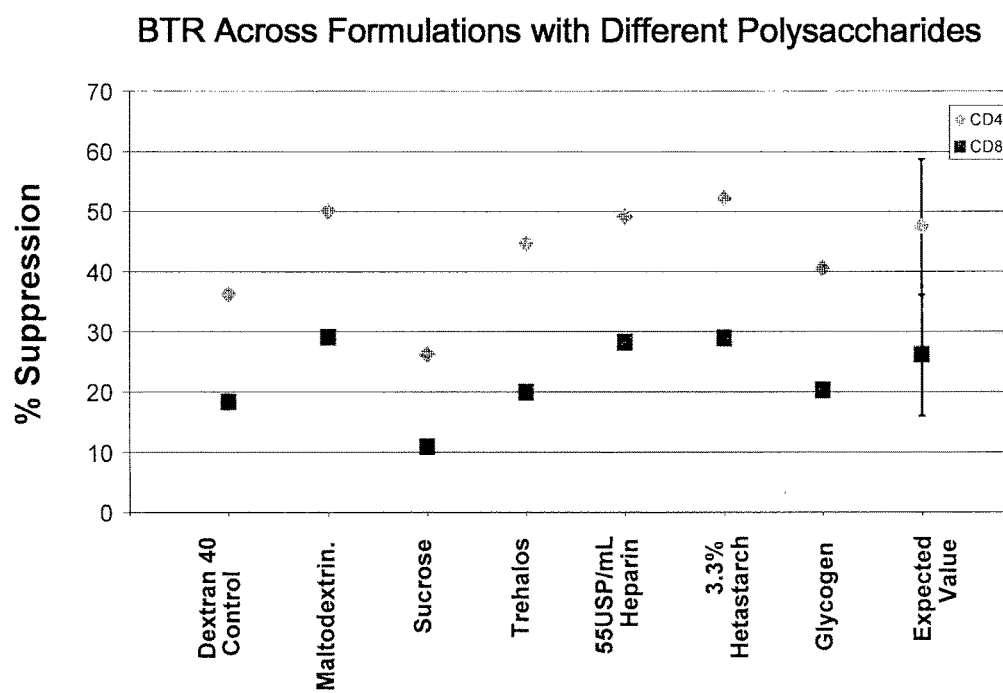

FIG. 22 presents BTR Data for dextran 40 and six non-dextran 40 different sugars/polysaccharides.

Figure 23:
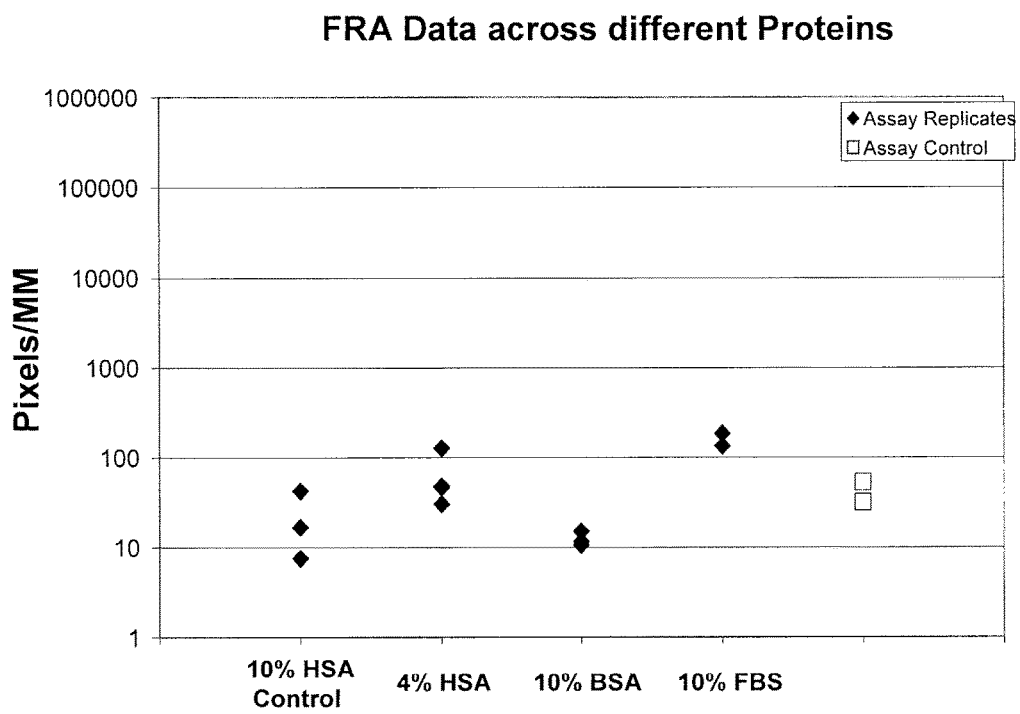

FIG. 23 presents cellular aggregation measured by FRA across formulations comprising 10% human serum albumin (HSA), 10% bovine serum albumin (BSA) or 10% fetal bovine serum (FBS). Assay control=100% dextran 40 solution, with cell stain, without cells.

Figure 24:
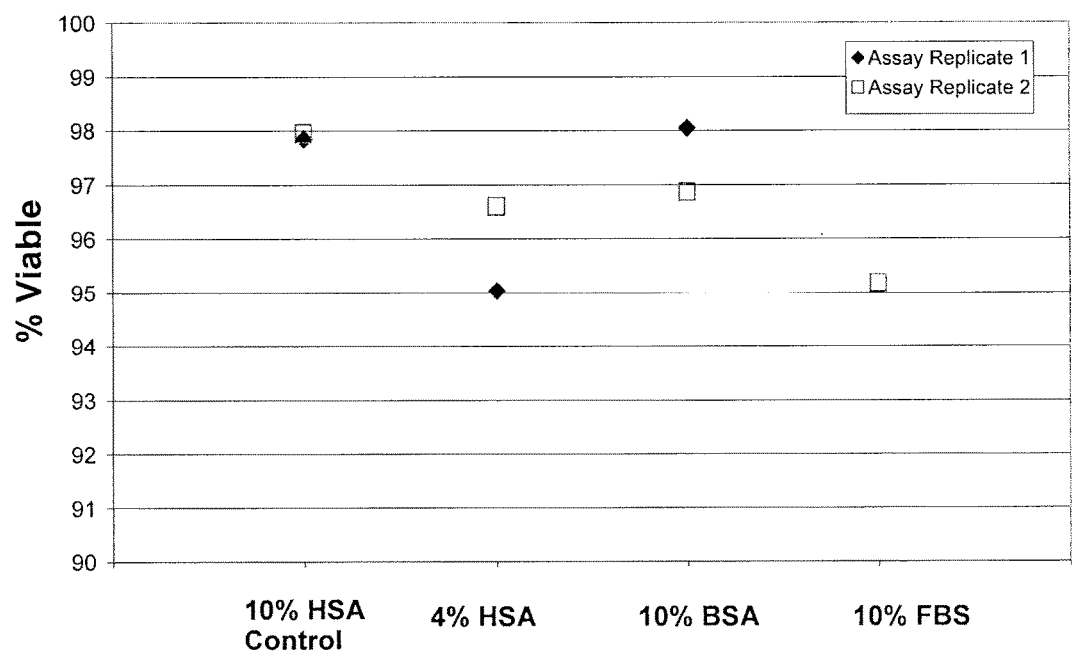

FIG. 24: Cellular post-thaw viability across formulations comprising 10% HSA, 10% BSA or 10% FBS.

Figure 25:
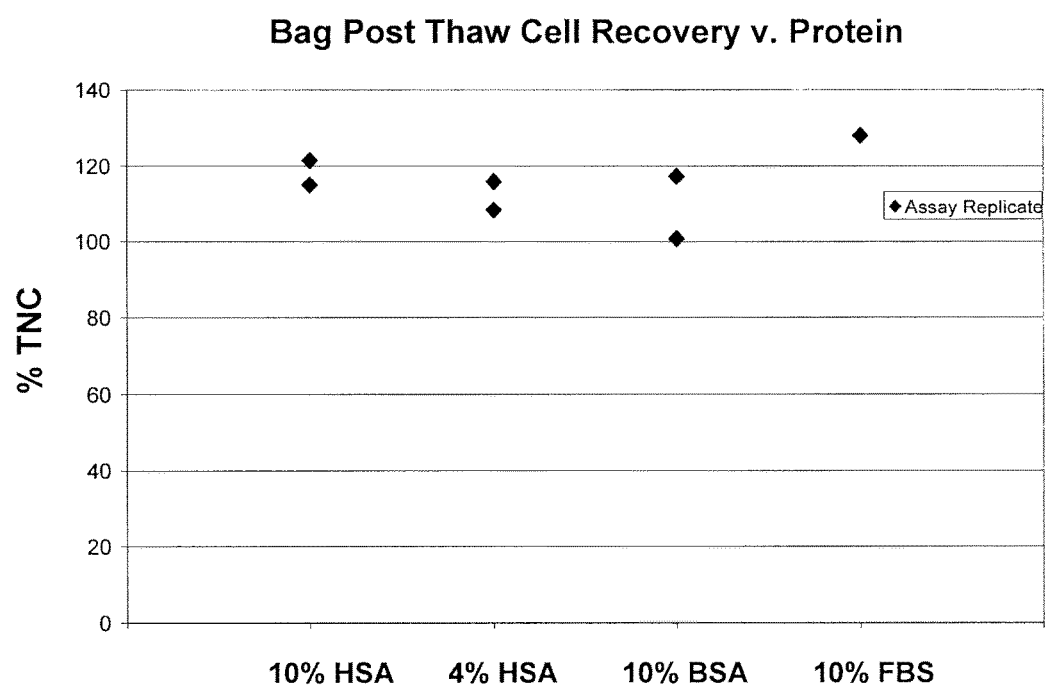

FIG. 25 presents post thaw recovery across formulations comprising 10% HSA, 4% HSA, 10% BSA or 10% FBS.

Figure 26:
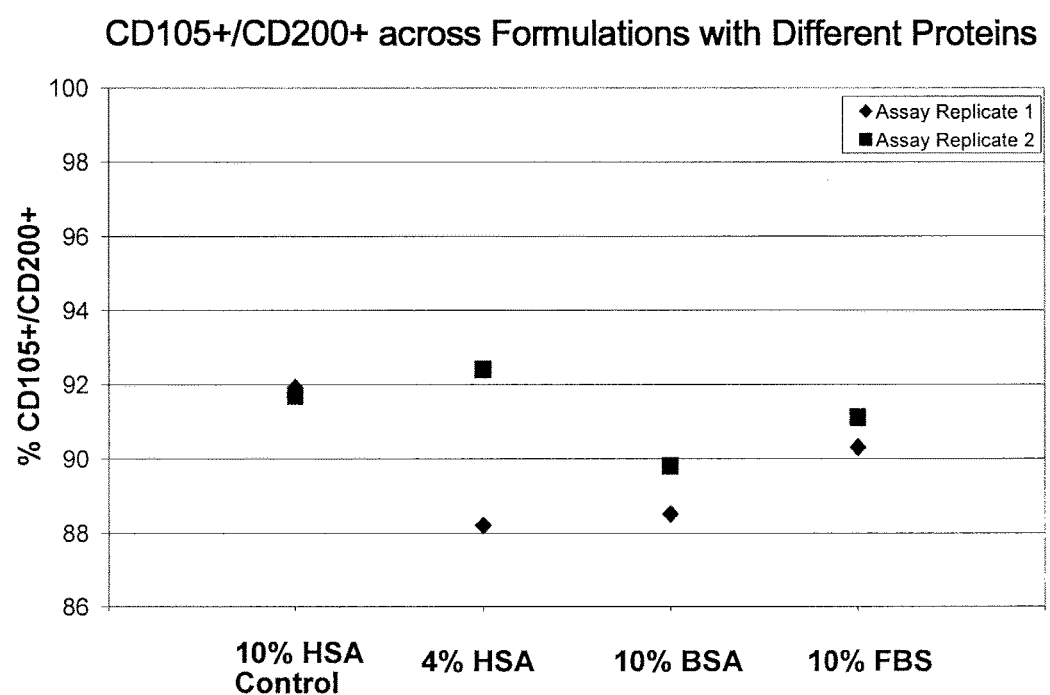

FIG. 26 presents cell identity measured by $CD105^+/CD200^+$ expression across formulations comprising 10% HSA, 4% HSA, 10% BSA or 10% FBS.

Figure 27:
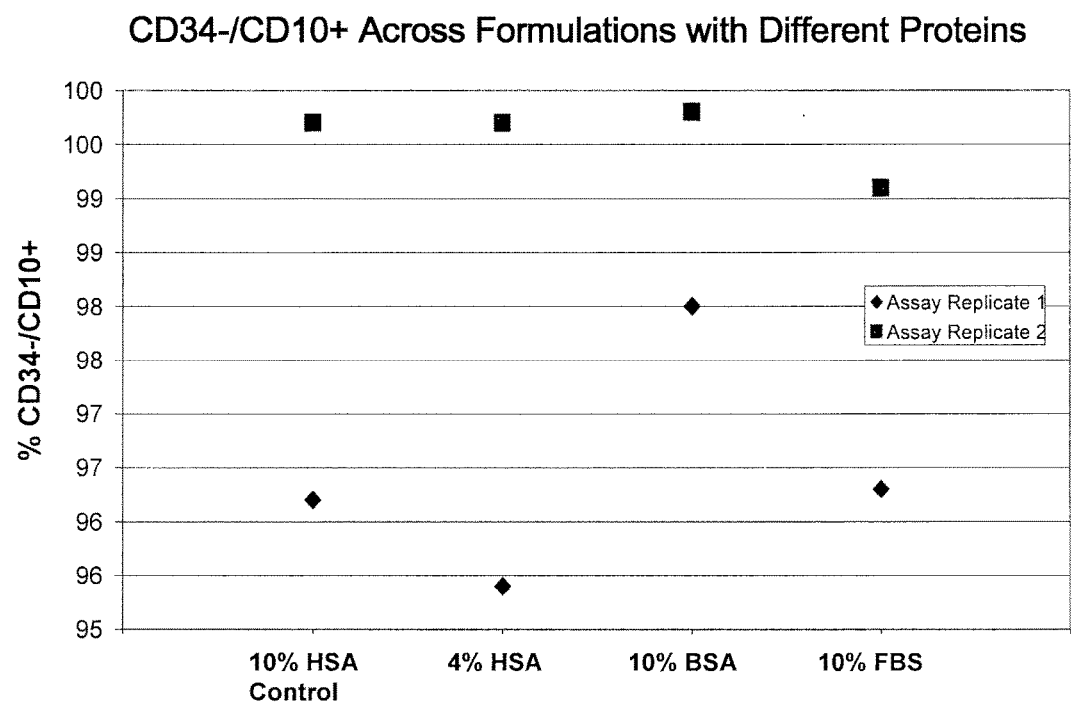

FIG. 27 presents CD34−/CD10+ expression across formulations comprising 10% HSA, 10% BSA or 10% FBS.

Figure 28:
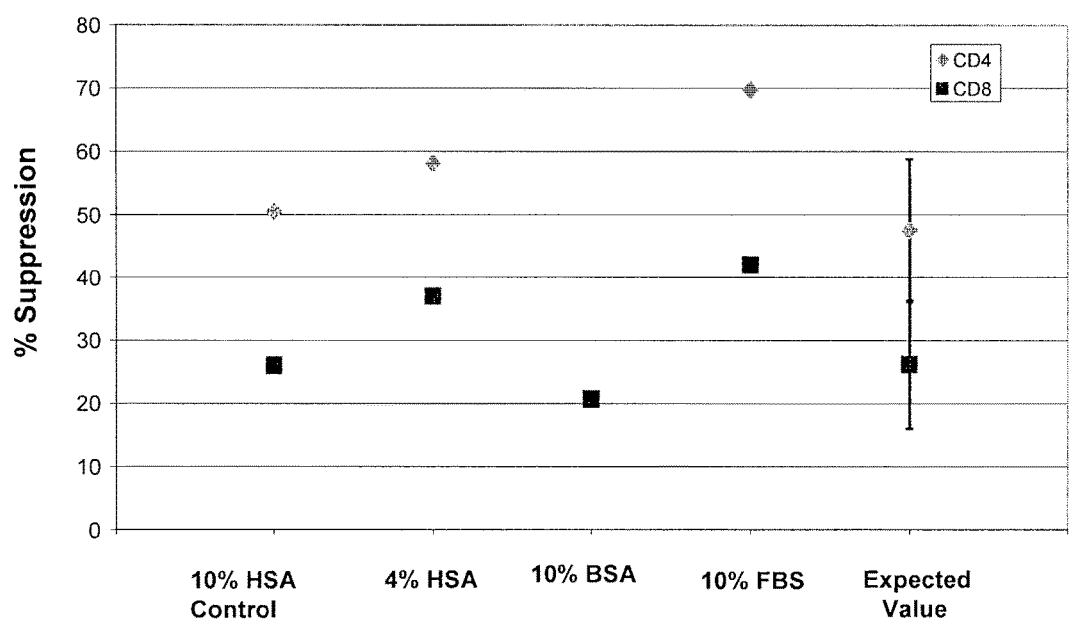

FIG. 28 presents cell functionality measured by the BTR assay across formulations comprising 10% HSA, 4% HSA, 10% BSA or 10% FBS.

Figure 29:
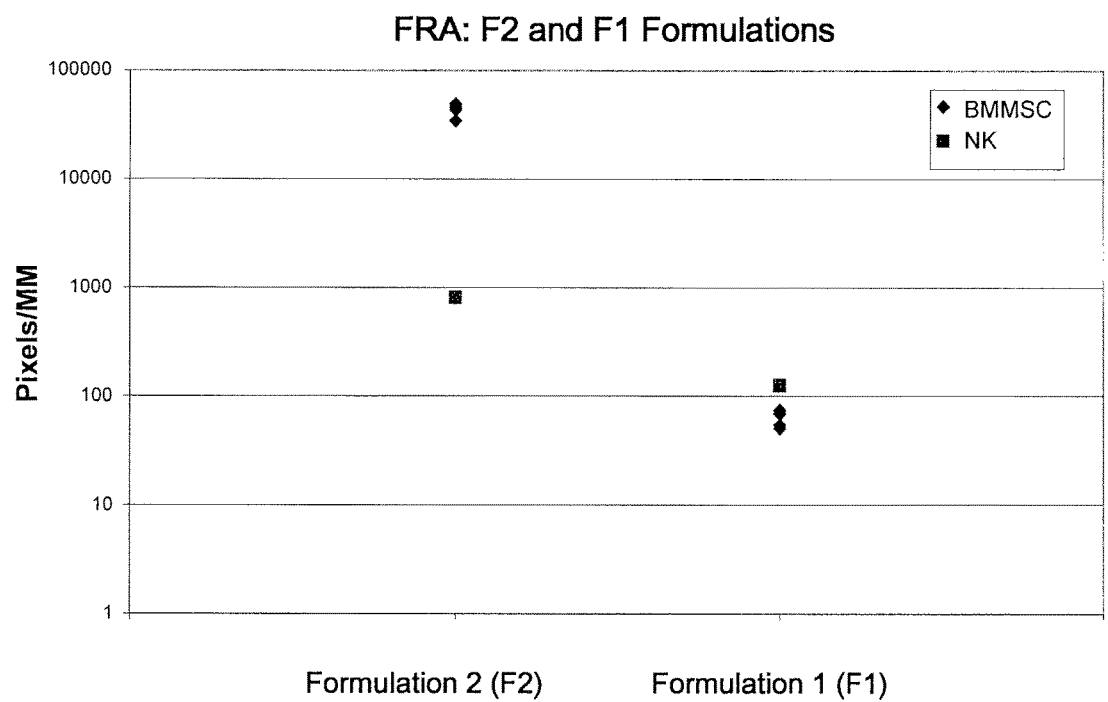

FIG. 29 presents FRA cellular aggregation results for bone marrow derived mesenchymal stem cells (BMMSC) cells and natural killer (NK) cells. Data are expressed in pixels per million cells loaded (px/MM).

5. DETAILED DESCRIPTION 5.1 Definitions

As used here, the term "about" means, e.g., within 10% of a stated figure or value.

As used herein, "macro cell clump" means an aggregation of cells visible without magnification, e.g., visible to the naked eye, and generally refers to a cell aggregation larger than about 150 microns.

As used herein, "micro cell clump" means a cell aggregation visible only with magnification, and generally refers to a cell aggregation smaller than about 150 microns.

As used herein, the term "SH2" refers to an antibody that binds an epitope on the marker CD105. Thus, cells that are referred to as $SH2^+$ are $CD105^+$.

As used herein, the terms "SH3" and $SH4^+$ refer to antibodies that bind epitopes present on the marker CD73. Thus, cells that are referred to as $SH3^+$ and/or $SH4^+$ are $CD73^+$.

As used herein, the term "isolated cell," e.g., "isolated stem cell," means a cell that is substantially separated from other cells of the tissue, e.g., placenta, from which the cell is derived. A cell is "isolated" if at least 50%, 60%, 70%, 80%, 90%, 95%, or at least 99% of the cells with which the cell is naturally associated, are removed from the cell, e.g., during collection and/or culture of the cell.

As used herein, "multipotent," when referring to a cell, means that the cell has the ability to differentiate into some, but not necessarily all, types of cells of the body, or into cells having characteristics of some, but not all, types of cells of the body. In certain embodiments, for example, an isolated multipotent cell that has the capacity to differentiate into either of cells having characteristics of chondrogenic or osteogenic cells is a multipotent cell.

As used herein, the term "population of isolated cells" means a population of cells that is substantially separated from other cells of a tissue, e.g., placenta, from which the population of cells is derived.

As used herein, the term "placental stem cell" refers to a stem cell or progenitor cell that is derived from a mammalian placenta, regardless of morphology, cell surface markers, or the number of passages after a primary culture. A placental stem cell is not obtained, and is not obtainable, from blood, e.g., cord blood or placental blood. The terms "placental stem cell" and "placental multipotent cell" as used herein do not, however, refer to, and placental stem cells and placental multipotent cells are not, trophoblasts, angioblasts, hemangioblasts, embryonic germ cells, embryonic stem cells, or cells obtained from the inner cell mass of a blastocyst, a cell obtained from an embryonic gonadal ridge, e.g., an embryonic germ cell. A cell is considered a "stem cell" if the cell displays attributes of a stem cell, e.g., a marker or gene expression profile associated with one or more types of stem cells; the ability to replicate at least 10-40 times in culture, the ability to differentiate into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord. The placental stem cells disclosed herein, in certain embodiments, differentiate in vitro (under differentiating conditions), differentiate in vivo, or both.

As used herein, a cell, e.g., a stem cell, is "positive" for a particular marker when that marker is detectable above background. For example, a placental stem cell is positive for, e.g., CD73 because CD73 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also refers to a cell exhibiting that marker in a amount that produces a signal, e.g., in a cytometer, that is detectably above background. For example, a cell is "CD200+" where the cell is detectably labeled with an antibody specific to CD200, and the signal from the antibody is detectably higher than that of a control (e.g., background or an isotype control). Conversely, "negative" in the same context means that the cell surface marker is not detectable using an antibody specific for that marker compared to background. For example, a cell is "CD34⁻" where the cell is reproducibly not detectably labeled with an antibody specific to CD34 to a greater degree than a control (e.g., background or an isotype control). Markers not detected, or not detectable, using antibodies are determined to be positive or negative in a similar manner, using an appropriate control. For example, a cell or population of cells can be determined to be OCT-4⁺ if the amount of OCT-4 RNA detected in RNA from the cell or population of cells is detectably greater than background as determined, e.g., by a method of detecting RNA such as RT-PCR, slot blots, etc. Unless otherwise noted herein, cluster of differentiation ("CD") markers are detected using antibodies. OCT-4 can be determined to be present, and a cell is "OCT-4+", if OCT-4 RNA is detectable using RT-PCR.

5.2 Improved Compositions Comprising Cells and Methods of Making the Compositions Provided herein are improved methods of making compositions comprising cells, e.g., stem cells, e.g., placental stem cells, and improved compositions, e.g., pharmaceutical compositions, produced thereby. Compositions, e.g., compositions administrable in liquid form, comprising cells are generally better tolerated by a recipient when, e.g., cell clumps, particularly cell clumps visible to the naked eye (i.e., macro clumps), are removed prior to administration of the pharmaceutical composition to an individual. The methods of making compositions comprising cells, e.g., stem cells, such as stem cells from a human postpartum placenta that has been drained of blood, placental cells, as described herein result in compositions that are substantially better tolerated when administered to an individual.

In one embodiment, provided herein is a method of making a composition, comprising filtering a solution comprising cells to produce a filtered cell-containing solution; diluting the filtered cell-containing solution with a first dilution solution to no more than about $10\pm3\times10^6$ cells per milliliter, e.g., prior to cryopreservation; and optionally diluting the resulting filtered cell-containing solution with a second dilution solution comprising dextran to produce said composition. In another embodiment, provided herein is a method of making a composition, comprising filtering a solution comprising cells to produce a filtered cell-containing solution; diluting the filtered cell-containing solution with a first dilution solution to no more than about 1 to $50\times10^6$, 1 to $40\times10^6$, 1 to $30\times10^6$, 1 to $20\times10^6$, 1 to $15\times10^6$, or 1 to $10\times10^6$ cells per milliliter, e.g., prior to cryopreservation; and optionally diluting the resulting filtered cell-containing solution with a second dilution solution comprising dextran to produce said composition. In certain embodiments, if the number of cells is less than about $10\pm3\times10^6$ cells per milliliter, filtration is optional.

In a specific embodiment, the cells are stem cells. In a more specific embodiment, the stem cells are bone marrow-derived mesenchymal stem cells, or adult stem cells. In a specific embodiment, the cells are isolated placental cells. In a more specific embodiment, the isolated placental cells are placental stem cells or placental multipotent cells. In another specific embodiment, the cells are cells from placental perfusate, e.g., nucleated cells from placental perfusate. Methods of obtaining placental perfusate cells are described in Section 5.3.4, below.

In a specific embodiment, the cells are cryopreserved between said diluting with a first dilution solution and said diluting with said second dilution solution. In another specific embodiment, the first dilution solution comprises dextran and HSA. In another specific embodiment, said dextran in said first dilution solution is about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran. In another specific embodiment, said dextran in said first dilution solution or said second dilution solution is dextran 1. In another specific embodiment, said dextran in said first dilution solution and said second dilution solution is dextran 1. In another specific embodiment, said dextran in said first dilution solution or said second dilution solution is dextran 70. In another specific embodiment, said dextran in said first dilution solution and said second dilution solution is dextran 70. In another specific embodiment, the dextran in said first dilution solution or said second dilution solution is dextran 40. In another specific embodiment, the dextran in said first dilution solution and said second dilution solution is dextran 40. In another specific embodiment, said dextran 40 in said first dilution solution is about 2.5% dextran 40 to about 10% dextran 40. In another specific embodiment, said dextran 40 in said first dilution solution is about 2.5%, 3.0%, 3.5%, 4.0%, 4.5%, 5.0%, 5.5%, 5.75%, 6.0%, 6.5%, 7.0%, 7.5% 8.0%, 8.5%, 9.0%, 9.5% or 10% dextran 40. In another specific embodiment, said dextran 40 in said first dilution solution is about 5.5% dextran 40.

In other embodiments, said first and/or second dilution solutions may comprise a polysaccharide in addition to or other than, i.e., in place of, dextran. In certain embodiments, the polysaccharide is a polymer (2 or more subunits) of glucose, and does not comprise saccharide subunits that are not glucose. In other embodiments, said first and/or second dilution solutions comprise one or more of maltodextrin (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% maltodextrin), trehalose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% trehalose), or hetastarch (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% hetastarch). In other embodiments, the first and/or second dilution solutions comprise one or more of sucrose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% sucrose), heparin (e.g., about 55 USP units/ml heparin), or glycogen (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% glycogen). In a particular embodiment, said first and/or second dilution solutions comprises maltodextran in addition to or other than, i.e., in place of, dextran. In another particular embodiment, said first and/or second dilution solutions comprises trehalose in addition to or other than, i.e., in place of, dextran. In another particular embodiment, said first and/or second dilution solutions comprises hetastarch in addition to or other than, i.e., in place of, dextran.

In another specific embodiment, said HSA in said solution comprising HSA is about 1 to 17% HSA. In another specific embodiment, said HSA in said solution comprising HSA is about 1%, 2%, 3%, 4%, 5%, 6%, 7%, 8%, 9%, 10%, 11%, 12%, 13%, 14%, 15%, 16% or about 17% HSA. In another specific embodiment, said HSA in said solution comprising HSA is about 4 to 10% HSA. In another specific embodiment, said HSA in said solution comprising HSA is about 3.125% HSA. In another specific embodiment, said HSA in said solution comprising HSA is 5% HSA. In another specific embodiment, said HSA in said solution comprising HSA is 10% HSA. In another specific embodiment, said HSA in said solution comprising HSA is about 16.875%% HSA. In another specific embodiment, said first dilution solution comprises HSA. In another specific embodiment, said HSA in said first dilution solution is about 1 to 17% HSA. In another specific embodiment, said HSA in said first dilution solution is about 1%, 2%, 3%, 4%, 5%, 6%, 7%, 8%, 9%, 10%, 11%, 12%, 13%, 14%, 15%, 16% or 17% HSA. In another specific embodiment, said HSA in said first dilution solution is about 4 to 10% HSA. In another specific embodiment, said HSA in said first dilution solution is about 3.125% HSA. In another specific embodiment, said HSA in said first dilution solution is about 5% HSA. In another specific embodiment, said HSA in said first dilution solution is about 10% HSA. In another specific embodiment, said HSA in said first dilution is about 16.875% HSA.

In other embodiments, bovine serum albumin (BSA)(e.g., about 1%, 2%, 3%, 4%, 5%, 6%, 7%, 8%, 9%, 10%, 11%, 12%, 13%, 14% or 15% BSA) or fetal bovine serum (FBS) (e.g., about 1%, 2%, 3%, 4%, 5%, 6%, 7%, 8%, 9%, 10%, 11%, 12%, 13%, 14% or 15% FBS) may be used in addition to or in place of, i.e., instead of HSA in said solution.

In some embodiments, the ratio of HSA to dextran, e.g., dextran 1, dextran 40 or dextran 70, in the first solution is between about 6:1 HSA:dextran to about 1:2.6 HSA:dextran. In some embodiments, the ratio of HSA to dextran is about 6:1, 5.5:1, 5:1, 4.5:1, 4:1, 3.5:1, 3:1, 2.5:1, 2.0:1, 1.5:1, 1:1, 1:1.5, 1:2 or 1:2.6 HSA:dextran. In some embodiments, the ratio of HSA to dextran, e.g., dextran 1, dextran 40 or dextran 70, in the first solution is about 3.13% HAS/8.25% dextran. In some embodiments, the ratio of HSA to dextran, e.g., dextran 1, dextran 40 or dextran 70, in the first solution is about 16.88% HSA/2.75% dextran. In particular embodiments, the ratio of HSA to dextran, e.g., dextran 1, dextran 40 or dextran 70, in the first solution is about 10% HSA/ 5.5% dextran, e.g., dextran 1, dextran 40 or dextran 70.

In another specific embodiment, said first dilution solution further comprises a cryoprotectant. In a more specific embodiment, said cryoprotectant is dimethylsulfoxide (DMSO). In a particular embodiment, said first dilution solution further comprises about 1% to about 15%, about 2.5% to about 15%, about 2.5% to about 10%, about 5% to about 15%, about 5% to about 10% or about 10% to about 15% DMSO. In a particular embodiment, said first dilution solution further comprises about 1%, 2%, 3%, 4%, 5%, 6%, 7%, 8%, 9%, 10%, 11%, 12%, 13%, 14% or 15% DMSO. In a particular embodiment, said first dilution solution further comprises about 5% DMSO.

In a specific embodiment, said first dilution solution comprises about 5.5% dextran 40, about 10% HSA, and about 5% DMSO.

In another specific embodiment, said dextran 40 in said second dilution solution is about 10% dextran 40. In another specific embodiment, said composition comprising cells comprises about 2.5%, 3.0%, 3.5%, 4.0%, 4.5%, 5.0%, 5.5%, 5.75%, 6.0%, 6.5%, 7.0%, 7.5% 8.0%, 8.5%, 9.0%, 9.5% or 10% dextran. In another specific embodiment, said composition comprising cells comprises about 7.5% to about 9% dextran. In another specific embodiment, said composition comprises about $1.5 \times 10^6$ cells per milliliter to about $5.0 \times 10^6$ cells per milliliter. In another specific embodiment, said composition comprises about $1.0 \pm 0.3 \times 10^6$ cells per milliliter to about $5.0 \pm 1.5 \times 10^6$ cells per milliliter. In a specific embodiment, said second dilution solution does not comprise HSA.

The dextran usable in the methods provided herein can be dextran of molecular weight between about 1 kDa and about 150 kDa, e.g., 1 kDa (dextran 1), about 40 kDa (dextran 40) or about 70 kDa (dextran 70).

In another specific embodiment, the solution comprising cells comprises a cryoprotectant. If the solution comprising cells comprises fewer than about $10 \pm 3 \times 10^6$ cells per milliliter, the first dilution step can be omitted, and, in certain embodiments, the solution into which the cells are suspended can comprise a cryopreservative, e.g., DMSO, e.g., about 2% to about 15% DMSO, e.g., about 5% DMSO.

In another embodiment, provided herein is a method of making a composition, comprising: (a) filtering a solution comprising cells, e.g., isolated placental cells, e.g., placental stem cells or placental multipotent cells, or cells isolated from placental perfusate, e.g., total nucleated cells isolated from placental perfusate, dextran and human serum albumin (HSA) to produce a filtered cell-containing solution; (b) optionally diluting said filtered cell-containing solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter with a first dilution solution comprising dextran; and (c) optionally diluting the filtered cell-containing solution with a second dilution solution comprising dextran but not comprising HSA, thereby making a composition. In some embodiments, step (b) is performed where the filtered cell-containing solution in (a) comprises greater than about $15 \times 10^6$ cells per milliliter, wherein said diluting in step (b) is to about $15 \times 10^6$ cells per milliliter. In some embodiments, step (b) is performed where the filtered cell-containing solution in (a) comprises greater than about $10 \pm 3 \times 10^6$ cells per milliliter, wherein said diluting in step (b) is to about $10 \pm 3 \times 10^6$ cells per milliliter. In some embodiments in which said filtered cell-containing solution comprises less than about $10 \pm 3 \times 10^6$ cells per milliliter, diluting in step (b) is omitted and the solution in step (a) comprises a cryoprotectant, e.g., DMSO, e.g., about 2% to about 15% DMSO. In some embodiments, step (b) is performed where the filtered cell-containing solution in (a) comprises greater than about $7.5 \times 10^6$ cells per milliliter, wherein said diluting in step (b) is to about $7.5 \times 10^6$ cells per milliliter. In a specific embodiment of the method, said cells are cryopreserved prior to step (c). In certain embodiments, if the number of cells is less than about $10 \pm 3 \times 10^6$ cells per milliliter, filtration is optional. In a specific embodiment of the method, said cells are cryopreserved prior to step (c). In another specific embodiment, said dextran in said first dilution solution or said second dilution solution is dextran 40. In another specific embodiment, said dextran in said first dilution solution and said second dilution solution is dextran 40. In another specific embodiment, said dextran 40 in said first dilution solution is 5.0% dextran 40. In another specific embodiment, said dextran 40 in said first dilution solution is 5.5% dextran 40. In another specific embodiment, said HSA in said solution comprising cells is about 1% HSA to about 15% HSA. In another specific embodiment, said first dilution solution comprises HSA. In a more specific embodiment, said HSA in said first dilution solution is 5% HSA. In a more specific embodiment, said HSA in said first dilution solution is 10% HSA. In another specific embodiment, said first dilution solution further comprises a cryoprotectant. In a more specific embodiment, said cryoprotectant is DMSO, e.g., about 2% to about 15% DMSO. In another specific embodiment, said dextran 40 in said second dilution solution is 10% dextran 40. In another specific embodiment, said solution in step (a) comprises a cryoprotectant.

In one aspect of the method, the number of cell clumps in the final composition comprising cells is reduced or eliminated using filtration, preferably before cryopreservation. In certain embodiments in which the cells in the cell-containing solution are cryopreserved, the cell-containing solution is filtered prior to cryopreservation. For example, cells, e.g., placental stem cells, in solution can be passed through a filter prior to cryopreservation to remove visible cell clumps (aggregations of cells, i.e., macro cell clumps). In one embodiment, filtration comprises filtering the cell-containing solution through a filter prior to cryopreserving said cells, wherein said filter comprises pores between about 50 μM and about 150 μM in diameter (that is, the filter is about a 50 μM filter to about a 150 μM filter), wherein the filter is suitable for filtering solutions comprising cells. For example, the filter can be a filter comprising pores between about 50 and about 80 μM, between about 60 μM and about 90 μM, between about 70 μM and about 100 μM, between about 80 μM and about 110 μM, between about 90 μM and about 120 μM, between about 100 μM and about 130 μM, between about 110 μM and about 140 μM, or between about 120 μM and about 150 μM, or can be a 50, 55, 60, 65, 70, 75, 80, 85, 90, 95, 100, 105, 110, 115, 120, 125, 130, 135, 140, 145 or 150 μM filter. In a specific embodiment, said filter is a 70 μM filter. In another specific embodiment, said filter is a 100 μM filter. In another specific embodiment, said filter is about a 70 μM filter to a 100 μM filter. In another specific embodiment, said cell-containing solution is filtered after thawing in addition to being filtered prior to freezing.

In other certain embodiments, if the number of cells is less than about $10\pm3\times10^6$ cells per milliliter, filtration is optional.

In various embodiments, the method of making a composition comprising cells, e.g., isolated placental cells, comprises cryopreserving the cells at no more than about $50\times10^6$, $40\times10^6$, $30\times10^6$, $20\times10^6$, $15\times10^6$, $10\times10^6$, $9.5\times10^6$, $9\times10^6$, $8.5\times10^6$, $8\times10^6$, $7.5\times10^6$, $7\times10^6$, $6.5\times10^6$, $6\times10^6$, $5.5\times10^6$, $5\times10^6$, $4.5\times10^6$, $4\times10^6$, $3.5\times10^6$, $3\times10^6$, or $2.5\times10^6$ cells per milliliter. In a specific embodiment, the cells are cryopreserved at no more than about $10\pm3\times10^6$ cells per milliliter. In another specific embodiment, the cells are cryopreserved at no more than about $15\times10^6$ cells per milliliter. In another specific embodiment, the cells are cryopreserved at no more than about $5\times10^6$ cells per milliliter. In another specific embodiment, the cells are cryopreserved at about $5.0\times10^6$ to about $7.5\times10^6$ cells per milliliter. In another specific embodiment, the cells are cryopreserved at about $5\times10^6$ cells per milliliter. In another specific embodiment, the cells are cryopreserved at about $7.5\times10^6$ cells per milliliter. In a specific embodiment, the cells are cryopreserved at about $10\pm3\times10^6$ cells per milliliter. In another specific embodiment, said cells are cryopreserved at a number that, when said cells are thawed and diluted 1:1 to 1:11 (v/v), e.g., 1:1 to 1:5 (v/v), with dextran 40, e.g., 10% dextran 40, results in the formation of 2 or fewer visible cell clumps (i.e., macro cell clumps) per $10^6$ cells. In another specific embodiment, said isolated placental cells are cryopreserved at a number that, when said cells are thawed and diluted 1:1 to 1:11 (v/v), e.g., 1:1 to 1:5 (v/v), with dextran 40, e.g., 10% dextran 40, results in the formation of no visible cell clumps. In another specific embodiment, said cells are cryopreserved at a number that, when said cells are thawed and diluted 1:1 to 1:11 (v/v), e.g., 1:1 to 1:5 (v/v), with 10% dextran 40, results in the formation of fewer than about 150, 140, 130, 120, 110 or 100 micro cell clumps per $10^6$ cells.

In another embodiment, provided herein is a method of making a composition, e.g., comprising contacting cells, e.g., isolated placental cells, after cryopreservation with a solution comprising dextran 40, e.g., resuspending the cells or diluting the cells in a solution comprising dextran 40. In a specific embodiment, the solution comprises between about 2.5% dextran 40 to about 10% dextran 40 (w/v). In specific embodiments, the solution comprises about 5% dextran 40 to about 10% dextran 40 (w/v). In another specific embodiment, the solution is a 5.0% dextran solution or a 10% dextran solution. In another specific embodiment, the solution is a 5.5% dextran solution or a 10% dextran solution. In other embodiments, the dextran has a molecular weight, e.g., an average molecular weight, between about 1 kilodaltons and about 150 kilodaltons. In other embodiments, the dextran has a molecular weight, e.g., an average molecular weight, between about 1 kDa to about 150 kDa, about 1 kDa to about 125 kDa, about 1 kDa to about 100 kDa, about 1 kDa to about 75 kDa, about 1 kDa to about 50 kDa, or about 1 kDa to about 25 kDa. In other embodiments, the dextran has a molecular weight, e.g., an average molecular weight, between about 1 kDA to about 10 kDa, about 30 kDa to about 50 kDa, or about 60 kDa to about 80 kDa. In other embodiments, the solution comprises between about 2% dextran and about 25% dextran. In a specific embodiment, said solution comprises no HSA. In another specific embodiment, said solution is density matched to said cells, e.g., said placental stem cells, e.g., the solution is within 5%, 2%, 1%, 0.5%, 0.2% or 0.1% of the density of the isolated placental cells. In another specific embodiment, the solution is not density-matched to said cells.

In another embodiment, the method of making a composition comprising cells, e.g., isolated placental cells, comprises (a) filtering a cell-containing solution comprising said cells prior to cryopreservation; (b) cryopreserving the cells at about 1 to $50\times10^6$, 1 to $40\times10^6$, 1 to $30\times10^6$, 1 to $20\times10^6$, 1 to $15\times10^6$, or 1 to $10\times10^6$ cells per milliliter; (c) thawing the cells; and (d) diluting the cell-containing solution about 1:1 (v/v) to about 1:11 with a dextran 40 solution. In certain embodiments, about $15\times10^6$ cells are cryopreserved in step (b). In certain embodiments, the cells are cryopreserved in step (b) at no more than $15\times10^6$ cells per milliliter. In certain embodiments, no more than about $10\pm3\times10^6$ cells per milliliter are cryopreserved in step (b). In other certain embodiments, if the number of cells is less than about $10\pm3\times10^6$ cells per milliliter, filtration is optional. In a more specific embodiment, the cells in step (b) are cryopreserved in a solution comprising about 5% to about 10% dextran 40 and HSA.

In another embodiment, the method of making a composition comprises the following steps:

(a) filtering a solution comprising cells, 5.5% dextran 40 solution, and 10% HSA through a 70 μM filter to produce a filtered cell-containing solution;

(b) diluting the filtered cell-containing solution with a solution comprising 5.5% dextran 40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter;

(d) cryopreserving the cells in said filtered cell-containing solution;

(e) thawing the cells; and (f) optionally diluting the filtered cell-containing solution with 10% dextran 40.

In certain embodiments, said diluting in step (b) is to no more than about $15 \times 10^6$ cells per milliliter. In certain embodiments, said diluting in step (b) is to no more than about $10 \pm 3 \times 10^6$ cells/mL. In embodiments in which the filtered cell-containing solution comprises fewer than about $10 \pm 3 \times 10^6$ cells/mL, the solution in step (a) comprises a cryoprotectant, e.g., DMSO, e.g., about 1% to about 5% DMSO, and step (b) is omitted. In other certain embodiments, if the number of cells is less than about $10 \pm 3 \times 10^6$ cells per milliliter, filtration is optional. In some embodiments, step (f) comprises diluting the filtered cell-containing solution 1:1 to 1:11 (v/v) with 10% dextran 40. In some embodiments, step (f) comprises diluting the filtered cell-containing solution 1:1 to 1:5 (v/v) with 10% dextran 40.

In another embodiment, the method of making a composition provided herein comprises the following steps:

(a) centrifuging a plurality of cells to collect the cells;
(b) resuspending the cells in 5.5% dextran 40;
(c) centrifuging the cells to collect the cells;
(d) resuspending the cells in a 5.5% dextran 40 solution that comprises 10% HSA to produce a cell-containing solution;
(e) filtering the cell-containing solution through a 70 μM filter to produce a filtered cell-containing solution;
(f) diluting the filtered cell-containing solution in 5.5% dextran 40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter;
(g) cryopreserving the cells in said filtered cell-containing solution;
(h) thawing the cells; and
(i) optionally diluting the filtered cell-containing solution with 10% dextran 40.

In certain embodiments, said diluting in step (f) is to no more than about $15 \times 10^6$ cells per milliliter. In certain embodiments, said diluting in step (f) is no more than about $10 \pm 3 \times 10^6$ cells/mL. In other certain embodiments, if the number of cells is less than about $10 \pm 3 \times 10^6$ cells per milliliter, filtration is optional. In embodiments in which said resuspending in step (d) produces a cell-containing solution comprising fewer than about $10 \pm 3 \times 10^6$ cells/mL, the solution in step (d) comprises a cryoprotectant, e.g., DMSO, e.g., about 1% to about 5% DMSO, and step (t) is omitted. In some embodiments, step (i) comprises diluting the filtered cell-containing solution 1:1 to 1:5 (v/v) with 10% dextran 40. In some embodiments, step (i) comprises diluting the filtered cell-containing solution 1:1 to 1:11 (v/v) with 10% dextran 40.

In a specific embodiment of any of the above methods, DMSO is substantially removed from the composition comprising cells, such that the final concentration of DMSO in the composition is less than about 2.5%, 2.0%, 1.5%, 1.0%, 0.9%, 0.8%, 0.7%, 0.6%, 0.5%, 0.4%, 0.3%, 0.2% or about 0.1%. Removal of DMSO can be accomplished, e.g., by centrifuging the cells and resuspending the cells in 10% dextran 40. Such a centrifuging and resuspending step can be repeated one or more times.

In another specific embodiment of any of the above methods, the method further comprises concentrating the resulting cell composition to about $5 \times 10^6$ cells per milliliter to $1 \times 10^8$ cells per milliliter. Such a composition is useful, for example, for subcutaneous administration of the composition to an individual in need thereof.

In another specific embodiment of any of the above methods, the cell is a cell other than a placental stem cell. In more specific embodiments, for example, the cells can be stem cells or non-stem cells. In specific embodiments in which the cells are stem cells, the stem cells may be, e.g., adult stem cells, somatic stem cells, embryonic stem cells, embryonic germ cells, umbilical cord stem cells, amniotic fluid stem cells, bone marrow-derived mesenchymal stem cells, cord blood-derived mesenchymal stem cells, peripheral blood-derived mesenchymal stem cells, adipose-derived mesenchymal stem cells or periosteum-derived stem cells. In another specific embodiment, the cells are natural killer cells, e.g., $CD3^-$, $CD56^+$ natural killer cells.

In another aspect, provided herein are compositions, e.g., pharmaceutical compositions. In certain embodiments, the compositions are made by the above methods. In certain embodiments, the compositions lack visible cell clumps, i.e., macro cell clumps. In certain other embodiments, the compositions comprise substantially reduced numbers of micro cell clumps (those visible only with a microscope, e.g., a light microscope) compared to compositions that have not been filtered, e.g., about 50%, 60%, 70%, 80%, 90%, 95%, 96%, 97%, 98%, 99% fewer micro cell clumps.

In one embodiment, provided herein is a composition, e.g., a pharmaceutical composition, comprising a plurality of cells, e.g., a plurality of isolated placental cells, or cells isolated from placental perfusate, e.g., total nucleated cells from placental perfusate, in a solution comprising 10% dextran 40, wherein said composition comprises between about $1.0 \pm 0.3 \times 10^6$ cells per milliliter to about $5.0 \pm 1.5 \times 10^6$ cells per milliliter, and wherein said composition comprises no visible cell clumps (i.e., comprises no macro cell clumps). In some embodiments, said composition comprises between about $1.5 \times 10^6$ cells per milliliter to about $3.75 \times 10^6$ cells per milliliter. In certain other embodiments, the composition comprises between about $1.0 \times 10^6$ cells per milliliter and $15 \times 10^6$ cells per milliliter, e.g., between about $7.5 \times 10^6$ cells per milliliter and about $15 \times 10^6$ cells per milliliter. In certain other embodiments, the composition comprises less than about $20 \times 10^6$ cells per milliliter. In a specific embodiment, said cells have been cryopreserved and thawed. In another specific embodiment, said cells have been filtered through a 70 μM to 100 μM filter. In another specific embodiment, said composition comprises no macro cell clumps. In another specific embodiment, said composition comprises fewer than about 200 micro cell clumps per $10^6$ cells. In another specific embodiment, said composition comprises fewer than about 150 micro cell clumps per $10^6$ cells. In another specific embodiment, said composition comprises fewer than about 100 micro cell clumps per $10^6$ cells. In another specific embodiment, said composition comprises less than 1%, 0.9%, 0.8%, 0.7%, 0.6%, 0.5%, 0.4%, 0.3%, 0.2%, or 0.1% DMSO.

In some embodiments, the composition comprises about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% dextran, e.g., dextran 1, dextran 40 or dextran 70. In a specific embodiment, said composition comprises about 7.5% to about 9% dextran 40. In a specific embodiment, said composition comprises about 5.5% dextran 40.

In other embodiments, said composition comprises a polysaccharide in addition to or other than, i.e., in place of, dextran. In certain embodiments, the polysaccharide is a polymer of glucose that does not comprise non-glucose saccharide subunits. In other embodiments, said composition comprises maltodextrin (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% maltodextrin), trehalose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% trehalose), or hetastarch (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% hetastarch). In other embodiments, said composition comprises sucrose (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% sucrose), heparin (e.g., 55 USP units/ml heparin), or glycogen (e.g., about 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10% glycogen). In a particular embodiment, said composition comprises maltodextran in addition to or other than, i.e., in place of, dextran. In another particular embodiment, said composition comprises trehalose in addition to or instead of dextran. In another particular embodiment, said composition comprises hetastarch in addition to or instead of dextran.

In another specific embodiment, said composition comprises about 1% to about 17% HSA. In some embodiments, said composition comprises about 1%, 2%, 3%, 4%, 5%, 6%, 7%, 8%, 9%, 10%, 11%, 12%, 13%, 14%, 15%, 16%, or about 17% HSA. In some embodiments, said composition comprises about 3.125% HSA. In some embodiments, said composition comprises about 5% HSA. In some embodiments, said composition comprises about 10% HSA. In some embodiments, said composition comprises about 16.875% HSA.

In other embodiments, said composition comprises bovine serum albumin (BSA)(e.g., about 1%, 2%, 3%, 4%, 5%, 6%, 7%, 8%, 9%, 10%, 11%, 12%, 13%, 14% or 15% BSA) or fetal bovine serum (FBS) (e.g., about 1%, 2%, 3%, 4%, 5%, 6%, 7%, 8%, 9%, 10%, 11%, 12%, 13%, 14% or 15% FBS) in addition to or instead of HSA.

In some embodiments, the composition comprises a cryoprotectant, e.g., DMSO, e.g., about 1% to about 15% DMSO. In some embodiments, said composition comprises about 1% to about 5% DMSO. In some embodiments, said composition comprises about 1% to about 15%, about 2.5% to about 15%, about 2.5% to about 10%, about 5% to about 15%, about 5% to about 10% or about 10% to about 15% DMSO. In some embodiments, said composition comprises about 1%, 2%, 3%, 4%, 5%, 6%, 7%, 8%, 9%, 10%, 11%, 12%, 13%, 14% or 15% DMSO. In a particular embodiment, the composition comprises about 5% DMSO.

Further provided herein are compositions comprising cells, wherein said compositions are produced by one of the methods disclosed herein. For example, in one embodiment, provided herein is a composition comprising cells, wherein said composition is produced by a method comprising filtering a solution comprising the cells to form a filtered cell-containing solution; diluting the filtered cell-containing solution with a first solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter, e.g., prior to cryopreservation; and diluting the resulting filtered cell-containing solution with a second solution comprising dextran but not comprising HSA to produce said composition. In certain embodiments, said diluting is to no more than about $15 \times 10^6$ cells per milliliter. In certain embodiments, said diluting is to no more than about $10 \pm 3 \times 10^6$ cells per milliliter. In certain embodiments, said diluting is to no more than about $7.5 \times 10^6$ cells per milliliter. In other certain embodiments, if the number of cells is less than about $10 \pm 3 \times 10^6$ cells per milliliter, filtration is optional. In a specific embodiment, the cells are cryopreserved between said diluting with a first dilution solution and said diluting with said second dilution solution. In another specific embodiment, the first dilution solution comprises dextran and HSA. In another specific embodiment, the dextran in said first dilution solution or said second dilution solution is dextran 40. In another specific embodiment, the dextran in said first dilution solution and said second dilution solution is dextran 40. In another specific embodiment, said dextran 40 in said first dilution solution is 5.0% dextran 40. In another specific embodiment, said dextran 40 in said first dilution solution is 5.5% dextran 40. In another specific embodiment, said HSA in said solution comprising HSA is 10% HSA. In another specific embodiment, said first dilution solution comprises HSA. In a more specific embodiment, said HSA in said first dilution solution is 10% HSA. In another specific embodiment, said first dilution solution comprises a cryoprotectant. In a more specific embodiment, said cryoprotectant is DMSO. In another specific embodiment, said dextran 40 in said second dilution solution is about 10% dextran 40. In another specific embodiment, said composition comprising cells comprises about 7.5% to about 9% dextran. In another specific embodiment, said composition comprising cells comprises about $1.0 \pm 0.3 \times 10^6$ cells per milliliter to about $5.0 \pm 1.5 \times 10^6$ cells per milliliter. In another specific embodiment, said composition comprising cells comprises about $1.5 \times 10^6$ cells per milliliter to about $3.75 \times 10^6$ cells per milliliter.

In another embodiment, the composition comprising cells is made by a method comprising (a) filtering a cell-containing solution comprising said cells prior to cryopreservation to produce a filtered cell-containing solution; (b) cryopreserving the cells in the filtered cell-containing solution at about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (c) thawing the cells; and (d) diluting the filtered cell-containing solution about 1:1 to about 1:11 (v/v) with a dextran 40 solution. In certain embodiments, if the number of cells is less than about $10 \pm 3 \times 10^6$ cells per milliliter, filtration is optional. In a more specific embodiment, the cells in step (b) are cryopreserved at about $10 \pm 3 \times 10^6$ cells per milliliter. In a more specific embodiment, the cells in step (b) are cryopreserved in a solution comprising about 5% to about 10% dextran 40 and HSA. In certain embodiments, said diluting in step (d) is to no more than about $15 \times 10^6$ cells per milliliter.

In another embodiment, the composition comprising cells is made by a method comprising: (a) suspending the cells in a 5.5% dextran 40 solution that comprises 10% HSA to form a cell-containing solution; (b) filtering the cell-containing solution through a 70 µM filter; (c) diluting the cell-containing solution with a solution comprising 5.5% dextran 40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (d) cryopreserving the cells; (e) thawing the cells; and (f) diluting the cell-containing solution 1:1 to 1:11 (v/v) with 10% dextran 40. In certain embodiments, said diluting in step (b) is to no more than about $15 \times 10^6$ cells per milliliter. In certain embodiments, said diluting in step (b) is to no more than about $10 \pm 3 \times 10^6$ cells/mL. In another embodiment, the composition comprising cells is made by a method comprising: (a) centrifuging a plurality of cells to collect the cells; (b) resuspending the cells in 5.5% dextran 40; (c) centrifuging the cells to collect the cells; (d) resuspending the cells in a 5.5% dextran 40 solution that comprises 10% HSA; (e) filtering the cells through a 70 μM filter; (f) diluting the cells in 5.5% dextran 40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (g) cryopreserving the cells; (h) thawing the cells; and (i) diluting the cells 1:1 to 1:11 (v/v) with 10% dextran 40. In certain embodiments, said diluting in step (f) is to no more than about $15 \times 10^6$ cells per milliliter. In certain embodiments, said diluting in step (f) is to no more than about $10 \pm 3 \times 10^6$ cells/mL. In other certain embodiments, if the number of cells is less than about $10 \pm 3 \times 10^6$ cells per milliliter, filtration is optional.

The compositions, e.g., pharmaceutical compositions, comprising cells described herein can comprise any mammalian cell, including mammalian stem cells and mammalian non-stem cells. In some embodiments, the compositions, e.g., pharmaceutical compositions, comprising cells described herein can comprise isolated placental cells, e.g., any of the isolated placental cells described herein (see, e.g., Section 5.3, below). In a specific embodiment, the isolated placental cells are $CD34^-$, $CD10^+$ and $CD105^+$ as detected by flow cytometry. In a more specific embodiment, the isolated $CD34^-$, $CD10^+$, $CD105^+$ placental cells are placental stem cells. In another more specific embodiment, the isolated $CD34^-$, $CD10^+$, $CD105^+$ placental cells are multipotent placental cells. In another specific embodiment, the isolated $CD34^-$, $CD10^+$, $CD105^+$ placental cells have the potential to differentiate into cells of a neural phenotype, cells of an osteogenic phenotype, or cells of a chondrogenic phenotype. In a more specific embodiment, the isolated $CD34^-$, $CD10^+$, $CD105^+$ placental cells are additionally $CD200^+$. In another more specific embodiment, the isolated $CD34^-$, $CD10^+$, $CD105^+$ placental cells are additionally $CD90^+$ or $CD45^-$, as detected by flow cytometry. In another more specific embodiment, the isolated $CD34^-$, $CD10^+$, $CD105^+$ placental cells are additionally $CD90^+$ or $CD45^-$, as detected by flow cytometry. In a more specific embodiment, the $CD34^-$, $CD10^+$, $CD105^+$, $CD200^+$ placental cells are additionally $CD90^+$ or $CD45^-$, as detected by flow cytometry. In another more specific embodiment, the $CD34^-$, $CD10^+$, $CD105^+$, $CD200^+$ cells are additionally $CD90^+$ and $CD45^-$, as detected by flow cytometry. In another more specific embodiment, the $CD34^-$, $CD10^+$, $CD105^+$, $CD200^+$, $CD90^+$, $CD45^-$ cells are additionally $CD80^-$ and $CD86^-$, as detected by flow cytometry.

In a more specific embodiment, the $CD34^-$, $CD10^+$, $CD105^+$ cells are additionally one or more of $CD29^+$, $CD38^-$, $CD44^+$, $CD54^+$, $CD80^-$, $CD86^-$, $SH3^+$ or $SH4^+$. In another more specific embodiment, the cells are additionally $CD44^+$. In a specific embodiment of any of the isolated $CD34^-$, $CD10^+$, $CD105^+$ placental cells above, the cells are additionally one or more of $CD117^-$, $CD133^-$, $KDR^-$ ($VEGFR2^-$), HLA-A,B,$C^+$, HLA-DP,DQ,$DR^-$, and/or Programmed Death—1 Ligand $(PDL1)^+$.

In certain other embodiments of the compositions, said isolated placental cells are $CD200^+$ and HLA-$G^+$; $CD73^+$, $CD105^+$, and $CD200^+$; $CD200^+$ and OCT-$4^+$; $CD73^+$, $CD105^+$ and HLA-$G^+$; $CD73^+$ and $CD105^+$ and facilitate the formation of one or more embryoid-like bodies in a population of placental cells comprising said isolated placental cells when said population is cultured under conditions that allow the formation of an embryoid-like body; or OCT-$4^+$ and facilitate the formation of one or more embryoid-like bodies in a population of placental cells comprising the isolated placental cells when said population is cultured under conditions that allow formation of embryoid-like bodies; or any combination thereof. In a specific embodiment, said $CD200^+$, HLA-$G^+$ cells are $CD34^-$, $CD38^-$, $CD45^-$, $CD73^+$ and $CD105^+$. In another specific embodiment, said $CD73^+$, $CD105^+$, and $CD200^+$ cells are $CD34^-$, $CD38^-$, $CD45^-$, and HLA-$G^+$. In another specific embodiment, said $CD200^+$, OCT-$4^+$ cells are $CD34^-$, $CD38^-$, $CD45^-$, $CD73^+$, $CD105^+$ and HLA-$G^+$. In another specific embodiment, said $CD73^+$, $CD105^+$ and HLA-$G^+$ cells are $CD34^-$, $CD45^-$, OCT-$4^+$ and $CD200^+$. In another specific embodiment, said $CD73^+$ and $CD105^+$ cells are OCT-$4^+$, $CD34^-$, $CD38^-$ and $CD45^-$.

In another specific embodiment, said OCT-$4^+$ cells are $CD73^+$, $CD105^+$, $CD200^+$, $CD34^-$, $CD38^-$, and $CD45^-$. Isolated placental cells that can be contained within the compositions comprising cells, described herein, are described in more detail in Section 5.3, below.

In other specific embodiments of the compositions provided herein, the cell is a cell other than a placental stem cell. In more specific embodiments, for example, the cells can be stem cells or non-stem cells. In specific embodiments in which the cells are stem cells, the stem cells may be, e.g., adult stem cells, somatic stem cells, embryonic stem cells, embryonic germ cells, umbilical cord stem cells, amniotic fluid stem cells, bone marrow-derived mesenchymal stem cells, cord blood-derived mesenchymal stem cells, peripheral blood-derived mesenchymal stem cells, adipose-derived mesenchymal stem cells or periosteum-derived stem cells. In another specific embodiment, the cells are natural killer cells, e.g., $CD3^-$, $CD56^+$ natural killer cells.

5.3 Isolated Placental Cells and Isolated Placental Cell Populations

The isolated placental multipotent cells useful in the compositions, e.g., pharmaceutical compositions, provided herein are obtainable from a placenta or part thereof, that adhere to a tissue culture substrate and have characteristics of multipotent cells or stem cells. In certain embodiments, the isolated placental cells useful in the methods disclosed herein have the capacity to differentiate into non-placental cell types. The isolated placental cells useful in the methods disclosed herein can be either fetal or maternal in origin (that is, can have the genotype of either the fetus or mother, respectively). Preferably, the isolated placental cells and populations of isolated placental cells are fetal in origin. As used herein, the phrase "fetal in origin" or "non-maternal in origin" indicates that the isolated placental cells or populations of isolated placental cells are obtained from the umbilical cord or placental structures associated with the fetus, i.e., that have the fetal genotype. As used herein, the phrase "maternal in origin" indicates that the cells or populations of cells are obtained from a placental structures associated with the mother, e.g., which have the maternal genotype. Isolated placental cells, or populations of cells comprising the isolated placental cells, can comprise isolated placental cells that are solely fetal or maternal in origin, or can comprise a mixed population of isolated placental cells of both fetal and maternal origin. The isolated placental cells, and populations of cells comprising the isolated placental cells, can be identified and selected by the morphological, marker, and culture characteristics discussed below. Isolated placental cells suitable for use in the methods and compositions described herein can include, for example, those described in U.S. Patent Application Publication No. 2007/0275362 and U.S. Pat. No. 7,468,276, the disclosures of which are hereby incorporated by reference in their entireties.

5.3.1 Physical and Morphological Characteristics

The isolated placental cells described herein, when cultured in primary cultures or in cell culture, adhere to the tissue culture substrate, e.g., tissue culture container surface (e.g., tissue culture plastic), or to a tissue culture surface coated with extracellular matrix or ligands such as laminin, collagen (e.g., native or denatured), gelatin, fibronectin, ornithine, vitronectin, and extracellular membrane protein (e.g., MATRIGEL®). (BD Discovery Labware, Bedford, Mass.). The isolated placental cells in culture assume a generally fibroblastoid, stellate appearance, with a number of cytoplasmic processes extending from the central cell body. The cells are, however, morphologically distinguishable from fibroblasts cultured under the same conditions, as the isolated placental cells exhibit a greater number of such processes than do fibroblasts. Morphologically, isolated placental cells are also distinguishable from hematopoietic stem cells, which generally assume a more rounded, or cobblestone, morphology in culture.

5.3.2 Cell Surface, Molecular and Genetic Markers

Isolated placental cells, e.g., multipotent cells or stem cells, and populations of isolated placental cells, express a plurality of markers that can be used to identify and/or isolate the stem cells, or populations of cells that comprise the stem cells. The isolated placental cells, and placental cell populations described herein (that is, two or more isolated placental cells) include placental cells and placental cell-containing cell populations obtained directly from the placenta, or any part thereof (e.g., amnion, chorion, placental cotyledons, and the like). Isolated placental cell populations also include populations of (that is, two or more) isolated placental cells in culture, and a population in a container, e.g., a bag. The isolated placental cells described herein are not trophoblasts, cytotrophoblasts, hemangioblasts, embryonic germ cells or embryonic stem cells. Placental multipotent cells usable in the methods and compositions described herein are described in U.S. Patent Application Publication No. 2007/0275362, and U.S. Pat. Nos. 7,045,148 and 7,468,276, the disclosures of which are hereby incorporated by reference in their entireties, and as described below.

The isolated placental cells, usable in the compositions and methods provided herein, generally express the markers CD73, CD105, CD200, HLA-G, and/or OCT-4, and do not express CD34, CD38, or CD45, and are HLA-DP, DQ, and DR$^-$. The isolated multipotent cells are also generally CD10$^+$, CD29$^+$, CD54$^+$, CD90$^+$, CD44$^+$ and CD38$^+$. In certain embodiments, the cells are one or more of SSEA3-, SSEA4- or ABC-p$^+$. The isolated placental cells can also express HLA-ABC (MHC-1). These markers can be used, in any combination, to identify the isolated placental cells, e.g., isolated placental stem cells or isolated multipotent cells and to distinguish the isolated placental cells from other cell types. Because the isolated placental cells can express CD73 and CD105, they can have mesenchymal stem cell-like characteristics. Lack of expression of CD34, CD38 and/or CD45, for example, identifies the isolated placental cells as non-hematopoietic stem cells.

In certain embodiments, the isolated placental cells are isolated placental stem cells. In certain other embodiments, the isolated placental cells are isolated placental multipotent cells. In one embodiment, the isolated placental cells are CD34$^-$, CD10$^+$ and CD105$^+$ as detected by flow cytometry. In a specific embodiment, the isolated CD34$^-$, CD10$^+$, CD105$^+$ placental cells are placental stem cells. In another specific embodiment, the isolated CD34$^-$, CD10$^+$, CD105$^+$ placental cells are multipotent placental cells. In another specific embodiment, the isolated CD34$^-$, CD10$^+$, CD105$^+$ placental cells have the potential to differentiate into cells of a neural phenotype, cells of an osteogenic phenotype, or cells of a chondrogenic phenotype. In another specific embodiment, the isolated CD34$^-$, CD10$^+$, CD105$^+$ placental cells are additionally CD200$^+$. In another specific embodiment, the isolated CD34$^-$, CD10$^+$, CD105$^+$ placental cells are additionally CD45$^-$ or CD90$^+$. In another specific embodiment, the isolated CD34$^-$, CD10$^+$, CD105$^+$ placental cells are additionally CD45$^-$ and CD90$^+$, as detected by flow cytometry. In a more specific embodiment, the isolated CD34$^-$, CD10$^+$, CD105$^+$, CD200$^+$ placental cells are additionally CD90$^+$ or CD45$^-$, as detected by flow cytometry. In another more specific embodiment, the isolated CD34$^-$, CD10$^+$, CD105$^+$, CD200$^+$ placental cells are additionally CD90$^+$ and CD45$^-$, as detected by flow cytometry, i.e., the cells are CD34$^-$, CD10$^+$, CD45$^-$, CD90$^+$, CD105$^+$ and CD200$^+$. In a more specific embodiment, said CD34$^-$, CD10$^+$, CD45$^-$, CD90$^+$, CD105$^+$, CD200$^+$ cells are additionally CD80$^-$ and CD86$^-$.

In a specific embodiment, any of the CD34$^-$, CD10$^+$, CD105$^+$ cells described above are additionally one or more of CD29$^+$, CD38$^-$, CD44$^+$, CD54$^+$, SH3$^+$ or SH4$^+$. In another more specific embodiment, the cells are additionally CD44$^+$. In another specific embodiment of any of the isolated CD34$^-$, CD10$^+$, CD105$^+$ placental cells above, the cells are additionally one or more of CD117$^-$, CD133$^-$, KDR$^-$ (VEGFR2$^-$), HLA-A,B,C$^+$, HLA-DP,DQ,DR$^-$, and/or PDL1$^+$. In another specific embodiment, the CD34$^-$, CD10$^+$, CD105$^+$ placental cells are additionally one or more of CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD 106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^+$, or Programmed Death-1 Ligand (PDL1)$^+$, or any combination thereof. In a more specific embodiment, the CD34$^-$, CD10$^+$, CD105$^+$ placental cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^+$, and Programmed Death-1 Ligand (PDL1)$^+$.

In another embodiment, a cell population, usable in the compositions and methods provided herein, is a population of cells comprising, e.g., that is enriched for, CD34$^-$, CD10$^+$ and CD105$^+$ placental cells. In various embodiments, at least about 10%, at least about 20%, at least about 30%, at least about 40%, at least about 50%, or at least about 60% of cells in said cell population are CD34$^-$, CD10$^+$ and CD105$^+$ placental cells. Preferably, at least about 70% of cells in said cell population are CD34$^-$, CD10$^+$ and CD105$^+$ placental cells. More preferably, at least about 90%, 95%, or 99% of said cells are CD34$^-$, CD10$^+$ and CD105$^+$ placental cells. In a specific embodiment, the isolated CD34$^-$, CD10$^+$, CD105$^+$ placental cells are additionally CD200$^+$. In a more specific embodiment, the isolated CD34$^-$, CD10$^+$, CD105$^+$, CD200$^+$ placental cells are additionally CD90$^+$ or CD45$^-$, as detected by flow cytometry. In another more specific embodiment, the isolated CD34$^-$, CD10$^+$, CD105$^+$, CD200$^+$ placental cells are additionally CD90$^+$ and CD45$^-$, as detected by flow cytometry. In a more specific embodiment, any of the isolated CD34$^-$, CD10$^+$, CD105$^+$ placental cells described above are additionally one or more of CD29$^+$, CD38$^-$, CD44$^+$, CD54$^+$, SH3$^+$ or SH4$^+$. In another more specific embodiment, the isolated CD34⁻, CD10⁺, CD105⁺ placental cells, or isolated CD34⁻, CD10⁺, CD105⁺, CD200⁺ placental cells, are additionally CD44⁺. In a specific embodiment of any of the populations of cells comprising isolated CD34⁻, CD10⁺, CD105⁺ placental cells above, the isolated placental cells are additionally one or more of CD13⁺, CD29⁺, CD33⁺, CD38⁻, CD44⁺, CD45⁻, CD54⁺, CD62E⁻, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁺, or Programmed Death-1 Ligand (PDL1)⁺, or any combination thereof. In a more specific embodiment, the CD34⁻, CD10⁺, CD105⁺ cells are additionally CD13⁺, CD29⁺, CD33⁺, CD38⁻, CD44⁺, CD45⁻, CD54/ICAM⁺, CD62E⁻, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ, DR⁻, HLA-G⁺, and Programmed Death-1 Ligand (PDL1)⁺.

In certain embodiments, the isolated placental cells are one or more, or all, of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁺, and ABC-p⁺, wherein said isolated placental cells are obtained by physical and/or enzymatic disruption of placental tissue. In a specific embodiment, the isolated placental cells are OCT-4⁺ and ABC-p⁺. In another specific embodiment, the isolated placental cells are OCT-4⁺ and CD34⁻, wherein said isolated placental cells have at least one of the following characteristics: CD10⁺, CD29⁺, CD44⁺, CD45⁻, CD54⁺, CD90⁺, SH3⁺, SH4⁺, SSEA3⁻, and SSEA4⁻. In another specific embodiment, the isolated placental cells are OCT-4⁺, CD34⁻, CD10⁺, CD29⁺, CD44⁺, CD45⁻, CD54⁺, CD90⁺, SH3⁺, SH4⁺, SSEA3⁻, and SSEA4⁻. In another embodiment, the isolated placental cells are OCT-4⁺, CD34⁻, SSEA3⁻, and SSEA4⁻. In a more specific embodiment, the isolated placental cells are OCT-4⁺ and CD34⁻, and is either SH2⁺ or SH3⁺. In a more specific embodiment, the isolated placental cells are OCT-4⁺, CD34⁻, SH2⁺, and SH3⁺. In another more specific embodiment, the isolated placental cells are OCT-4⁺, CD34⁻, SSEA3⁻, and SSEA4⁻, and are either SH2⁺ or SH3⁺. In another more specific embodiment, the isolated placental cells are OCT-4⁺ and CD34⁻, and either SH2⁺ or SH3⁺, and is at least one of CD10⁺, CD29⁺, CD44⁺, CD45⁻, CD54⁺, CD90⁺, SSEA3⁻, or SSEA4⁻. In another more specific embodiment, the isolated placental cells are OCT-4⁺, CD34⁻, CD10⁺, CD29⁺, CD44⁺, CD45⁻, CD54⁺, CD90⁺, SSEA3⁻, and SSEA4⁻, and either SH2⁺ or SH3⁺.

In one embodiment, the isolated placental cells, usable in the compositions and methods provided herein, are CD200⁺ or HLA-G⁺. In a specific embodiment, the isolated placental cells are CD200⁺ and HLA-G⁺. In another specific embodiment, the isolated placental cells are CD73⁺ and CD105⁺. In another specific embodiment, said the isolated placental cells are CD34⁻, CD38⁻ or CD45⁻. In another specific embodiment, the isolated placental cells are CD34⁻, CD38⁻ and CD45⁻. In another specific embodiment, the isolated placental cells are CD34⁻, CD38⁻, CD45⁻, CD73⁺ and CD105⁺. In another specific embodiment, said CD200⁺ or HLA-G⁺ isolated placental cells facilitate the formation of embryoid-like bodies in a population of placental cells comprising the isolated placental cells, under conditions that allow the formation of embryoid-like bodies. In another specific embodiment, the isolated placental cells are isolated away from placental cells that are not stem or multipotent cells. In another specific embodiment, said isolated placental cells are isolated away from placental stem cells that do not display these markers.

In another embodiment, a cell population, usable in the compositions and methods provided herein, is a population of cells comprising, e.g., that is enriched for, CD200⁺, HLA-G⁺ placental cells. In various embodiments, at least about 10%, at least about 20%, at least about 30%, at least about 40%, at least about 50%, or at least about 60% of cells in said cell population are CD200⁺, HLA-G+placental cells. Preferably, at least about 70% of cells in said cell population are CD200⁺, HLA-G⁺ placental cells. More preferably, at least about 90%, 95%, or 99% of said cells are CD200⁺, HLA-G⁺ placental cells. In a specific embodiment of the isolated populations, said placental cells are also CD73⁺ and CD105⁺. In another specific embodiment, said placental cells are also CD34⁻, CD38⁻ or CD45⁻. In a more specific embodiment, said placental cells are also CD34⁻, CD38⁻, CD45⁻, CD73⁺ and CD105⁺. In another embodiment, said isolated population of cells produces one or more embryoid-like bodies when cultured under conditions that allow the formation of embryoid-like bodies. In another specific embodiment, said population of placental cells is isolated away from placental cells that are not stem cells. In another specific embodiment, said population of placental cells is isolated away from placental cells that do not display these markers.

In another embodiment, placental cells, usable in the compositions and methods provided herein, are CD73⁺, CD105⁺, and CD200⁺. In another specific embodiment, said placental cell is HLA-G⁺. In another specific embodiment, said placental cells are CD34⁻, CD38⁻ or CD45⁻. In another specific embodiment, said placental cells are CD34⁻, CD38⁻ and CD45⁻. In a more specific embodiment, said placental cells are CD34⁻, CD38⁻, CD45⁻, and HLA-G⁺. In another specific embodiment, the isolated CD73⁺, CD105⁺, and CD200⁺ placental cells facilitate the formation of one or more embryoid-like bodies in a population of said placental cells, when the population is cultured under conditions that allow the formation of embryoid-like bodies. In another specific embodiment, said placental cells are isolated away from placental cells that are not stem cells. In another specific embodiment, said placental cells are isolated away from placental cells that do not display these markers.

In another embodiment, a cell population usable in the compositions and methods provided herein, is a population of cells comprising, e.g., that is enriched for, isolated CD73⁺, CD105⁺, CD200⁺ placental cells. In various embodiments, at least about 10%, at least about 20%, at least about 30%, at least about 40%, at least about 50%, or at least about 60% of cells in said cell population are isolated CD73⁺, CD105⁺, CD200⁺ placental cells. In another embodiment, at least about 70% of said cells in said population of cells are isolated CD73⁺, CD105⁺,CD200⁺ placental cells. In another embodiment, at least about 90%, 95% or 99% of cells in said population of cells are isolated CD73⁺, CD105⁺, CD200⁺ placental cells. In a specific embodiment of said populations, the isolated placental cells are HLA-G⁺. In another specific embodiment, the isolated placental cells are additionally CD34⁻, CD38⁻ or CD45⁻.

In another specific embodiment, the isolated placental cells are additionally CD34⁻, CD38⁻ and CD45⁻. In a more specific embodiment, the isolated placental cells are additionally CD34⁻, CD38⁻, CD45⁻, and HLA-G⁺. In another specific embodiment, said population of cells produces one or more embryoid-like bodies when cultured under conditions that allow the formation of embryoid-like bodies. In another specific embodiment, said population of placental cells is isolated away from placental cells that are not stem cells. In another specific embodiment, said population of placental stem cells is isolated away from placental cells that do not display these characteristics.

In another embodiment, the isolated placental cells, usable in the compositions and methods provided herein, are $CD200^+$ and $OCT-4^+$. In a specific embodiment, the isolated placental cells are $CD73^+$ and $CD105^+$. In another specific embodiment, said isolated placental cells are $HLA-G^+$. In another specific embodiment, said isolated $CD200^+$, $OCT-4^+$ placental cells are $CD34^-$, $CD38^-$ or $CD45^-$. In another specific embodiment, said isolated $CD200^+$, $OCT-4^+$ placental cells are $CD34^-$, $CD38^-$ and $CD45^-$. In a more specific embodiment, said isolated $CD200^+$, $OCT-4^+$ placental cells are $CD34^-$, $CD38^-$, $CD45^-$, $CD73^+$, $CD105^+$ and $HLA-G^+$. In another specific embodiment, the isolated $CD200^+$, $OCT-4^+$ placental cells facilitate the production of one or more embryoid-like bodies by a population of placental cells that comprises the isolated cells, when the population is cultured under conditions that allow the formation of embryoid-like bodies. In another specific embodiment, said isolated $CD200^+$, $OCT-4^+$ placental cells are isolated away from placental cells that are not stem cells. In another specific embodiment, said isolated $CD200^+$, $OCT-4^+$ placental cells are isolated away from placental cells that do not display these characteristics.

In another embodiment, a cell population, usable in the compositions and methods provided herein, is a population of cells comprising, e.g., that is enriched for, $CD200^+$, $OCT-4^+$ placental cells. In various embodiments, at least about 10%, at least about 20%, at least about 30%, at least about 40%, at least about 50%, or at least about 60% of cells in said cell population are isolated $CD200^+$, $OCT-4^+$ placental cells. In another embodiment, at least about 70% of said cells are said isolated $CD200^+$, $OCT-4^+$ placental cells. In another embodiment, at least about 80%, 90%, 95%, or 99% of cells in said cell population are said isolated $CD200^+$, $OCT-4^+$ placental cells. In a specific embodiment of the isolated populations, said isolated $CD200^+$, $OCT-4^+$ placental cells are additionally $CD73^+$ and $CD105^+$. In another specific embodiment, said isolated $CD200^+$, $OCT-4^+$ placental cells are additionally $HLA-G^+$. In another specific embodiment, said isolated $CD200^+$, $OCT-4^+$ placental cells are additionally $CD34^-$, $CD38^-$ and $CD45^-$. In a more specific embodiment, said isolated $CD200^+$, $OCT-4^+$ placental cells are additionally $CD34^-$, $CD38^-$, $CD45^-$, $CD73^+$, $CD105^+$ and $HLA-G^+$. In another specific embodiment, the cell population produces one or more embryoid-like bodies when cultured under conditions that allow the formation of embryoid-like bodies. In another specific embodiment, said cell population is isolated away from placental cells that are not isolated $CD200^+$, $OCT-4^+$ placental cells. In another specific embodiment, said cell population is isolated away from placental cells that do not display these markers.

In another embodiment, the isolated placental cells, usable in the compositions and methods provided herein, are $CD73^+$, $CD105^+$ and $HLA-G^+$. In another specific embodiment, the isolated $CD73^+$, $CD105^+$ and $HLA-G^+$ placental cells are additionally $CD34^-$, $CD38^-$ or $CD45^-$. In another specific embodiment, the isolated $CD73^+$, $CD105^+$, $HLA-G^+$ placental cells are additionally $CD34^-$, $CD38^-$ and $CD45^-$. In another specific embodiment, the isolated $CD73^+$, $CD105^+$, $HLA-G^+$ placental cells are additionally $OCT-4^+$. In another specific embodiment, the isolated $CD73^+$, $CD105^+$, $HLA-G^+$ placental cells are additionally $CD200^+$. In a more specific embodiment, the isolated $CD73^+$, $CD105^+$, $HLA-G^+$ placental cells are additionally $CD34^-$, $CD38^-$, $CD45^-$, $OCT-4^+$ and $CD200^+$. In another specific embodiment, the isolated $CD73^+$, $CD105^+$, $HLA-G^+$ placental cells facilitate the formation of embryoid-like bodies in a population of placental cells comprising said cells, when the population is cultured under conditions that allow the formation of embryoid-like bodies. In another specific embodiment, said the isolated $CD73^+$, $CD105^+$, $HLA-G^+$ placental cells are isolated away from placental cells that are not the isolated $CD73^+$, $CD105^+$, $HLA-G^+$ placental cells. In another specific embodiment, said the isolated $CD73^+$, $CD105^+$, $HLA-G^+$ placental cells are isolated away from placental cells that do not display these markers.

In another embodiment, a cell population, usable in the compositions and methods provided herein, is a population of cells comprising, e.g., that is enriched for, isolated $CD73^+$, $CD105^+$ and HLA-G+placental cells. In various embodiments, at least about 10%, at least about 20%, at least about 30%, at least about 40%, at least about 50%, or at least about 60% of cells in said population of cells are isolated $CD73^+$, $CD105^+$, $HLA-G^+$ placental cells. In another embodiment, at least about 70% of cells in said population of cells are isolated $CD73^+$, $CD105^+$, $HLA-G^+$ placental cells. In another embodiment, at least about 90%, 95% or 99% of cells in said population of cells are isolated $CD73^+$, $CD105^+$, $HLA-G^+$ placental cells. In a specific embodiment of the above populations, said isolated $CD73^+$, $CD105^+$, HLA-G+placental cells are additionally $CD34^-$, $CD38^-$ or $CD45^-$. In another specific embodiment, said isolated $CD73^+$, $CD105^+$, $HLA-G^+$ placental cells are additionally $CD34^-$, $CD38^-$ and $CD45^-$. In another specific embodiment, said isolated $CD73^+$, $CD105^+$, $HLA-G^+$ placental cells are additionally $OCT-4^+$. In another specific embodiment, said isolated $CD73^+$, $CD105^+$, $HLA-G^+$ placental cells are additionally $CD200^+$. In a more specific embodiment, said isolated $CD73^+$, $CD105^+$, HLA-G+placental cells are additionally $CD34^-$, $CD38^-$, $CD45^-$, $OCT-4^+$ and $CD200^+$. In another specific embodiment, said cell population is isolated away from placental cells that are not $CD73^+$, $CD105^+$, $HLA-G^+$ placental cells. In another specific embodiment, said cell population is isolated away from placental cells that do not display these markers.

In another embodiment, the isolated placental cells, usable in the compositions and methods provided herein, are $CD73^+$ and $CD105^+$ and facilitate the formation of one or more embryoid-like bodies in a population of isolated placental cells comprising said $CD73^+$, $CD105^+$ cells when said population is cultured under conditions that allow formation of embryoid-like bodies. In another specific embodiment, said isolated $CD73^+$, $CD105^+$ placental cells are additionally $CD34^-$, $CD38^-$ or $CD45^-$. In another specific embodiment, said isolated $CD73^+$, $CD105^+$ placental cells are additionally $CD34^-$, $CD38^-$ and $CD45^-$. In another specific embodiment, said isolated $CD73^+$, $CD105^+$ placental cells are additionally $OCT-4^+$. In a more specific embodiment, said isolated $CD73^+$, $CD105^+$ placental cells are additionally $OCT-4^+$, $CD34^-$, $CD38^-$ and $CD45^-$. In another specific embodiment, said isolated $CD73^+$, $CD105^+$ placental cells are isolated away from placental cells that are not said cells. In another specific embodiment, said isolated $CD73^+$, $CD105^+$ placental cells are isolated away from placental cells that do not display these characteristics.

In another embodiment, a cell population, usable in the compositions and methods provided herein, is a population of cells comprising, e.g., that is enriched for, isolated placental cells that are CD73$^+$, CD105$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73$^+$, CD105$^+$ placental cells. In another embodiment, at least about 70% of cells in said population of cells are said isolated CD73$^+$, CD105$^+$ placental cells. In another embodiment, at least about 90%, 95% or 99% of cells in said population of cells are said isolated CD73$^+$, CD105$^+$ placental cells. In a specific embodiment of the above populations, said isolated CD73$^+$, CD105$^+$ placental cells are additionally CD34$^-$, CD38$^-$ or CD45$^-$. In another specific embodiment, said isolated CD73$^+$, CD105$^+$ placental cells are additionally CD34$^-$, CD38$^-$ and CD45$^-$. In another specific embodiment, said isolated CD73$^+$, CD105$^+$ placental cells are additionally OCT-4$^+$. In another specific embodiment, said isolated CD73$^+$, CD105$^+$ placental cells are additionally CD200$^+$. In a more specific embodiment, said isolated CD73$^+$, CD105$^+$ placental cells are additionally CD34$^-$, CD38$^-$, CD45$^-$, OCT-4$^+$ and CD200$^+$. In another specific embodiment, said cell population is isolated away from placental cells that are not said isolated CD73$^+$, CD105$^+$ placental cells. In another specific embodiment, said cell population is isolated away from placental cells that do not display these markers.

In another embodiment, the isolated placental cells, usable in the compositions and methods provided herein, are OCT-4$^+$ and facilitate formation of one or more embryoid-like bodies in a population of isolated placental cells comprising said cells when cultured under conditions that allow formation of embryoid-like bodies. In a specific embodiment, said isolated OCT-4$^+$ placental cells are additionally CD73$^+$ and CD105$^+$. In another specific embodiment, said isolated OCT-4$^+$ placental cells are additionally CD34$^-$, CD38$^-$, or CD45$^-$.

In another specific embodiment, said isolated OCT-4$^+$ placental cells are additionally CD200$^+$. In a more specific embodiment, said isolated OCT-4$^+$ placental cells are additionally CD73$^+$, CD105$^+$, CD200$^+$, CD34$^-$, CD38$^-$, and CD45$^-$. In another specific embodiment, said isolated OCT-4$^+$ placental cells are isolated away from placental cells that are not OCT-4$^+$ placental cells. In another specific embodiment, said isolated OCT-4$^+$ placental cells are isolated away from placental cells that do not display these characteristics.

In another embodiment, a cell population, usable in the compositions and methods provided herein, is a population of cells comprising, e.g., that is enriched for, isolated placental cells that are OCT-4$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4$^+$ placental cells. In another embodiment, at least about 70% of cells in said population of cells are said isolated OCT-4$^+$ placental cells. In another embodiment, at least about 80%, 90%, 95% or 99% of cells in said population of cells are said isolated OCT-4$^+$ placental cells. In a specific embodiment of the above populations, said isolated OCT-4$^+$ placental cells are additionally CD34$^-$, CD38$^-$ or CD45$^-$. In another specific embodiment, said isolated OCT-4$^+$ placental cells are additionally CD34$^-$, CD38$^-$ and CD45$^-$. In another specific embodiment, said isolated OCT-4$^+$ placental cells are additionally CD73$^+$ and CD105$^+$. In another specific embodiment, said isolated OCT-4$^+$ placental cells are additionally CD200$^+$. In a more specific embodiment, said isolated OCT-4$^+$ placental cells are additionally CD73$^+$,CD105$^+$, CD200$^+$,CD34$^-$,CD38$^-$, and CD45$^-$. In another specific embodiment, said cell population is isolated away from placental cells that are not said cells. In another specific embodiment, said cell population is isolated away from placental cells that do not display these markers.

In certain other embodiments, the isolated placental cells are one or more of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$-$, SSEA4$-$, OCT-4$^+$, MHC-I$^+$ or ABC-p$^+$. In a specific embodiment, the isolated placental cells are CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$-$, SSEA4$-$, and OCT-4$^+$. In another specific embodiment, the isolated placental cells are CD10$^+$, CD29$^+$, CD34$^-$, CD38$^-$, CD45$^-$, CD54$^+$, SH2$^+$, SH3$^+$, and SH4$^+$. In another specific embodiment, the isolated placental cells are CD10$^+$, CD29$^+$, CD34$^-$, CD38$^-$, CD45$^-$, CD54$^+$, SH2$^+$, SH3$^+$, SH4$^+$ and OCT-4$^+$. In another specific embodiment, the isolated placental cells are CD10$^+$, CD29$^+$, CD34$^-$, CD38$^-$, CD44$^+$, CD45$^-$, CD54$^+$, CD90$^+$, HLA-1$^+$, SH2$^+$, SH3$^+$, SH4$^+$. In another specific embodiment, the isolated placental cells are OCT-4$^+$ and ABC-p$^+$. In another specific embodiment, the isolated placental cells are SH2$^+$, SH3$^+$, SH4$^+$ and OCT-4$^+$. In another embodiment, the isolated placental cells are OCT-4$^+$, CD34$^-$, SSEA3$^-$, and SSEA4$^-$. In a specific embodiment, said isolated OCT-4$^+$, CD34$^-$, SSEA3$^-$, and SSEA4$^-$ placental cells are additionally CD10$^+$, CD29$^+$, CD34$^-$, CD44$^+$, CD45$^-$, CD54$^+$, CD90$^+$, SH2$^+$, SH3$^+$, and SH4$^+$. In another embodiment, the isolated placental cells are OCT-4$^+$ and CD34$^-$, and either SH3$^+$ or SH4$^+$. In another embodiment, the isolated placental cells are CD34$^-$ and either CD10$^+$, CD29$^+$, CD44$^+$, CD54$^+$, CD90$^+$, or OCT-4$^+$.

In another embodiment, isolated placental cells, usable in the compositions and methods provided herein, are isolated CD10$^+$, CD34$^-$, CD105$^+$, and CD200$^+$ placental cells.

In another embodiment, a cell population, usable in the compositions and methods provided herein, is a population of cells comprising placental cells, wherein at least about 70%, at least about 80%, at least about 90%, at least about 95% or at least about 99% of said population of cells are CD10$^+$, CD34$^-$, CD105$^+$, CD200$^+$ placental cells. In a specific embodiment of the above embodiments, said placental cells are additionally CD90$^+$ and CD45$^-$. In a specific embodiment, said placental cell or population of placental cells is isolated away from placental cells that are not stem cells. In another specific embodiment, said placental cell or population of placental cells is isolated away from placental cells that do not display these characteristics. In another specific embodiment, said isolated placental cell is non-maternal in origin. In another specific embodiment, at least about 90%, at least about 95%, or at least about 99% of said cells in said isolated population of placental cells, are non-maternal in origin.

In another specific embodiment of said isolated placental cells or populations of cells comprising the isolated placental cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of the isolated placental cells, or populations of cells comprising isolated placental cells, that are disclosed herein, said isolated placental cells are fetal in origin (that is, have the fetal genotype).

In another embodiment, placental cells, usable in the compositions and methods provided herein, are OCT-4$^+$ and facilitate formation of one or more embryoid-like bodies in a population of said isolated placental cells when cultured under conditions that allow formation of embryoid-like bodies. In a specific embodiment, said placental cells are CD73$^+$ and CD105$^+$. In another specific embodiment, said placental cells are CD34$^-$, CD38$^-$, or CD45$^-$. In another specific embodiment, said placental cells are CD200$^+$. In a more specific embodiment, said placental cells are CD73$^+$, CD105$^+$, CD200$^+$, CD34$^-$, CD38$^-$, and CD45$^-$. In another specific embodiment, said placental cells are isolated away from placental cells that are not stem cells. In another specific embodiment, said placental cells are isolated away from placental cells that do not display these characteristics.

In another embodiment, the isolated placental cells, usable in the compositions and methods provided herein, are isolated HLA-A,B,C$^-$, CD45$^-$, CD133$^-$ and CD34$^-$ placental cells. In another embodiment, a cell population, usable in the compositions and methods provided herein, is a population of cells comprising isolated placental cells, wherein at least about 70%, at least about 80%, at least about 90%, at least about 95% or at least about 99% of cells in said isolated population of cells are isolated HLA-A,B,C$^-$, CD45$^-$, CD133$^-$ and CD34$^-$ placental cells. In a specific embodiment, said isolated placental cell or population of isolated placental cells is isolated away from placental cells that are not HLA-A,B,C$^-$, CD45$^-$, CD133$^-$ and CD34$^-$ placental cells. In another specific embodiment, said isolated placental cells are non-maternal in origin. In another specific embodiment, said isolated population of placental cells are substantially free of maternal components; e.g., at least about 40%, 45%, 5-0%, 55%, 60%, 65%, 70%, 75%, 90%, 85%, 90%, 95%, 98% or 99% of said cells in said isolated population of placental cells are non-maternal in origin.

In another embodiment, the isolated placental cells, usable in the compositions and methods provided herein, are isolated CD10$^+$, CD13$^+$, CD33$^+$, CD45$^-$, CD117$^-$ and CD133$^-$ placental cells. In another embodiment, a cell population usable in the compositions and methods provided herein, is a population of cells comprising isolated placental cells, wherein at least about 70%, at least about 80%, at least about 90%, at least about 95% or at least about 99% of cells in said population of cells are isolated CD10$^+$, CD13$^+$, CD33$^+$, CD45$^-$, CD117$^-$ and CD133$^-$ placental cells. In a specific embodiment, said isolated placental cells or population of isolated placental cells is isolated away from placental cells that are not said isolated placental cells. In another specific embodiment, said isolated CD10$^+$,CD13$^+$, CD33$^+$, CD45$^-$, CD117$^-$ and CD133$^-$ placental cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said isolated population of placental cells, are non-maternal in origin. In another specific embodiment, said isolated placental cells or population of isolated placental cells are isolated away from placental cells that do not display these characteristics.

In another embodiment, the isolated placental cells, usable in the compositions and methods provided herein, are isolated CD10$^-$, CD33$^-$, CD44$^+$, CD45$^-$, and CD117$^-$ placental cells. In another embodiment, a cell population, usable in the compositions and methods provided herein, is a population of cells comprising, e.g., enriched for, isolated placental cells, wherein at least about 70%, at least about 80%, at least about 90%, at least about 95% or at least about 99% of cells in said population of cells are isolated CD10$^-$, CD33$^-$, CD44$^+$, CD45$^-$, and CD117$^-$ placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cell or population of isolated placental cells is isolated away from placental cells that do not display these markers.

In another embodiment, the isolated placental cells, usable in the compositions and methods provided herein, are isolated CD10$^-$, CD13$^-$, CD33$^-$, CD45$^-$, and CD117$^-$ placental cells. In another embodiment, a cell population useful, usable in the compositions and methods provided herein, is a population of cells comprising, e.g., enriched for, isolated CD10$^-$, CD13$^-$, CD33$^-$, CD45$^-$, and CD117$^-$ placental cells, wherein at least about 70%, at least about 80%, at least about 90%, at least about 95% or at least about 99% of cells in said population are CD10$^-$,CD13$^-$,CD33$^-$, CD45$^-$, and CD117$^-$ placental cells. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells is isolated away from placental cells that do not display these characteristics.

In another embodiment, the isolated placental cells, usable in the compositions and methods provided herein, are HLA A,B,C$^+$, CD45$^-$, CD34$^-$, and CD133$^-$, and are additionally CD10$^+$, CD13$^+$, CD38$^+$, CD44$^+$, CD90$^+$, CD105$^+$, CD200$^+$ and/or HLA-G$^+$, and/or negative for CD117. In another embodiment, a cell population, usable in the compositions and methods provided herein, is a population of cells comprising isolated placental cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental cells that are HLA A,B,C$^-$, CD45$^-$, CD34$^-$, CD133$^-$, and that are additionally positive for CD10, CD13, CD38, CD44, CD90, CD105, CD200 and/or HLA-G, and/or negative for CD117. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells are isolated away from placental cells that do not display these markers.

In another embodiment, the isolated placental cells, usable in the compositions and methods provided herein, are isolated placental cells that are CD200$^+$ and CD10$^+$, as determined by antibody binding, and CD117$^-$, as determined by both antibody binding and RT-PCR. In another embodiment, the isolated placental cells, usable in the compositions and methods provided herein, are isolated placental cells, e.g., placental stem cells or placental multipotent cells, that are CD10$^+$, CD29$^-$, CD54$^+$, CD200$^+$, HLA-G$^+$, HLA class I$^-$ and β-2-microglobulin$^-$. In another embodiment, isolated placental cells, usable in the compositions and methods provided herein, are placental cells wherein the expression of at least one cellular marker is at least two-fold higher than for a mesenchymal stem cell (e.g., a bone marrow-derived mesenchymal stem cell). In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental cells, usable in the compositions and methods provided herein, are isolated placental cells, e.g., placental stem cells or placental multipotent cells, that are one or more of CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105+, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a specific embodiment, the isolated placental cells are at least CD29$^+$ and CD54$^+$. In another specific embodiment, the isolated placental cells are at least CD44$^+$ and CD106$^+$. In another specific embodiment, the isolated placental cells are at least CD29$^+$.

In another embodiment, a cell population, usable in the compositions and methods provided herein, comprises isolated placental cells, and at least 50%, 60%, 70%, 80%, 90%, 95%, 98% or 99% of the cells in said cell population are isolated placental cells that are one or more of CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a more specific embodiment, at least 50%, 60%, 70%, 80%, 90%, 95%, 98% or 99% of cells in said cell population are CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and PDL1$^{low}$.

In certain embodiments of isolated placental cells, said isolated placental cells do not differentiate during culturing in growth medium, i.e., medium formulated to promote proliferation, e.g., during proliferation in growth medium. In another specific embodiment, said isolated placental cells do not require a feeder layer in order to proliferate. In another specific embodiment, said isolated placental cells do not differentiate in culture in the absence of a feeder layer, solely because of the lack of a feeder cell layer.

In another embodiment, cells, usable in the compositions and methods provided herein, are isolated placental cells, wherein a plurality of said isolated placental cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, provided herein is a population of isolated umbilical cord cells, e.g., multipotent isolated umbilical cord cells, wherein a plurality of said isolated umbilical cord cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of isolated placental cells or isolated umbilical cord cells shows at least three-fold, or at least five-fold, higher ALDH activity than a population of bone marrow-derived mesenchymal stem cells having about the same number of cells and cultured under the same conditions.

In another specific embodiment of said isolated placental cells or populations of cells comprising the isolated placental cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings.

In another specific embodiment of the isolated placental cells, or populations of cells comprising isolated placental cells, that are disclosed herein, said isolated placental cells are fetal in origin (that is, have the fetal genotype).

In a specific embodiment of any of the above isolated placental cells or cell populations of isolated placental cells, the karyotype of the cells, or at least about 95% or about 99% of the cells in said population, is normal. In another specific embodiment of any of the above placental cells or cell populations, the cells, or cells in the population of cells, are non-maternal in origin.

Isolated placental cells, or populations of isolated placental cells, bearing any of the above combinations of markers, can be combined in any ratio. Any two or more of the above isolated placental cell populations can be combined to form an isolated placental cell population. For example, an population of isolated placental cells can comprise a first population of isolated placental cells defined by one of the marker combinations described above, and a second population of isolated placental cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental cells or isolated placental cells populations can be combined.

Isolated placental cells, usable in the compositions and methods provided herein, can be obtained, e.g., by disruption of placental tissue, with or without enzymatic digestion (see Section 5.4.3) or perfusion (see Section 5.4.4). For example, populations of isolated placental cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental cells; and isolating a plurality of said isolated placental cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental cells, contained within a population of cells obtained from perfusion of a placenta, are at least 50%, 60%, 70%, 80%, 90%, 95%, 99% or at least 99.5% of said population of placental cells. In another specific embodiment, the isolated placental cells collected by perfusion comprise fetal and maternal cells. In another specific embodiment, the isolated placental cells collected by perfusion are at least 50%, 60%, 70%, 80%, 90%, 95%, 99% or at least 99.5% fetal cells.

In another specific embodiment, provided herein is a composition comprising a population of the isolated placental cells, as described herein, collected by perfusion, wherein said composition comprises at least a portion of the perfusion solution used to collect the isolated placental cells.

Isolated populations of the isolated placental cells described herein can be produced by digesting placental tissue with a tissue-disrupting enzyme to obtain a population of placental cells comprising the cells, and isolating, or substantially isolating, a plurality of the placental cells from the remainder of said placental cells. The whole, or any part of, the placenta can be digested to obtain the isolated placental cells described herein. In specific embodiments, for example, said placental tissue can be a whole placenta, an amniotic membrane, chorion, a combination of amnion and chorion, or a combination of any of the foregoing. In other specific embodiment, the tissue-disrupting enzyme is trypsin or collagenase. In various embodiments, the isolated placental cells, contained within a population of cells obtained from digesting a placenta, are at least 50%, 60%, 70%, 80%, 90%, 95%, 99% or at least 99.5% of said population of placental cells.

Gene profiling confirms that isolated placental cells, and populations of isolated placental cells, are distinguishable from other cells, e.g., mesenchymal stem cells, e.g., bone marrow-derived mesenchymal stem cells. The isolated placental cells described herein can be distinguished from, e.g., mesenchymal stem cells on the basis of the expression of one or more genes, the expression of which is significantly higher in the isolated placental cells, or in certain isolated umbilical cord stem cells, in comparison to bone marrow-derived mesenchymal stem cells. In particular, the isolated placental cells, usable in the compositions and methods provided herein, can be distinguished from mesenchymal stem cells on the basis of the expression of one or more genes, the expression of which is significantly higher (that is, at least twofold higher) in the isolated placental cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, 1L6, IL18, KRT18, KRT8, LIPG, LRAP, MATN$^2$, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In a more specific embodiment, said isolated placental cells express said one or more genes when cultured for from about 3 to about 35 population doublings in a medium comprising DMEM-LG (Gibco); 2% fetal calf serum (Hyclone Labs.); 1× insulin-transferrin-selenium (ITS); 1× linoleic acid-bovine serum albumin (LA-BSA); $10^{-9}$ M dexamethasone (Sigma); $10^{-4}$ M ascorbic acid 2-phosphate (Sigma); epidermal growth factor 10 ng/mL (R&D Systems); and platelet-derived growth factor (PDGF-BB) 10 ng/mL (R&D Systems). In a specific embodiment, the isolated placental cell-specific or isolated umbilical cord cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (FE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In a more specific embodiment, said isolated placental cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In more specific embodiments, placental cell populations can be selected by selecting placental cells that express one or more genes at a detectably higher level than a bone marrow-derived mesenchymal stem cell, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to the number of passages said placental cell has undergone. In a more specific embodiment, said selecting comprises selecting cells that express ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, 1L6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN and ZC3H12A at a detectably higher level than a bone marrow-derived mesenchymal stem cell.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental cells, to identify a population of cells as comprising at least a plurality of isolated placental cells, or the like. Populations of isolated placental cells, the identity of which is confirmed, can be clonal, e.g., populations of isolated placental cells expanded from a single isolated placental cell, or a mixed population of stem cells, e.g., a population of cells comprising solely isolated placental cells that are expanded from multiple isolated placental cells, or a population of cells comprising isolated placental cells, as described herein, and at least one other type of cell.

The level of expression of these genes can be used to select populations of isolated placental cells. For example, a population of cells, e.g., clonally-expanded cells, may be selected if the expression of one or more of the genes listed above is significantly higher in a sample from the population of cells than in an equivalent population of mesenchymal stem cells. Such selecting can be of a population from a plurality of isolated placental cell populations, from a plurality of cell populations, the identity of which is not known, etc.

Isolated placental cells can be selected on the basis of the level of expression of one or more such genes as compared to the level of expression in said one or more genes in, e.g., a mesenchymal stem cell control, for example, the level of expression in said one or more genes in an equivalent number of bone marrow-derived mesenchymal stem cells. In one embodiment, the level of expression of said one or more genes in a sample comprising an equivalent number of mesenchymal stem cells is used as a control. In another embodiment, the control, for isolated placental cells tested under certain conditions, is a numeric value representing the level of expression of said one or more genes in mesenchymal stem cells under said conditions.

The isolated placental cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^4$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The isolated populations of placental cells described above, and populations of isolated placental cells generally, can comprise about, at least, or no more than, $1\times10^5$, $5\times10^5$, $1\times10^6$, $5\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated placental cells. Populations of isolated placental cells usable in the compositions and methods provided herein comprise at least 50%, 55%, 60%, 65%, 70%, 75%, 80%, 85%, 90%, 95%, 98%, or 99% viable isolated placental cells, as determined by, e.g., trypan blue exclusion.

5.3.3 Growth in Culture

The growth of the isolated placental cells described herein, as for any mammalian cell, depends in part upon the particular medium selected for growth. Under optimum conditions, isolated placental cells typically double in number in 3-5 days. During culture, the isolated placental cells described herein adhere to a substrate in culture, e.g. the surface of a tissue culture container (e.g., tissue culture dish plastic, fibronectin-coated plastic, and the like) and form a monolayer.

Populations of isolated placental cells described herein, when cultured under appropriate conditions, form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the isolated placental cells described herein, but remain attached to the adherent cells during culture. Embryoid-like body cells are dependent upon the adherent isolated placental cells for viability, as embryoid-like bodies do not form in the absence of the adherent isolated placental cells. The adherent isolated placental cells thus facilitate the growth of one or more embryoid-like bodies in a population of placental cells that comprise the adherent isolated placental cells. Without wishing to be bound by theory, the cells of the embryoid-like bodies are thought to grow on the adherent isolated placental cells much as embryonic stem cells grow on a feeder layer of cells. Mesenchymal stem cells, e.g., bone marrow-derived mesenchymal stem cells, do not develop embryoid-like bodies in culture.

5.3.4 Hematopoietic Placental Stem Cells

In certain embodiments, the isolated placental cells are $CD34^+$ placental cells, e.g., hematopoietic placental cells. Such $CD34^+$ cells are not, however, encompassed by the term "multipotent" as used herein. Such cells are obtainable from placental tissue, e.g., from a placenta that has been drained of cord blood and perfused to remove residual blood. In certain embodiments, the $CD34^+$ isolated placental cells are $CD38^+$. In certain embodiments, the $CD34^+$ isolated placental cells are $CD38^-$. In certain other embodiments, the $CD34^+$ isolated placental cells are $CD45^+$. In a specific embodiment, the isolated placental cells are $CD34^+$, $CD38^-$ and $CD45^+$.

5.3.5 Placental Perfusate Cells

In certain embodiments, the cells of the compositions provided herein, formulated by the methods provided herein, are cells obtained from placental perfusate. As used herein, "cells obtained from placental perfusate" includes total nucleated cells obtained from, e.g., isolated from, placental perfusate, a subset of nucleated cells obtained from placental perfusate, or cells cultured or proliferated from cells obtained directly from placental perfusate. Placental perfusate may be obtained from a placenta that has been drained of cord blood and perfused to remove residual blood, prior to perfusion to obtain placental cells. Placental perfusate may be obtained from a placenta that has been drained of cord blood but not perfused to remove residual blood. Placental perfusate may be obtained from a placenta that has neither been drained of cord blood nor perfused to remove residual blood. In the latter two embodiments, the placental cells, e.g., nucleated cells from placental perfusate, for example, total nucleated cells from placental perfusate, comprise nucleated cells from placental blood and/or cord blood. Methods for obtaining placental perfusate, and cells from placental perfusate, are described in Section 5.4.4, below.

5.4 Methods of Obtaining Isolated Placental Cells

5.4.1 Stem Cell Collection Composition

Further provided herein are methods of collecting and isolating placental cells e.g., the isolated placental cells described in Section 5.2, above. Generally, such cells are obtained from a mammalian placenta using a physiologically-acceptable solution, e.g., a stem cell collection composition. A cell collection composition is described in detail in related U.S. Patent Application Publication No. 2007/0190042, entitled "Improved Medium for Collecting Placental Stem Cells and Preserving Organs."

The cell collection composition can comprise any physiologically-acceptable solution suitable for the collection and/or culture of cells, e.g., the isolated placental cells described herein, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve isolated placental cells, that is, prevent the isolated placental cells from dying, or delay the death of the isolated placental cells, reduce the number of isolated placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa*, *Staphylococcus aureus*, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.4.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of isolated placental cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to cell collection, can be stored under sterile conditions and at either room temperature or at a temperature of 5 to 25° C. (centigrade). The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain isolated placental cells.

5.4.3 Physical Disruption and Enzymatic Digestion of Placental Tissue

In one embodiment, stem cells are collected from a mammalian placenta by physical disruption of part of all of the organ. For example, the placenta, or a portion thereof, may be, e.g., crushed, sheared, minced, diced, chopped, macerated or the like. The tissue can then be cultured to obtain a population of isolated placental cells. Typically, the placental tissue is disrupted using, e.g., in, a placental cell collection composition (see Section 5.2 and below).

The placenta can be dissected into components prior to physical disruption and/or enzymatic digestion and stem cell recovery. Placental stem cells can be obtained from all or a portion of the amniotic membrane, chorion, umbilical cord, placental cotyledons, or any combination thereof, including from a whole placenta. Preferably, isolated placental cells are obtained from placental tissue comprising amnion and chorion. Typically, isolated placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Stem cells can generally be collected from a placenta, or portion thereof, at any time within about the first three days post-expulsion, but preferably between about 8 hours and about 18 hours post-expulsion.

In a specific embodiment, the disrupted tissue is cultured in tissue culture medium suitable for the proliferation of isolated placental cells (see, e.g., Section 5.5, below, describing the culture of isolated placental cells).

In another specific embodiment, isolated placental are collected by physical disruption of placental tissue, wherein the physical disruption includes enzymatic digestion, which can be accomplished by use of one or more tissue-digesting enzymes. The placenta, or a portion thereof, may also be physically disrupted and digested with one or more enzymes, and the resulting material then immersed in, or mixed into, a cell collection composition.

A preferred cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental cells, e.g., placental stem cells and placental multipotent cells. For example, in one embodiment, a placenta, or part thereof, is digested first with an appropriate amount of collagenase I at about 1 to about 2 mg/ml for, e.g., 30 minutes, followed by digestion with trypsin, at a concentration of about 0.25%, for, e.g., 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the placental cell collection composition, or to a solution in which the tissue is disrupted and/or digested prior to isolation of the placental cells with the placental cell collection composition.

Following digestion, the digestate is washed, for example three times, with culture medium, and the washed cells are seeded into culture flasks. The cells are then isolated by differential adherence, and characterized for, e.g., viability, cell surface markers, differentiation, and the like.

It will be appreciated that where an entire placenta, or portion of a placenta comprising both fetal and maternal cells (for example, where the portion of the placenta comprises the chorion or cotyledons), the placental cells collected will comprise a mix of placental cells, e.g., placental stem cells or placental multipotent cells, derived from both fetal and maternal sources. Where a portion of the placenta that comprises no, or a negligible number of, maternal cells (for example, amnion), the placental cells collected will comprise almost exclusively fetal placental cells, e.g., fetal placental stem cells or fetal placental multipotent cells.

Placental cells can be isolated from disrupted tissue by differential trypsinization (see Section 5.4.5, below) followed by culture in one or more new culture containers in fresh proliferation medium, optionally followed by a second differential trypsinization step.

5.4.4 Placental Perfusion

Placental cells, e.g., placental stem cells or placental multipotent cells, can also be obtained by perfusion of the mammalian placenta. Methods of perfusing mammalian placenta to obtain placental cells are disclosed, e.g., in Hariri, U.S. Pat. Nos. 7,045,148 and 7,255,729, and in related U.S. Patent Application Publication No. 2007/0190042, each of which is incorporated herein in its entirety.

Placental cells can be collected by perfusion, e.g., through the placental vasculature, using, e.g., a cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental cells e.g., placental stem cells or placental multipotent cells, of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain placental cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In another embodiment, perfusion, e.g., to collect placental perfusate cells, is performed as follows. Placenta(e) containing placental blood are perfused through only the placental vasculature by pumping sterile 0.9% NaCl (e.g., about 750 mL) using, e.g., a peristaltic pump, and the resulting perfusate is collected in a collection bag. Cells from the perfusate are collected by centrifugation, e.g., at about 420 g, followed by removal of excess supernatant (NaCl, plasma, anticoagulant). Hetastarch is then added to the perfusate cells to obtain a 30% dilution. The perfusate cells are then placed into a plasma extractor, e.g., for about an hour, to separate erythrocytes. Resulting plasma and nucleated cells are separated from the collection bag, and placed again in a plasma extractor. Remaining cells are resuspended in 5% human serum albumin in a final volume of about 20 mL. Premixed DMSO/PLASMALYTE A® (1:1 v/v) is added to obtain a volume of about 24 mL. The resulting cells are cryopreserved. In specific embodiments of this method, the placenta from which the perfusate is obtained is drained of cord blood, but not perfused, prior to perfusion to collect placental cells. In another specific embodiment, the placenta from which the perfusate is obtained is drained of cord blood, and is perfused to remove residual blood, prior to perfusion to collect placental cells.

In one embodiment, the proximal umbilical cord is clamped during perfusion, and more preferably, is clamped within 4-5 cm (centimeter) of the cord's insertion into the placental disc.

The volume of perfusion liquid used to collect placental cells may vary depending upon the number of cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled. In a preferred embodiment, stem cells are collected at a time or times between about 8 hours and about 18 hours post-expulsion.

Perfusion preferably results in the collection of significantly more placental cells than the number obtainable from a mammalian placenta not perfused with said solution, and not otherwise treated to obtain placental cells (e.g., by tissue disruption, e.g., enzymatic digestion). In this context, "significantly more" means at least 10% more. Perfusion yields significantly more placental stem cells than, e.g., the number of placental cells obtainable from culture medium in which a placenta, or portion thereof, has been cultured.

Placental cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental cells are washed after several minutes with a cold (e.g., 4° C.) stem cell collection composition.

5.4.5 Isolation, Sorting, and Characterization of Placental Stem Cells

The isolated placental cells, e.g., the cells described in Section 5.3, above, whether obtained by perfusion or by physical disruption, e.g., by enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because the isolated placental cells typically detach from plastic surfaces within about five minutes whereas other adherent populations typically require more than 20-30 minutes incubation. The detached placental cells can be harvested following trypsinization and trypsin neutralization, using, e.g., Trypsin Neutralizing Solution (TNS, Cambrex). In one embodiment of isolation of adherent cells, aliquots of, for example, about $5-10\times10^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34$^+$. Likewise, if a cell produces enough OCT-4 RNA to be detectable by RT-PCR, or significantly more OCT-4 RNA than an adult cell, the cell is OCT-4+Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, cells from placenta, e.g., placental stem cells and placental multipotent cells, are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34⁻ cells are retained, and cells that are CD200⁺HLA-G⁺, are separated from all other CD34 cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are CD200⁺, HLA-G⁺, CD73⁺, CD105⁺, CD34⁻, CD38⁻ and CD45⁻ are isolated from other placental cells for further use.

With respect to antibody-mediated detection and sorting of placental cells, e.g., placental stem cells or placental multipotent cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and biotinylated CD90 (BD Biosciences Pharmingen). Other antibodies that can be used include, but are not limited to, CD133-APC (Miltenyi), KDR-Biotin (CD309, Abcam), Cytokeratin K-FITC (Sigma or Dako), HLA ABC-FITC (BD), HLA DR,DQ,DP-PE (BD), β-2-microglobulin-PE (BD), CD80-PE (BD) and CD86-APC (BD).

Other antibody/label combinations that can be used include, but are not limited to, CD45-PerCP (peridin chlorophyll protein); CD44-PE; CD19-PE; CD10-F (fluorescein); HLA-G-F and 7-amino-actinomycin-D (7-AAD); HLA-ABC-F; and the like.

The isolated placental cells provided herein can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

The isolated placental cells described herein can be labeled with an antibody to a single marker and detected and/sorted. Placental cells can also be simultaneously labeled with multiple antibodies to different markers.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Isolated placental cells can also be characterized and/or sorted based on cell morphology and growth characteristics. For example, isolated placental cells can be characterized as having, and/or selected on the basis of, e.g., a fibroblastoid appearance in culture. Isolated placental cells can also be characterized as having, and/or be selected, on the basis of their ability to form embryoid-like bodies. In one embodiment, for example, isolated placental cells that are fibroblastoid in shape, express CD73 and CD105, and produce one or more embryoid-like bodies in culture are isolated from other placental cells. In another embodiment, OCT-4⁺ placental cells that produce one or more embryoid-like bodies in culture are isolated from other placental cells.

In another embodiment, isolated placental cells can be identified and characterized by a colony forming unit assay. Colony forming unit assays are commonly known in the art, such as MESENCULT™ medium (Stem Cell Technologies, Inc., Vancouver British Columbia).

Isolated placental cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Isolated placental cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.5 Culture Of Isolated Placental Cells 5.5.1 Culture Media

Isolated placental cells, or populations of isolated placental cells, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL™ (BD Discovery Labware, Bedford, Mass.)).

Isolated placental cells can be cultured in any medium, and under any conditions, recognized in the art as acceptable for the culture of cells, e.g., stem cells. Preferably, the culture medium comprises serum. The isolated placental cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 1% to 20% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX™ and gentamicin; DMEM comprising 10% FBS, GLUTAMAX™ and gentamicin, etc.

Other media in that can be used to culture placental cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The isolated placental cells can be cultured in standard tissue culture conditions, e.g., in tissue culture dishes or multiwell plates. The isolated placental cells can also be cultured using a hanging drop method. In this method, isolated placental cells are suspended at about $1 \times 10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

In one embodiment, the isolated placental cells are cultured in the presence of a compound that acts to maintain an undifferentiated phenotype in the isolated placental cell. In a specific embodiment, the compound is a substituted 3,4-dihydropyridimol[4,5-d]pyrimidine. In a more specific embodiment, the compound is a compound having the following chemical structure:

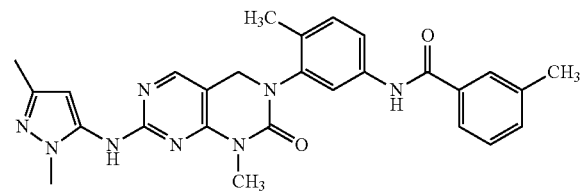

The compound can be contacted with isolated placental cells, or a population of isolated placental cells, at a concentration of, for example, between about 1 µM to about 10 µM.

5.5.2 Expansion and Proliferation of Placental Cells

Once an isolated placental cell, or population of isolated placental cell (e.g., a placental cell or population of placental cells separated from at least 50% of the placental cells with which the stem cell or population of stem cells is normally associated in vivo), the cell or population of cells can be proliferated and expanded in vitro. For example, a population of the isolated placental cells can be cultured in tissue culture containers, e.g., dishes, flasks, multiwell plates, or the like, for a sufficient time for the cells to proliferate to 70-90% confluence, that is, until the cells and their progeny occupy 70-90% of the culturing surface area of the tissue culture container.

The isolated placental cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured in the presence of about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental cells, e.g., placental stem cells or placental multipotent cells, preferably are grown under low oxidative stress (e.g., with addition of glutathione, ascorbic acid, catalase, tocopherol, N-acetylcysteine, or the like).

Once a confluence of less than about 100%, for example 70%-90%, is obtained, the cells may be passaged. For example, the cells can be enzymatically treated, e.g., trypsinized, using techniques well-known in the art, to separate them from the tissue culture surface. After removing the cells by pipetting and counting the cells, about 10,000-100,000 cells/cm$^2$, preferably about 50,000 cells/cm$^2$, are passaged to a new culture container containing fresh culture medium. Typically, the new medium is the same type of medium from which the isolated placental cells were removed. The isolated placental cells can be passaged at least 1, 2, 3, 4, 5, 6, 7, 8, 9, 10, 12, 14, 16, 18, or 20 times, or more.

Production of a Placental Cell Bank

Isolated cells from postpartum placentas, e.g., the isolated placental cells described in Section 5.3, above, can be cultured in a number of different ways to produce a set of lots, e.g., a set of individually-administrable doses, of isolated placental cells. Such lots can, for example, be obtained from cells from placental perfusate or from cells from enzyme-digested placental tissue. Sets of lots of placental cells, obtained from a plurality of placentas, can be arranged in a bank of isolated placental cells for, e.g., long-term storage. Generally, tissue culture plastic-adherent placental cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, placental cell lots are obtained as follows. Placental tissue is first disrupted, e.g., by mincing, digested with a suitable enzyme, e.g., collagenase (see Section 5.4.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and are then used to seed expansion cultures. Expansion cultures can be any arrangement of separate cell culture apparatuses, e.g., a Cell Factory by NUNC™. Cells can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ stem cells. Preferably, from about $1 \times 10^3$ to about $1 \times 10^4$ cells/cm$^2$ are used to seed each expansion culture. The number of expansion cultures may be greater or fewer in number depending upon the particular placenta(s) from which the cells are obtained.

Expansion cultures are grown until the density of cells in culture reaches a certain value, e.g., about $1 \times 10^5$ cells/cm$^2$. Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 50 million cells per ml, and can comprise between about $10^6$ and about $10^{10}$ cells in total.

In one embodiment, therefore, a placental cell bank can be made by a method comprising: expanding primary culture placental cells from a human postpartum placenta for a first plurality of population doublings; cryopreserving said placental cells to form a Master Cell Bank; expanding a plurality of placental cells from the Master Cell Bank for a second plurality of population doublings; cryopreserving said placental cells to form a Working Cell Bank; expanding a plurality of placental cells from the Working Cell Bank for a third plurality of population doublings; and cryopreserving said placental cells in individual doses, wherein said individual doses collectively compose a placental cell bank. In another specific embodiment, said primary culture placental cells comprise placental cells from placental perftisate. In another specific embodiment, said primary culture placental cells comprise placental cells from digested placental tissue. In another specific embodiment, said primary culture placental cells comprise placental cells from placental perfusate and from digested placental tissue. In another specific embodiment, all of said placental cells in said placental cell primary culture are from the same placenta. In another specific embodiment, the method further comprises the step of selecting CD200$^+$ or HLA-G+placental cells or CD10$^+$, CD34$^-$, CD105$^+$, CD200$^+$, placental cells from said plurality of said placental cells from said Working Cell Bank to form individual doses. In another specific embodiment, said individual doses comprise from about $10^4$ to about $10^5$ placental cells. In another specific embodiment, said individual doses comprise from about $10^5$ to about $10^6$ placental cells. In another specific embodiment, said individual doses comprise from about $10^6$ to about $10^7$ placental cells. In another specific embodiment, said individual doses comprise from about $10^7$ to about $10^8$ placental cells. In another specific embodiment, said individual doses comprise from about $10^8$ to about $10^9$ placental cells. In another specific embodiment, said individual doses comprise from about $10^9$ to about $10^{10}$ placental cells.

The methods of making compositions comprising placental cells, e.g., placental stem cells or placental multipotent cells, as provided herein, can be integrated into the construction of a placental cell bank at any step as described above. In one embodiment, the pharmaceutical composition is produced after the Master Cell Bank is produced, and during production of one or more Working Cell Banks from said Master Cell Bank, or during expansion of placental cells from said Working Cell Banks. For example, placental cells can be thawed from a Working Cell Bank and cultured for a plurality of population doublings. In one embodiment, when a desired number of cells is generated, or a desired number of population doublings has taken place, the placental cells can be collected, e.g., by centrifugation, and resuspended in a solution comprising, e.g., dextran 40, e.g., 5.5% dextran 40. In certain embodiments, the placental stem cells are collected a second time and resuspended in a solution comprising dextran and a cryopreservant, e.g., a 5.5% dextran 40 solution comprising 10% HSA and 5% DMSO, and cryopreserved. The cryopreserved placental cells are thawed, e.g., immediately before use, e.g., immediately before final production of the composition as described in Section 5.2, above.

The above methods of producing a composition comprising placental cells, e.g., placental stem cells or placental multipotent cells, can be used once in the production and/or use of a placental cell bank, e.g., at each point at which the placental cells would be cryopreserved, or, e.g., at the point at which placental cells are prepared for individual administration prior to final cryopreservation, and upon thawing prior to administration to an individual.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental cell lots, including before or after establishment of the initial cell culture, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.6 Preservation of Placental Cells

Isolated placental cells, e.g., the isolated placental multipotent cells described in Section 5.2, above, can be preserved, e.g., during collection, that is, placed under conditions that allow for long-term storage, or conditions that inhibit cell death by, e.g., apoptosis or necrosis, e.g., during collection or prior to production of the compositions described herein, e.g., using the methods described herein.

Placental cells can be preserved using, e.g., a composition comprising an apoptosis inhibitor, necrosis inhibitor and/or an oxygen-carrying perfluorocarbon, as described in related U.S. Application Publication No. 2007/0190042, the disclosure of which is incorporated herein by reference in its entirety. In one embodiment, a method of preserving a population of cells, to be used in the compositions comprising cells presented herein, comprises contacting said population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of cells, as compared to a population of cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said cells. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the cells. In another more specific embodiment, said apoptosis inhibitor and said perfluorocarbon are between about 2° C. and 10° C., or between about 2° C. and about 5° C., at the time of contacting the cells. In another more specific embodiment, said contacting is performed during transport of said population of cells. In another more specific embodiment, said contacting is performed during freezing and thawing of said population of cells.

Populations of placental cells can be preserved, e.g., by a method comprising contacting said population of cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, placental stem cells are contacted with a cell collection composition comprising an apoptosis inhibitor and oxygen-carrying perfluorocarbon, organ-preserving compound, or combination thereof, during perfusion. In another embodiment, said cells are contacted during a process of tissue disruption, e.g., enzymatic digestion. In another embodiment, placental cells are contacted with said cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a cell, or population of cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of cells is exposed to said hypoxic condition for less than two hours during said preservation. In another more specific embodiment, said population of cells is exposed to said hypoxic condition for less than one hour, or less than thirty minutes, or is not exposed to a hypoxic condition, during collection, enrichment or isolation. In another specific embodiment, said population of cells is not exposed to shear stress during collection, enrichment or isolation.

Placental cells can be cryopreserved, in general or in the specific methods disclosed herein. In one embodiment, the cryopreservative used to cryopreserve placental cells is DMSO. In another embodiment, the cryopreservative is propylene glycol, e.g., about 1.5M propylene glycol. The cryopreservative may also be, e.g., glycerol, ethylene glycol, polyphenol (e.g., at about 30 to about 120 ppm) or the like In other embodiments, the cryopreservative is fetal bovine serum, human serum, or human serum albumin in combination with one or more of DMSO, trehalose, and dextran. In a specific embodiment, the cryopreservative is human serum, DMSO, and trehalose, or is fetal bovine serum and DMSO. In certain embodiments, the placental cells are cryopreserved in cryopreservation medium in small containers, e.g., ampoules. Placental cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

5.7 Cell Containing Compositions 5.7.1 Compositions Comprising Placental Cells

The placental cells described herein, e.g., in Section 5.3, can comprise one or more of the placental cells, e.g., placental stem cells or placental multipotent cells, described herein, wherein the cells have been isolated from a placenta, e.g., a human placenta. In another specific embodiment, any of the foregoing compositions comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

In another embodiment, a composition useful in the compositions, e.g., pharmaceutical compositions, provided herein comprises medium conditioned by any of the foregoing placental cells, or any of the foregoing placental cell populations. In a specific embodiment, any such composition comprises a stem cell that is not derived from a placenta. In a more specific embodiment, said stem cell is an embryonic stem cell. In another more specific embodiment, said stem cell is a mesenchymal stem cell. In another more specific embodiment, said stem cell is a bone marrow-derived stem cell. In another more specific embodiment, said stem cell is a hematopoietic progenitor cell. In another more specific embodiment, said stem cell is a somatic stem cell. In an even more specific embodiment, said somatic stem cell is a neural stem cell, a hepatic stem cell, a pancreatic stem cell, an endothelial stem cell, a cardiac stem cell, or a muscle stem cell.

5.7.1.1 Pharmaceutical Compositions

Populations of isolated placental cells, or populations of cells comprising the isolated placental cells, are contained within, or are components of, a pharmaceutical composition.

Isolated placental cells can be prepared in a form that is easily administrable to an individual, e.g., placental perfusate cells or isolated placental cells that are contained within a container suitable for medical use. Such a container can be, for example, a syringe, sterile plastic bag, flask, jar, or other container from which the placental stem cell population can be easily dispensed. For example, the container can be a blood bag or other plastic, medically-acceptable bag suitable for the intravenous administration of a liquid to a recipient. The container in certain embodiments one that allows for cryopreservation of the isolated placental cell population.

In one embodiment, the container is a container that facilitates, or allows, performance of one or more of the method steps described herein. For example, where the method of producing a composition comprising cells comprises, e.g., the steps of (a) contacting said cells with a solution comprising dextran and human serum albumin (HSA) to produce a cell-containing solution; (b) filtering the solution; (c) diluting said cells to about 1 to $50\times10^6$, 1 to $40\times10^6$, 1 to $30\times10^6$, 1 to $20\times10^6$, 1 to $15\times10^6$, or 1 to $10\times10^6$ cells per milliliter with a first dilution solution comprising dextran; and (d) diluting said cells with a second dilution solution comprising dextran but not comprising HSA, the cells, e.g., isolated placental cells or placental perfusate cells, can be placed into a container, e.g., between steps (c) and (d), wherein the container is a container that, e.g., facilitates cryopreservation and/or facilitates delivery of the cells to an individual in need of the cells, or the like. In certain embodiments, said diluting is to no more than about $15\times10^6$ cells per milliliter. In certain embodiments, said diluting is to no more than about $10\pm3\times10^6$ cells per milliliter. In other certain embodiments, if the number of cells is less than about $10\pm3\times10^6$ cells per milliliter, filtration is optional.

For example, the isolated placental cells can be cryopreserved in, e.g., a bag, e.g., a blood bag or similar bag, and thawed and finally diluted in the same bag. In another embodiment, wherein the method of producing a composition comprising cells comprises, e.g., (a) centrifuging a plurality of cells, e.g., placental perfusate cells or isolated placental cells to collect the cells; (b) resuspending the cells in 5.5% dextran 40; (c) centrifuging the cells to collect the cells; (d) resuspending the cells in a 5.5% dextran 40 solution that comprises 10% HSA; (e) filtering the cells through a 70 μM to 100 μM filter; (f) diluting the cells in 5.5% dextran 40, 10% HSA, and 5% DMSO to no more than about $10\pm3\times10^6$ cells/mL; (g) cryopreserving the cells; (h) thawing the cells; and (i) diluting the cells 1:1 to 1:11 with 10% dextran 40 to produce said pharmaceutical composition, placement of the cells in a container that, e.g., facilitates cryopreservation and/or administration of the cells to an individual in need thereof can be performed, e.g., at any step after step (e). In certain embodiments, said diluting in step (f) is to about 1 to $50\times10^6$, 1 to $40\times10^6$, 1 to $30\times10^6$, 1 to $20\times10^6$, 1 to $15\times10^6$, or 1 to $10\times10^6$ cells per milliliter. In certain embodiments, said diluting in step (f) is to no more than about $15\times10^6$ cells per milliliter. In other certain embodiments, if the number of cells is less than about $10\pm3\times10^6$ cells per milliliter, filtration is optional. In a specific embodiment, for example, cells, e.g., isolated placental cells or placental perfusate cells, can be placed into the container after filtration, then, in the container, diluted, cryopreserved, thawed, and/or finally diluted prior to administration to the individual.

Isolated placental cells in the compositions, e.g., pharmaceutical compositions, provided herein, can comprise placental cells derived from a single donor, or from multiple donors. The isolated placental cells can be completely HLA-matched to an intended recipient, or partially or completely HLA-mismatched.

Thus, in one embodiment, isolated placental cells in the compositions provided herein are administered to an individual in need thereof. In a specific, said isolated placental cells are administered intramuscularly, intradermally, intraperitoneally, intra-arterially, subcutaneously, intravenously or intraocularly. In one embodiment, isolated placental cells in the compositions provided herein are administered to an individual in need thereof in the form of a composition comprising isolated placental cells in a container. In another specific embodiment, the container is a bag, flask, or jar. In more specific embodiment, said bag is a sterile plastic bag. In a more specific embodiment, said bag is suitable for, allows or facilitates intravenous administration of said isolated placental cells, e.g., by intravenous infusion, bolus injection, or the like. The bag can comprise multiple lumens or compartments that are interconnected to allow mixing of the isolated placental cells and one or more other solutions, e.g., a drug, prior to, or during, administration. In another specific embodiment, prior to cryopreservation, the solution comprising the isolated placental cells comprises one or more compounds that facilitate cryopreservation of the combined cells. In another specific embodiment, said isolated placental cells are contained within a physiologically-acceptable aqueous solution. In a more specific embodiment, said physiologically-acceptable aqueous solution is a 0.9% NaCl solution. In another specific embodiment, said isolated placental cells comprise placental cells that are HLA-matched to a recipient of said cell population. In another specific embodiment, said combined cells comprise placental cells that are at least partially HLA-mismatched to a recipient of said cell population. In another specific embodiment, said placental cells are derived from a plurality of donors.

The isolated placental cells in the pharmaceutical composition can be any of the isolated placental cells described herein. In a specific embodiment, the isolated placental cells described herein are $CD10^+$, $CD34^-$, $CD105^+$, $CD200^+$, cells that are contained within a container. In a specific embodiment, the isolated placental cells described herein are $CD200^+$, HLA-$G^+$ cells that are contained within a container. In another specific embodiment, the isolated placental cells are $CD73^+$, $CD105^+$, $CD200^+$ cells that are contained within a container. In another specific embodiment, the isolated placental cells are $CD200^+$, OCT-$4^+$ cells that are contained within a container. In another specific embodiment, the isolated placental cells are $CD73^+$, $CD105^+$ cells that are contained within a container, wherein said cells facilitate the formation of one or more embryoid-like bodies when cultured with a population of placental cells under conditions that allow for the formation of embryoid-like bodies. In another specific embodiment, the isolated placental cells are $CD73^+$, $CD105^+$, HLA-$G^+$ cells that have been cryopreserved, and are contained within a container. In another specific embodiment, the isolated placental cells are OCT-$4^+$ cells that are contained within a container, wherein said cells facilitate the formation of one or more embryoid-like bodies when cultured with a population of placental cells under conditions that allow for the formation of embryoid-like bodies. In a specific embodiment of any of the foregoing placental cells, said container is a bag.

In various specific embodiments, said container comprises about, at least, or at most $1\times10^6$ isolated placental cells or placental perfusate cells, $5\times10^6$ isolated placental cells or placental perfusate cells, $1×10^7$ isolated placental cells or placental perfusate cells, $5×10^7$ isolated placental cells or placental perfusate cells, $1×10^8$ isolated placental cells or placental perfusate cells, $5×10^8$ isolated placental cells or placental perfusate cells, $1×10^9$ isolated placental cells or placental perfusate cells, $5×10^9$ isolated placental cells or placental perfusate cells, or $1×10^{10}$ isolated placental cells or placental perfusate cells. In other embodiments, a single unit dose of isolated placental cells or placental perfusate cells can comprise, in various embodiments, about, at least, or no more than $1×10^5$, $5×10^5$, $1×10^6$, $5×10^6$, $1×10^7$, $5×10^7$, $1×10^8$, $5×10^8$, $1×10^9$, $5×10^9$, $1×10^{10}$, $5×10^{10}$, $1×10^{11}$ or more isolated placental cells or placental perfusate cells. In other embodiments, a container or dose of isolated placental cells or placental perfusate cells comprises $1×10^5$ to $5×10^5$ isolated placental cells or placental perfusate cells, $5×10^5$ to $1×10^6$ isolated placental cells or placental perfusate cells, $1×10^6$ to $5×10^6$ isolated placental cells or placental perfusate cells, $5×10^6$ to $1×10^7$ isolated placental cells or placental perfusate cells, $1×10^7$ to $5×10^7$ isolated placental cells or placental perfusate cells, $5×10^7$ to $1×10^8$ isolated placental cells or placental perfusate cells, $1×10^8$ to $5×10^8$ isolated placental or placental perfusate cells, $5×10^8$ to $1×10^9$ isolated placental or placental perfusate cells, $1×10^9$ to $5×$ isolated placental cells or placental perfusate cells, $5×10^9$ to $1×10^{10}$ isolated placental cells or placental perfusate cells, $1×10^{10}$ to $5×10^{10}$ isolated placental cells or placental perfusate cells, $5×10^{10}$ to $1×10^{11}$ isolated placental cells or placental perfusate cells, or more isolated placental or placental perfusate cells. In a preferred embodiment, the pharmaceutical composition comprises a sufficient number of isolated placental cells or placental perfusate cells to administer about $2×10^7$ to about $10×10^7$ cells per kilogram of a recipient.

In other specific embodiments of any of the foregoing cryopreserved populations, said cells have been passaged about, at least, or no more than 5 times, no more than 10 times, no more than 15 times, or no more than 20 times. In another specific embodiment of any of the foregoing cryopreserved cells, said cells have been expanded within said container.

Pharmaceutical compositions comprising the placental stem cells described herein can comprise any, or any combination, of the isolated placental cell types, described elsewhere herein. The pharmaceutical compositions can comprise fetal, maternal, or both fetal and maternal placental cells, e.g., placental stem cells or placental multipotent cells. The pharmaceutical compositions provided herein can further comprise isolated placental cells obtained from a single individual or placenta, or from a plurality of individuals or placentae.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

In one embodiment, the pharmaceutical composition comprises isolated placental cells that are substantially, or completely, non-maternal in origin, that is, have the fetal genotype; e.g., at least about 90%, 95%, 98%, 99% or about 100% are non-maternal in origin. For example, in one embodiment a pharmaceutical composition comprises a population of isolated placental cells that are $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitate the formation of one or more embryoid-like bodies in a population of placental cells comprising said population of isolated placental cell when said population of placental cells is cultured under conditions that allow the formation of an embryoid-like body; or $OCT-4^+$ and facilitate the formation of one or more embryoid-like bodies in a population of placental cells comprising said population of isolated placental cell when said population of placental cells is cultured under conditions that allow the formation of an embryoid-like body; or a combination of the foregoing, wherein at least 70%, 80%, 90%, 95% or 99% of said isolated placental cells are non-maternal in origin. In another embodiment, a pharmaceutical composition comprises a population of isolated placental cells that are $CD10^+$, $CD105^+$ and $CD34^-$; $CD10^+$, $CD105^+$, $CD200^+$ and $CD34^-$; $CD10^+$, $CD105^+$, $CD200^+$, $CD34^-$ and at least one of $CD90^+$ or $CD45^-$; $CD10^+$, $CD90^+$, $CD105^+$, $CD200^+$, $CD34^-$ and $CD45^-$; $CD10^+$, $CD90^+$, $CD105^+$, $CD200^+$, $CD34^-$ and $CD45^-$; $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitate the formation of one or more embryoid-like bodies in a population of placental cells comprising said isolated placental cells when said population of placental cells is cultured under conditions that allow the formation of an embryoid-like body; $OCT-4^+$ and facilitate the formation of one or more embryoid-like bodies in a population of placental cells comprising said isolated placental cells when said population of placental cells is cultured under conditions that allow the formation of an embryoid-like body; or one or more of $CD117^-$, $CD133^-$, $KDR^-$, $CD80^-$, $CD86^-$, $HLA-A,B,C^+$, $HLA-DP,DQ,DR^-$ and/or $PDL1^+$; or a combination of the foregoing, wherein at least 70%, 80%, 90%, 95% or 99% of said isolated placental cells are non-maternal in origin. In a specific embodiment, the pharmaceutical composition additionally comprises a stem cell that is not obtained from a placenta.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, Plasmalyte, and the like.

5.7.2 Compositions Comprising Hematopoietic Placental Cells or Placental Perfusate Cells In certain embodiments of the compositions provided herein, the isolated placental cells are $CD34^+$ placental stem cells, e.g., hematopoietic placental cells or progenitor cells. Such cells are obtainable from placental tissue, e.g., from a placenta that has been drained of cord blood and perfused to remove residual blood. In certain embodiments, the $CD34^+$ placental stem cells are $CD38^+$. In certain embodiments, the $CD34^+$ isolated placental cells are $CD38^-$. In certain other embodiments, the $CD34^+$ isolated placental cells are $CD45^+$. In a specific embodiment, the isolated placental cells are $CD34^+$, $CD38^-$ and $CD45^+$. In certain embodiments, the cells are hematopoietic cells. In a more specific embodiment, the placental $CD34^+$ cells are hematopoietic cells. In certain embodiments, the $CD34^+$ cells or hematopoietic cells are obtained from placental perfusate. In certain embodiments, the $CD34^+$ cells or hematopoietic cells are obtained enzymatic digestion or physical disruption of placental tissue. The $CD34^+$ cells and hematopoietic cells can be obtained from a single placenta, or from more than one placenta.

In certain embodiments, the cells of the compositions provided herein, formulated by the methods provided herein, are cells obtained from placental perfusate. As used herein, "cells obtained from placental perfusate" includes total nucleated cells obtained from, e.g., isolated from, placental perfusate, a subset of nucleated cells obtained from placental perfusate, or cells cultured or proliferated from cells obtained directly from placental perfusate. Placental perfusate may be obtained from a placenta that has been drained of cord blood and perfused to remove residual blood, prior to perfusion to obtain placental cells. Placental perfusate may be obtained from a placenta that has been drained of cord blood but not perfused to remove residual blood. Placental perfusate may be obtained from a placenta that has neither been drained of cord blood nor perfused to remove residual blood. In the latter two embodiments, the placental cells, e.g., nucleated cells from placental perfusate, for example, total nucleated cells from placental perfusate, comprise nucleated cells from placental blood and/or cord blood. the placental perfusate cells can be obtained from a single placenta, or from more than one placenta.

5.7.3 Immortalized Placental Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^{*}-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present methods. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.7.4 Kits

In another aspect, further provided herein are kits for the production and/or administration of the isolated placental cell-containing compositions of the present invention.

In one embodiment, provided herein is a kit comprising, in separate containers, one or more of a solution comprising dextran, e.g., dextran 40, a solution comprising human serum albumin (HSA), and a cryopreservant. In a specific embodiment, the kit comprises a plurality of isolated placental cells, e.g., cryopreserved isolated placental cells. In a specific embodiment, the kit comprises a container comprising a solution comprising 5.5% dextran 40 (w/v) and 10% HSA (w/v). In another specific embodiment, the kit comprises a container comprising a solution comprising 5.5% dextran 40, 10% HSA and 5% DMSO. In another specific embodiment, the kit comprises a container comprising a solution of 10% dextran 40.

In another embodiment, the kit comprises a filter, or plurality of filters, suitable for filtering cell suspensions. In specific embodiments, one or more of the filters in the kit comprise pores between about 50 µM in diameter to about 150 µM in diameter. In more specific embodiment, the filter is a 70 µM filter. In another specific embodiment, the filter is a 100 µM filter.

In another embodiment, the kit comprises one or more articles of glassware or plasticware suitable for the production or use of one of the compositions described herein. For example, the kit can comprise, e.g., a plastic bag suitable for the cryopreservation or dilution or delivery of a cell suspension, e.g., a suspension of isolated placental cells. In another embodiment, the kit comprises (1) a plurality of isolated placental cells, e.g., placental stem cells or placental multipotent cells, e.g., in one or more vials; (2) plasticware sufficient to culture said isolated placental cells for, e.g., 2-3 passages; (3) a container comprising a solution comprising 5.5% dextran 40 (w/v) and 10% HSA (w/v); (4) a container comprising a solution comprising 5.5% dextran 40, 10% HSA and 5% DMSO; (5) a container comprising a 10% dextran 40 solution; and (6) one or more filters comprising pores between about 50 μM in diameter to about 150 μM in diameter, wherein the filters are suitable for filtering solutions comprising cells.

6. EXAMPLES

6.1 Example 1

Improved Method of Producing Administrable Compositions Comprising Isolated Placental Cells This Example demonstrates formulation of human $CD34^-$, $CD10^+$, $CD105^+$, $CD200^+$ isolated placental cells both before and after cryopreservation, to produce homogenous, high viability isolated placental cells for administration to humans or animals. The resulting composition comprises isolated placental cells that exhibit high viability and no macro cell clumps over at least a 4 hour period post-thaw. An acute dosing mouse study demonstrated that NOD/SCID mice tolerated a maximum dose of at least 1.5 million cells per mouse (approximately 75 million cells per kg assuming an average weight of 20 grams) using the final formulation described below by intravenous infusion administration without any cardiac or pulmonary toxicity (evidenced by labored breathing, circling, and ataxia), and up to 250 million cells per kg subcutaneously, an improvement over previous formulations. While the following example describes formulation of isolated placental cells expressing particular surface markers, the results presented herein indicate that the methods and formulations can be used, and are compatible, with other cells, e.g., mammalian cells expressing different surface markers.

Cell Clump Assays

Cell clumps (aggregations) were classified as macro cell clumps or micro cell clumps. Macro cell clumps and micro cell clumps were identified, if present, according to the following procedures.

Macro Cell Clump Assay

Cells were thawed in a container in a 37° C. water bath until only a tiny piece of ice remained in the container. Cells were drawn from the container using a syringe fitted with a 16 gauge needle, and the cells were dispensed from the container into a 50 mL conical tube. The presence or absence of macro cell clumps was assessed by visual inspection.

Micro Cell Clump Assay

Cells were counted to determine cell concentration. Cells were then diluted to $4\times10^6$ cell/ml with 10% dextran 40, and 50 μL of the cells, 40 μL of 10% dextran 40, and 10 μL of a 40 μM measurement bead solution was added to a 1.7 mL microcentrifuge tube. The contents of the tube were mixed gently. Ten μL of the mixed sample was placed on a glass slide and covered with a cover slip. All micro cell clumps comprising three or more cells were counted.

Placental cells used were initially obtained from a cell bank that contained populations of adherent placental cells, as described herein, that have undergone 4-6 passages prior to cryopreservation.

Data from comparison of in vivo injection compatible buffers, using two different isolated placental cell lines, indicated that phosphate buffered saline (PBS), Plasmalyte A and Dulbecco's Modified Eagle's Medium (DMEM) with the supplement of 1% human serum albumin (HSA) are all able to maintain high viability of cells after 5 hours post-thaw. The final cell concentration in the buffer was $25\times10^6$ cells/ml. Plasmalyte A was selected as promoting the highest viability of cells for the buffers tested. As demonstrated in Table 10a and Table 10b, high viability was maintained for several hours post-thaw; furthermore, nominal phenotypes were not changed over 3 hours post-thaw. Viability of the cells in the post-thaw formulation was not significantly affected after passage of the cells through a 26-gauge needle. A determination of cell clumping in these two experiments was not possible due to the small sample volume used.

Based on the data in Table 1a and Table 1b, the post-thaw formulation was finalized as follows: Cells were thawed at 37° C. in a water bath, and immediately diluted 1:1 (v/v) with thawing buffer (2.5% HSA+5% Dextran 40). The cells were then centrifuged at 400 g for 5 minutes, and resuspended in Plasmalyte A+1% HSA.

TABLE 1a

Post-thaw viability and phenotype of placental cells in Plasmalyte A + 1% HSA without a syringe/needle test.

|  | 0 hour | 1 hour | 3 hour | 5 hour |
|---|---|---|---|---|
| Viability | 98.0% | 97.1% | 92.4% | 93.8% |
| CD105+/200+ | 84.3% |  | 87.9% |  |

TABLE 1b

Post-thaw viability and phenotype of placental cells in Plasmalyte A + 1% HSA with a syringe/needle test.

|  | 0 hour | 1 hour | 3 hour | 5 hour |
|---|---|---|---|---|
| Viability | 98.0% | 97.2% | 93.7% | 97.3% |
| CD105+/200+ | 87.3% |  | 87.3% |  |

Mouse Biodistribution Study

The above post-thaw formulation was applied in a pilot mouse biodistribution study. Macro cell clumps were observed during post-thaw cell preparation, especially after the addition of Plasmalyte. With this cell preparation, acute pulmonary toxicity was observed at a dose of 1 million cells per mouse (around 20 g) by two repeat intravenous infusions of 0.5 million cells each. These two observations prompted further investigation of the placental cell formulation.

Based upon the observations from a pilot mouse biodistribution study that significant cell clumps were induced after the addition of Plasmalyte A, but not Dextran 40, Dextran 40 was used for this study as a dilution medium, along with Plasmalyte A, HSA and PBS.

TABLE 2

Cell clumps ranking at 4 hours post-thaw.
Lower numbers indicate fewer clumps.

| | Medium | | | |
|---|---|---|---|---|
| | 5% Dextran 40 + 10% HSA | 5% Dextran 40 + 2.5% HSA | 5% Dextran 40 | PBS | Plasmalyte A |
| Cell clump rank | 1 | 1 | 2 | 3 | 3 |

Cells, previously frozen in Plasmalyte A+10% HSA+5% DMSO, were thawed in a 37° C. water bath, and diluted 1:7 with the respective buffers. The data in table 2 shows that Dextran 40 with HSA induced the fewest cell clumps among the media tested.

Cell aggregates were observed immediately post-thaw in various formulations. Addition of a filtration step, wherein post-thaw cells were filtered through a 100 μm filter, eliminated cell aggregates. Two lots of placental cells were tested for the effect of filtration in combination with specific diluents. No macro cell clumps were formed post-filtration when cells were 1:1 diluted with 10% Dextran 40 over a time period of 4 hours post-thaw. See Tables 3a-3c. In addition, viability remained high. Similar results were observed across several different lots of placental cells.

TABLE 3a

Macro cell clump

| | LOT 1 | | LOT 2 | |
|---|---|---|---|---|
| Existing macro cell clump in bag post-thaw | Yes, large sheets | | Yes, small dots | |
| Newly formed macro cell clump post-filtration | Plasmalyte A | 5% Dextran 40 | Plasmalyte A | 5% Dextran 40 |
| | Yes | No | Yes, but much fewer than LOT 1 | No |

TABLE 3b

Micro cell clump post-filtration in Dextran 40

| | LOT 1 | LOT 2 |
|---|---|---|
| 3-5 cell clump (clumps/$10^6$ cells) | 1210 | 416 |
| 5 cell clump (clumps/$10^6$ cells) | 491 | 119 |

TABLE 3c

Viability post-filtration in Dextran 40 and Plasmalyte A

| | LOT 1 | | LOT 2 | |
|---|---|---|---|---|
| | Dextran 40 | Plamalyte A | Dextran 40 | Plasmalyte A |
| 0 hr | 91.5% | 92.4% | 94.2% | 94.5% |
| 2 hr | 92.5% | 93.9% | | |
| 4 hr | 91.8% | 94.7% | 94.7% | 93.3% |

On the basis of the foregoing studies, the post-thaw formulation placental cells was simplified to the following procedure: Cells were thawed at 37° C. water bath for up to 3 minutes, then filtered through a 100 μM strainer. The strained cells were then diluted 1:1 (v:v) with 10% dextran 40.

Pre-Freeze Formulation

Cell clumps were also observed in the pre-freeze phase of cell processing. Freezing medium, freezing cell density and a suspension filtration step were studied to reduce and/or eliminate cell aggregates prior to freezing.

Freezing Medium

Based upon the success of Dextran 40 in the post-thaw formulation, above, Dextran 40 was compared with Plasmalyte as a freezing medium. Cells from LOT 3 were frozen at a concentration of 17 million cells per mL in either Plasmalyte A+10% HSA+5% DMSO or in 5% Dextran 40+10% HSA+5% DMSO. The presence of cell clumps was evaluated as follows:

TABLE 4a

Comparison of Plasmalyte and Dextran 40 as freezing medium - Macro cell clumps

| | Plasmalyte A | Dextran 40 |
|---|---|---|
| Macro cell clump | More than Dextran 40 | Fewer than Plasmalyte A |
| Cell loss after filtration with 100 μm strainer | 20% | 3% |

TABLE 4b

Comparison of Plasmalyte A and Dextran 40 as freezing medium - Micro cell clumps

| | Plasmalyte A | Dextran 40 |
|---|---|---|
| 3-5 cell clump (clumps/$10^6$ cells) | 1893 | 523 |
| >5 cell clump (clumps/$10^6$ cells) | 929 | 205 |

TABLE 4c

Comparison of Plasmalyte A and Dextran 40 as freezing medium - Viability

| | Plasmalyte | Dextran 40 |
|---|---|---|
| 0 hour post-thaw | 89.9% | 90.8% |
| 4 hour post-thaw | 89.2% | 91.3% |

The use of Dextran 40 in these experiments resulted in fewer macro cell clumps, fewer micro cell clumps, and higher cell viability than the use of Plasmalyte A. On the basis of these results, Dextran 40 was selected as the freezing medium.

Freezing Cell Density and Pre-Freeze Filtration

In order to eliminate macro cell clumps and minimize micro cell clumps, cell density and pre-freeze filtration were examined as follows:

TABLE 5a

The effect of freezing cell density and pre-freeze filtration on cell clump formation.

|  | Condition 1 | Condition 2 | Condition 3 | Condition 4 |
|---|---|---|---|---|
| Filtration | Yes, 70 μm strainer | No | Yes, 70 μm strainer | No |
| Concentration | $20 \times 10^6$ | $20 \times 10^6$ | $5 \times 10^6$ | $5 \times 10^6$ |
| Freezing medium | 5% Dextran 40 + 10% HSA + 5% DMSO | 5% Dextran 40 + 10% HSA + 5% DMSO | 5% Dextran 40 + 10% HSA + 5% DMSO | 5% Dextran 40 + 10% HSA + 5% DMSO |

Concentration: cells per milliliter.

TABLE 5b

The effect of freezing cell density and pre-freeze filtration on macro cell clump formation.

|  | Condition 1 | Condition 2 | Condition 3 | Condition 4 |
|---|---|---|---|---|
| Pre-freeze filtration | No | Yes | No | Yes |
| Post-thaw filtration | No | Yes | No | Yes |

No: No macro clump formation.
Yes: Macro clump formation.

TABLE 5c

The effect of freezing cell density and pre-freeze filtration on micro cell clump (clumps per $10^6$ cells)

|  | Condition 1 | | Condition 2 | | Condition 3 | | Condition 4 | |
|---|---|---|---|---|---|---|---|---|
|  | 3-5 cell micro cell clumps | >5 cell micro cell clumps | 3-5 cell micro cell clumps | >5 cell micro cell clumps | 3-5 cell micro cell clumps | >5 cell micro cell clumps | 3-5 cell micro cell clumps | >5 cell micro cell clumps |
| Pre-freezing | 188 | 0 | 291 | 194 | 231 | 46 | 237 | 172 |
| Post-thaw | 688 | 375 | 631 | 655 | 231 | 116 | 323 | 366 |

The results shown in Tables 5b and 5c clearly show that pre-freeze filtration eliminated post-thaw macro cell clump formation. The data also indicate that samples with high cell concentration, e.g., $20 \times 10^6$ cells/ml, have more potential to form micro cell clumps post-thaw. As a result, the effect of freezing cell density on cell clump formation was examined further.

TABLE 6a

Effect of freezing cell density on cell clump formation

| LOT 4 | Condition 1 | Condition 2 | Condition 3 | Condition 4 |
|---|---|---|---|---|
| Concentration | $15 \times 10^6$ | $10 \times 10^6$ | $7.5 \times 10^6$ | $5 \times 10^6$ |
| Filtration | 70 μm strainer | 70 μm strainer | 70 μm strainer | 70 μm strainer |
| Freezing medium | 5% Dextran 40 + 10% HSA + 5% DMSO | 5% Dextran 40 + 10% HSA + 5% DMSO | 5% Dextran 40 + 10% HSA + 5% DMSO | 5% Dextran 40 + 10% HSA + 5% DMSO |

Concentration: number of cells per milliliter.

TABLE 6b

Effect of freezing cell density on macro cell clump formation

|  | Condition 1 | Condition 2 | Condition 3 | Condition 4 |
|---|---|---|---|---|
| Pre-freezing | Yes (1 clump) | No | No | No |
| Post-thaw 0 h | Yes (3 clumps) | Yes (1 clump) | No | No |
| Post-thaw 4 h | Yes (3 clumps) | Yes (1 clump) | No | No |

No: No macro cell clump formation.
Yes: Macro cell clump formation

TABLE 6c

The effect of freezing cell density on micro cell clump (clumps per $10^6$ cells)

|  | Condition 1 | | Condition 2 | | Condition 3 | | Condition 4 | |
|---|---|---|---|---|---|---|---|---|
|  | 3-5 cell | >5 cell | 3-5 cell | >5 cell | 3-5 cell | >5 cell | 3-5 cell | >5 cell |
| Pre-freezing | 141 | 70 | 130 | 65 | 83 | 33 | 103 | 34 |
| Post-thaw 0 h | 271 | 193 | 111 | 44 | 102 | 34 | 108 | 46 |
| Post-thaw 4 h | 298 | 212 | 105 | 53 | 122 | 44 | 97 | 55 |

The results in Tables 6b and 6c demonstrate that freezing density at $7.5 \times 10^6$/ml or less does not induce post-thaw macro cell clumps. Furthermore, at concentrations up to $10 \times 10^6$ cells/ml, the number of micro cell clumps is reasonably low, at less than 200 micro cell clumps/million cells.

Based on the above results, the pre-freeze and post-thaw formulations were generated as follows. For pre-freeze formulation, placental cells from liquid culture were centrifuged at 220×g for 5 minutes, and resuspended in 5% Dextran 40 to about $7.5 \times 10^6$ cells/mL. The cells were centrifuged at 400×g for 10 minutes, then resuspended in 6% Dextran 40 and 10% HSA to about $7.5 \times 10^6$ cells/mL. The resuspended cells were then passed through a 70 μM filter by gravity. Filtered cells were then diluted in 5% Dextran 40, 10% HSA, and 5% DMSO to a concentration of about $7.5 \times 10^6$ cells per mL. The diluted cells were placed in cryo-bags, frozen, and stored under vapor phase nitrogen. For post-thaw formulation, frozen cells were thawed in a 37° C. water bath, then diluted with 10% dextran 40 at various volume ratios from 1:1 to 1:5 of cell-containing buffer: dextran 40

Assessment of Placental Cell Formulation

1. No Post-Thaw Macro Cell Clump Formation

Five lots of placental cells were produced using the above formulation method (including LOT 11 and LOT 12, described below). Macro cell clumps post-thaw were not observed in any of the five lots, and the number of micro cell clumps remained low.

2. No Impact on Phenotype

The phenotype of the placental cells was not affected by the improved formulation. More than 90% of cells in the formulation remained CD10$^+$, CD34$^-$, CD105$^+$ and CD200$^+$.

3. GLP Mouse Studies

LOT 12 cells were used for a mouse biodistribution study. Placental cells were administered in the above formulation as a single and/or repeat intravenous tail vein injection to both male and female NOD-SCID or male C57BL/10SgSnAi-Rag2(tmi)γc(tmi) mice. The mice were sacrificed at 4, 14, 28 or 47 days post-treatment and samples of lung, liver, heart, kidneys, spleen, adrenal glands, bone marrow, and brain were processed and analyzed by Q-PCR for the presence of the hTERT DNA sequence; hTERT is the human telomerase reverse transcriptase gene. Following i.v. administration, human DNA was detected in isolated total DNA from samples of lung, brain, heart and/or liver in mice that were sacrificed at 4 days after dosage administration. The highest levels of DNA were detected in the lung. Mice were able to tolerate 25-100 million cells per kg administration by intravenous infusion without any cardiac or pulmonary toxicity. LOT 11 cells were used for a tumorigenicity mouse study. Mice were administered up to 250 million cells per kg subcutaneously (SC) with no adverse effects.

6.2 Example 2

Improved Administrable Compositions

This Example demonstrates a formulation of human multipotent tissue culture plastic-adherent CD34$^-$, CD10$^+$, CD105$^+$, CD200$^+$ placental cells, that even post-cryopreservation, represent homogenous, high viability cells suitable for administration to humans or animals. The cells of the formulation exhibit on average a 400-fold decrease in the amount of aggregates formed, and an improved Maximum Tolerated Dose (MTD) of approximately 3-fold improvement over a previous formulation in an intravenous mouse model (data not shown). While the following example describes formulation of isolated placental cells expressing particular surface markers, the results presented herein indicate that the methods and formulations can be used, and are compatible, with other cells, e.g., mammalian cells expressing different surface markers.

The formulation (designated "Formulation B") comprises placental cells of the above cellular phenotype at a concentration of $10 \pm 3 \times 10^6$ cells/mL, in a solution containing 5.5% (w/v) Dextran 40, 10% (w/v) Human Serum Albumin (HSA), and 5% (v/v) dimethyl sulfoxide (DMSO). The HSA and Dextran 40 used herein are clinical grade; DMSO is GMP grade.

A Plasmalyte-based formulation designated "Formulation A," is described and compared to Formulation B, a Dextran 40 based formulation, in Table 7. Cells are filtered in suspension through a 70 μm mesh in the preparation of Formulation B, but are not filtered in preparation of Formulation A.

TABLE 7

Composition of Formulation A and Formulation B

|  | Formulation A | Formulation B |
|---|---|---|
| Cell concentration | $27 \pm 8 \times 10^6$ cells/mL | $10 \pm 3 \times 10^6$ cells/mL |
| Bulk excipient | Plasmalyte | 5.5% Dextran 40 in saline |
| DMSO concentration | 5% (v/v) | 5% (v/v) |
| HSA concentration | 10% | 10% |

Significant cell aggregation was observed when thawing Formulation A. Subsequent investigation showed that a number of parameters, including the composition of the formulation medium and the freezing concentration of the cells were key contributors to cell aggregation. Optimization studies were conducted and Formulation B was designed specifically to reduce or eliminate these cell aggregation effects. In addition, the filtration of the cell suspension through a 70 μm mesh as part of the process was introduced to provide better control of cell suspensions during formulation.

To quantify cell aggregates in the formulations, a filter retention assay was devised as a development tool and used to compare a series of placental cell composition batches produced by both Formulation A and Formulation B. This became particularly critical since the cell aggregation in Formulation B was reduced to the point where it was no longer reliably discernable by naked eye. A comparison of multiple samples analyzed from representative batches of Formulation A and Formulation B is shown in Table 8. The method quantifies the pre-stained cell aggregates retained on a filter from different samples by digital imaging of the filter, and reports the area of filter ("Mean Area") covered by the aggregates. As shown in Table 8, Formulation B had consistently less area coverage (aggregates) than Formulation A, with the average difference being 400-fold. The data also show good process control and reproducibility for Formulation B. Isolated placental cell composition lots of the two formulations used for in vivo studies are also indicated in Table 16. The change from Formulation A to Formulation B improved the Maximum Tolerated Dose (MTD) approximately 3-fold in an intravenous in vivo mouse model (data not shown).

TABLE 8

Post-Thaw Aggregate formation in Formulation A and Formulation B

| Lot | Bags | Filters | Mean Area (px/MM) | Std Dev | CV | Formulation (in vivo testing indicated by *) |
|---|---|---|---|---|---|---|
| 1 | 2 | 13 | 97490 | 38369 | 0.39 | Formulation A |
| 2 | 1 | 12 | 98629 | 33165 | 0.34 | Formulation A* |
| 1 | 1 | 2 | 63 | 81 | 1.28 | Formulation B* |
| 2 | 1 | 2 | 38 | 12 | 0.32 | Formulation B |
| 3 | 1 | 2 | 1539 | 573 | 0.37 | Formulation B* |
| 4 | 1 | 2 | 137 | 43 | 0.31 | Formulation B |
| 5 | 3 | 6 | 125 | 162 | 1.29 | Formulation B |
| 6 | 3 | 6 | 71 | 57 | 0.81 | Formulation B |

Key:
"Bags" indicates the number of isolated cell composition bags thawed and tested for that Lot; "Filters" indicates the total number of assay replicates for that Lot; "Mean Area" indicates the mean area coverage of the filters for that Lot in units of pixels/million cells applied to the filter; "Std Dev" = standard deviation; "CV" = Coefficient of Variation.

6.3 Example 3

Characterization of Improved Administrable Compositions

This Example provides further characterization of pharmaceutical formulations comprising HSA, dextran 40, and DMSO. Methods used in one or more of the experiments described below are as follows:

Cellular viability assessment: Viability was assessed by a Trypan Blue exclusion assay using either a hemocytometer or a Vi-Cell cell viability analyzer (Beckman Coulter, Fullerton, Calif.). Viability was expressed as a percentage viable cells out of total cells.

Cell counts: Cells were counted using either a hemocytometer or a Vi-Cell cell viability analyzer (Beckman Coulter, Fullerton, Calif.). Cell counts are expressed as millions of cells per milliliter (MM/mL).

Cellular aggregation: The amount of cellular aggregation was measured using a Filter Retention Assay (FRA), which measures the amount of cellular aggregation by staining cells and passing them through a 70 μm filter. Cellular aggregates greater than 70 μm cannot pass the filter and are quantified by image analysis using a Vi-Cell cell viability analyzer (Beckman Coulter, Fullerton, Calif.). Data are expressed in pixels per million cells loaded (px/MM).

Flow cytometry: Cells were assessed for the levels of the cellular markers CD10, CD34, CD105 and CD200 by flow cytometry. Values are expressed as a percentage of cells positive and/or negative for a particular marker, or combination of markers.

Immunosuppression: The immunosuppressive activity of cells in the formulations described below was assessed using a Bead T-cell Reaction (BTR) assay, which measures the ability of cells to suppress a T-cell response to antigenic beads.

While the following example describes formulation of isolated placental cells expressing particular surface markers, the results presented herein indicate that the methods and formulations can be used, and are compatible, with other cells, e.g., mammalian cells expressing different surface markers.

6.3.1 Characterization of DMSO and Dextran:HSA Ratios

This example describes the effect of varying the concentrations of HSA, Dextran, and DMSO, and of varying the ratio of dextran to HSA, on cellular aggregation, cell viability and recovery, and cell phenotype and functionality.

Experimental Conditions

The three component (HSA, dextran 40 and DMSO) solution space for the cell formulation was investigated at the conditions shown on the ternary diagram in FIG. 1. Experimental conditions were chosen along two axes: one which tested different percentages of DMSO while holding the Dextran:HSA ratio constant (see formulations 1-4, below), and another that varied the ratio of Dextran:HSA while holding the percentage of DMSO constant (see formulations 3, 5-8, below).

Methods and Materials

Approximately twelve million cryopreserved $CD10^+$, $CD34^-$, $CD105^+$, $CD200^+$ placental multipotent cells were expanded in Nunc™ 10-tray Cell Factories, one for each of the formulations below, to approximately $1.2 \times 10^8$ cells. Cells were harvested by incubation for 10 min. at room temperature with 0.25% Trypsin/EDTA. Dissociated cells were transferred to a 500 mL centrifuge tube containing 250 mL of 2% fetal bovine serum (FBS) in Dulbecco's Modified Eagle's Medium (DMEM). Cells were then centrifuged at 1040 RPM in 500 mL tubes in a Sorvall RC3BP centrifuge. Cells were re-suspended in a 0.9% saline/5% dextran 40 solution. The cells were then centrifuged at 1420 RPM for 10 min, and suspended in 10 mL of one of the following eight formulations (dextran:HSA ratios are displayed in units of "volume fraction of 25% HSA" (VF HSA) for formulations and 5-8):

Formulation 1: 20% DMSO, 8.5% HSA, 4.6% dextran 40
Formulation 2: 10% DMSO, 9.5% HSA, 5.2% dextran 40
Formulation 3: 5% DMSO, 10% HSA, 5.5% dextran 40 (VF HSA=0.4) (control formulation)
Formulation 4: 0% DMSO, 10.5% HSA, 5.8% dextran 40
Formulation 5: 5% DMSO, 0% HSA, 9.5% dextran 40 (VF HSA=0)
Formulation 6: 5% DMSO, 3.125% HSA, 8.25% dextran 40 (VF HSA=0.125)
Formulation 7: 5% DMSO, 16.88% HSA, 2.75% dextran 40 (VF HSA=0.675)
Formulation 8: 5% DMSO, 23.75% HSA, 0% dextran 40 (VF HSA=0.95)

The formulations were prepared from the following stock solutions: 100% DMSO (Bioniche Pharma, Belleville, Ontario), 25% HSA (Octapharma, Hoboken, N.J.) and 10% dextran 40 in 0.9% Saline (Hospira, Lake Forest, Ill.).

Filter Retention Assay: Cellular aggregation was assessed through the use of filter retention assay. Cell concentration was adjusted to approximately $1.2 \times 10^7$ cells/mL prior to filtration. Filter load (number of cells per unit filter area) was held constant at approximately $2.4 \times 10^8$ cells/filter. Cells were cryopreserved in a Thermo control rate freezer to $-70°$ C. at a concentration of $7.5 \times 10^6$ cells/mL. Cells were thawed prior to use, and samples were processed shortly after thaw. A 100 µL sample of the undiluted cell suspension was taken post thaw, diluted with 900 µL of phosphate buffered saline (PBS), and cell counts were performed in duplicate using a Vi-Cell cell viability analyzer (Beckman Coulter, Fullerton, Calif.) and reported as numbers of pixels per million cells (higher numbers of pixels indicate higher numbers of cellular aggregates).

Cell viability assay (AMTS assay): Cell viability was determined using a CellTiter 96® Non-Radioactive Cell Proliferation Assay (Promega, Madison, Wis.). Cells in 96-well plates were combined with (3-(4,5-dimethylthiazol-2-yl)-5-(3-carboxymethoxyphenyl)-2-(4-sulfophenyl)-2H-tetrazolium) (MTS) and phenazine methosulfate (PMS), an electron coupling reagent, according to manufacturer's directions. Absorbance at 490 nm of the resulting formazan product, produced by cellular bioreduction of MTS, was then determined.

Annexin well plate assay: Thawed cells were diluted to a concentration of $1 \times 10^5$ cells/mL in an Annexin-V Labeling solution (Roche, Cat. No. 11 828 681 001). 100 µL of the cell suspension was added to a 96 well plate in triplicate and incubated for 15 minutes at room temperature with no exposure to light. After 15 minutes, three different positions within each well were imaged under brightfield and fluorescent light (excitation wavelength of 488 nm and detection at wavelength 528 nm). An automated cell counting software (Axiovision) was used to count total cells per image. Apoptotic/necrotic cell populations were determined by counting Annexin positive cells at each position (fluorescent image) and dividing by total cells at each position (brightfield image). Apoptotic/necrotic cell populations per condition were determined by averaging the computed populations in three different well positions of 3 wells.

Results
Cellular Aggregation

Across varying percentages of DMSO, e.g., 0 to 20 percent (formulations 1-4), no effect on cellular aggregation was observed, as shown in FIG. 2. All DMSO conditions exhibited levels of aggregation within the range observed for the control formulation comprising 5% DMSO, 5.5% dextran 40 and 10% HSA. HSA and Dextran concentrations were also varied at a constant 5% DMSO concentration (FIG. 3), with conditions ranging from no HSA (HSA volume fraction=0) to no Dextran (HSA volume fraction=0.95). FRA values across volume fractions of 0.125 to 0.95 of 25% HSA (final concentration 3.125% to 23.75% HSA, respectively) indicated minimal aggregation. Observed levels of aggregation in the presence of HSA were equal to or below the control formulation comprising 5% DMSO, 5.5% dextran 40 and 10% HSA.

Post Thaw Viability and Recovery

Post thaw viability (FIG. 4) and post thaw recovery (FIG. 5) across different percentages of DMSO (0, 5, 10 and 20%) was measured through trypan blue exclusion, using the Vi-Cell automated cell counter, to assess the cryoprotective capabilities of each formulation. Post thaw viability was greater than 90% with formulations comprising 0%, 5% and 10% DMSO, respectively, with a maximum value observed at 5% DMSO, while viability was below 75% with a formulation comprising 20% DMSO. Culture re-establishment was measured through the MTS assay. Culture re-establishment was observed to be maximal at 5% DMSO (FIG. 6).

The viability profile across the different volume fractions of 25% HSA, i.e., differing ratios of dextran:HSA, is shown in FIGS. 7-9. Post thaw viability, as determined by Trypan blue exclusion, exhibited values ranging from 83.5% to 98.5% across the various volume fractions of HSA (FIG. 7). A maximum value was achieved at a 0.40 fraction of 25% HSA, i.e., 10% HSA: 5.5% Dextran 40. Post thaw cell recovery was also calculated, and values ranged from 80% to 120%, though samples comprising at least 0.2 volume fraction of 25% HSA exhibited values ranging from 100% to 120% (FIG. 8). The culture re-establishment data, as determined by MTS assay, exhibit a similar profile to that of post thaw viability, with maximum value occurring at a 0.125 fraction of 25% HSA, i.e., 3.13% HSA: 8.25% Dextran 40 (FIG. 9).

Trypan viability does not have the ability to detect apoptotic cells. However analysis of the cell size distributions may indicate changes in cell health. To estimate the percent of apoptotic cells in cell populations thawed from cells frozen in the absence of DMSO, a post thaw well plate annexin assay was conducted. The assay estimated that 51% of the cells frozen in 0% DMSO were apoptotic as opposed to 15% apoptotic when frozen in 5% DMSO (data not shown).

Phenotype and Functionality

The ability to maintain the cells' $CD10^+$, $CD34^-$, $CD105^+$, $CD200^+$ phenotype was tested across the different percentages of components by flow cytometry. Cells formulated in formulation 2 (10% DMSO, 9.5% HSA, 5.2% dextran 40), formulation 5 (5% DMSO, 0% HSA, 9.5% dextran 40), formulation 6 (5% DMSO, 3.13% HSA, 8.25% dextran 40) and formulation 7 (5% DMSO, 16.88% HSA, 2.75% dextran 40) maintained this phenotype approximately as well as control formulation 3, and had $CD105^+/CD200^+$ values between 80.3% and 84.5%. Additionally, $CD10^+/CD34^-$ expression was >95% for each formulation. Conditions 1, 4 and 8 indicated a change in the cells' physical characteristics, possibly because debris affected the flow cytometric assay.

Cell functionality was assessed through the Bead T cell Reaction (BTR) assay, which measures the ability of cells to suppress a T cell response to antigenic beads (FIG. 10). Formulation 6 (5% DMSO, 3.13% HSA, 8.25% dextran 40), and formulation 7 (5% DMSO, 16.88% HSA, 2.75% dextran 40) had suppression within 1 standard deviation of a control formulation 3 comprising 5% DMSO/10% HSA and 5.5% dextran 40. These three samples had the highest trypan blue viabilities and culture re-establishment values. The other samples had lower levels of suppression, with a reduction that generally correlated with decreased MTS.

Conclusions:

Formulations comprising DMSO concentrations ranging from 0 to 20% exhibit levels of cellular aggregation comparable to that observed for a control formulation comprising 5% DMSO, 10% HSA, and 5.5% dextran 40. However, cell viability was reduced when cells were cryopreserved in formulation comprising 20% DMSO, and cells frozen in 0% DMSO exhibited significantly enhanced apoptosis post-thaw relative to cells frozen in 5% DMSO. There was no appreciable degradation of CD $10^+$, $CD34^-$, CD $105^+$, $CD200^+$ phenotype for formulations comprising 5% and 10% DMSO. Thus, the results above demonstrate that use of formulations comprising 5-10% DMSO is preferred for maintaining post-thaw viability.

With respect to varying the ratio of HSA:dextran, formulations comprising 23.75% HSA, 0% dextran exhibited some reduction in post-thaw viability and culture re-establishment, while post-thaw viability, immunosuppressive activity and re-establishment values were highest for formulations comprising dextran:HSA ratios of: (i) 3.13% HSA to 8.25% dextran; (ii) 10% HSA to 5.5% dextran; and (iii) 16.88% HSA to 2.75% dextran. Thus, these results demonstrate that the HSA:dextran ratio of the formulations described herein may be varied within a defined a range without an appreciable loss of cell viability, cell recovery after thawing, degradation of $CD10^+$, $CD34^-$, $CD105^+$, $CD200^+$ phenotype, or immunosuppressive activity, relative to formulations comprising an HSA:dextran ratio of 10% HSA and 5.5% Dextran 40. The data presented herein support a working range of HSA:dextran ratios of at least between about 6:1 HSA:dextran to about 1:2.6 HSA:dextran.

6.3.2 Effect of Freezing Cell Density

This example describes the effects of cell concentration, e.g., freezing cell densities ranging from $1$–$40 \times 10^6$ cells/mL, on cell viability; $CD10^+$, $CD34^-$, $CD105^+$, $CD200^+$ phenotype; cellular aggregation; and immunosuppressive functionality of the cells.

Methods and Materials $CD10^+$, $CD34^-$, $CD105^+$, $CD200^+$ placental stem cells were cultured for 3 days, harvested, centrifuged, and re-suspended in formulation comprising 5% DMSO, 5.5% dextran 40, 10% HSA to a concentration of about $3.5 \times 10^7$ cells/mL, and filtered through a 70 μm filter. The post-filter cells were serially diluted in the above formulation to create cell samples comprising, in sterile bags, the following cell densities: $1 \times 10^6$ cells/mL, $7.5 \times 10^6$ cells/mL, $15 \times 10^6$ cells/mL, and $20 \times 10^6$ cells/mL. Cells were harvested separately to create a separate cell sample comprising $4.0 \times 10^7$ cells/mL. Cells of the $4.0 \times 10^7$ cells/mL sample were re-suspended in 5 mL of formulation comprising 5% DMSO, 5.5% dextran 40, 10% HSA to a concentration of about $4.6 \times 10^7$ cells/mL, filtered through a 70 μm filter, and diluted to $4.0 \times 10^7$ cells/mL in a 20 mL bag using the above formulation. One 20 mL bag of the $4.0 \times 10^7$ cells/mL sample, duplicate 20 mL bags of the $1 \times 10^6$ cells/mL, $7.5 \times 10^6$ cells/mL, $15 \times 10^6$ cells/mL, and $20 \times 10^6$ cells/mL samples, and five 280 μL vials of each sample were frozen at −70° C. using a controlled rate freezer. These samples were later thawed and analyzed to determine the effects of freezing concentration on various cellular characteristics, including (1) cell count; (2) viability; (3) phenotype; (4) cell aggregation; and (5) potency.

Filter Retention Assay: Cellular aggregation was assessed through the use of filter retention assay. Cell concentration was adjusted to approximately $1.2 \times 10^7$ cells/mL prior to filtration. Filter load (number of cells per unit filter area) was held constant at approximately $2.4 \times 10^8$ cells/filter. Cells were cryopreserved in a Thermo control rate freezer to −70° C. at a concentration of $7.5 \times 10^6$ cells/mL. Cells were thawed prior to use, and samples were processed shortly after thaw. A 100 μL sample of the undiluted cell suspension was taken post thaw, diluted with 900 μL of phosphate buffered saline (PBS), and cell counts were performed in duplicate using a Vi-Cell cell viability analyzer (Beckman Coulter, Fullerton, Calif.) and reported as numbers of pixels per million cells (higher numbers of pixels indicate higher numbers of cellular aggregates).

Results:

Cell Count/Viability

One to two 1 mL samples from each thawed bag were taken for viable cell counts and viability determination using a Vi-Cell cell viability analyzer (Beckman Coulter, Fullerton, Calif.) according to manufacturer's directions. The average viability remained constant for all the conditions, at about 97%. The viable cell count corresponded to the initial freezing concentration (see Table 9 below).

TABLE 9

Vi-Cell viable cell concentration and viability

| Freezing Concentration | Cell count ($\times 10^6$) cells/mL | Viability (%) |
|---|---|---|
| $1 \times 10^6$/mL | 1.20 | 98.70 |
| $7.5 \times 10^6$/mL | 8.32 | 97.12 |
| $15 \times 10^6$/mL | 16.47 | 97.33 |
| $20 \times 10^6$/mL | 20.80 | 97.61 |
| $40 \times 10^6$/mL | 39.92 | 96.71 |

Phenotype

The ability to maintain the cells' $CD10^+$, $CD34^-$, $CD105^+$, $CD200^+$ phenotype was tested across the different cell densities by flow cytometry. As presented in Table 10, the phenotype does not change between different freezing concentrations. $CD200^+/CD105^+$ expression remained around 86% and $CD34^-/CD10^+$ expression remained around 99% for all conditions.

TABLE 10

CD200+/CD105+ and CD34−/CD10+ expression

| Freezing concentration | $CD200^+/CD105^+$ | $CD34^-/CD10^+$ |
|---|---|---|
| $1 \times 10^6$/mL | 87.3 | 98.2 |
| $7.5 \times 10^6$/mL | 86.7 | 99.1 |
| $15 \times 10^6$/mL | 85.8 | 99.1 |

TABLE 10-continued

CD200+/CD105+ and CD34−/CD10+ expression

| Freezing concentration | CD200$^+$/CD105$^+$ | CD34$^-$/CD10$^+$ |
|---|---|---|
| 20 × 10$^6$/mL | 85.5 | 98.9 |
| 40 × 10$^6$/mL | 86.3 | 98.5 |
| Negative control | 69.4 | 98.5 |
| Positive control | 91.1 | 98.8 |

Cellular Aggregation

Replicates of each condition were analyzed by a Filter Retention Assay to determine the degree of cellular aggregation at different freezing concentrations (FIG. 11). Duplicates of the assay were performed for the 1×10$^6$ cells/mL, 7.5×10$^6$ cells/mL, 15×10$^6$ cells/mL and 20×10$^6$/mL samples. One cell sample was assayed in duplicate for the 40×10$^6$ cells/mL sample. The 40×10$^6$ cells/mL sample produced the highest cellular aggregation signal for all cell densities tested. All of the other samples were at or below the amount of aggregation observed with a control sample previously cryopreserved at 7.5×10$^6$ cells/mL in 5% DMSO, 5.5% dextran 40, 10% HSA.

An additional, separate cellular aggregation assay was performed to test cells cryopreserved in formulation comprising 5% DMSO, 5.5% dextran 40, 10% HSA at 7.5×10$^6$/mL and 20×10$^6$/mL (FIG. 12). The additional data showed an increased signal at 20×10$^6$/mL, indicating that cells frozen at 20×10$^6$/mL give variable cellular aggregation results. As a result, cells frozen at this concentration or higher have an increased potential for aggregation. These data demonstrate that aggregation increases with increasing cell concentration, and a freezing cell density of 20×10$^6$ mL can show increases in cellular aggregation relative to a freezing cell density of 7.5×10$^6$/mL.

Functionality

A vial from each condition was used for mixed leukocyte reaction (MLR) and bead T-cell reaction (BTR) analysis to assess the immunomodulatory properties of the cells at varying freezing cell densities, as measured by suppression of proliferation of CD4$^+$ T cells and CD8$^+$ T cells. The MLR results indicate a dip in CD4 and CD8 suppression at 15×10$^6$ cells/mL and 40×10$^6$ cells/mL, though suppression at 20×10$^6$ cells/mL was comparable to that observed at 1×10$^6$ cells/mL and 7.5×10$^6$ cells/mL. However, the BTR results show a reduction in CD4 and CD8 suppression at 20×10$^6$ cells/mL and 40×10$^6$ cells/mL.

TABLE 11

MLR and BTR results - percent T cell reactivity compared to T cell reactivity in the absence of placental stem cells.

| | MLR | | BTR | |
|---|---|---|---|---|
| Sample | CD4 Suppression | CD8 Suppression | CD4 Suppression | CD8 Suppression |
| 1 × 10$^6$/mL | 63 | 64 | 63 | 62 |
| 7.5 × 10$^6$/mL | 63 | 64 | 63 | 62 |
| 15 × 10$^6$/mL | 49 | 46 | 61 | 64 |
| 20 × 10$^6$/mL | 65 | 65 | 36 | 39 |
| 40 × 10$^6$/mL | 40 | 45 | 33 | 38 |

Conclusions:

The results above demonstrate that cell viability and CD10$^+$, CD34$^-$, CD105$^+$, CD200$^+$ phenotype does not change as a function of freezing cell density. However, cells cryopreserved at a density of 20×10$^6$ cells/mL demonstrated a variable increase in cellular aggregation and a variable decrease in immunosuppressive activity, while cells cryopreserved at a density of 40×10$^6$ cells/mL exhibited a consistent increase in cellular aggregation and a consistent decrease in immunosuppressive activity. As such, while cells may be formulated in the formulations described herein at a density of up to, e.g., 40×10$^6$ cells/mL without an appreciable decrease in cell viability or in the number of cells displaying a CD10$^+$, CD34$^-$, CD105$^+$, CD200$^+$ phenotype, a freezing cell density in the range of 1.0–15×10$^6$ cells/mL is preferable for minimizing cellular aggregation upon thaw.

6.3.3 Effect of Molecular Weight of Dextran

This Example describes the effect of varying molecular weights of dextran, e.g., dextran 1 (MW=1000), dextran 40 (MW=40,000) and dextran 70 (MW=70,000) on cellular aggregation, viability, recovery, CD10$^+$, CD34$^-$, CD105$^+$, CD200$^+$ phenotype and functionality.

Materials and Methods

Twelve million cryopreserved CD 10$^+$, CD34$^-$, CD105$^+$, CD200$^+$ placental multipotent cells were expanded in Nunc™ 10-tray Cell Factories, one for each of the formulations below, to approximately 1.2×10$^8$ cells. Cells were harvested by incubation for 10 min. at room temperature with 0.25% Trypsin/EDTA. Dissociated cells were transferred to a 500 mL centrifuge tube containing 250 mL of 2% fetal bovine serum (FBS) in Dulbecco's Modified Eagle's Medium (DMEM). Cells were then centrifuged at 1040 RPM in 500 mL tubes in a Sorvall RC3BP centrifuge. Cells were re-suspended in a 0.9% saline/5% dextran 40 solution. The cells were then centrifuged at 1420 RPM for 10 min, and suspended in 10 mL of the following formulations:

Formulation 1: 5% DMSO, 5.5% dextran 40 (Hospira, Lake Forest, Ill.), 10% HSA (control)

Formulation 2: 5% DMSO, 5.5% Dextran 1 (Pharmacosmos), 10% HSA

Formulation 3: 5% DMSO, 5.5% dextran 40 (Pharmacosmos), 10% HSA

Formulation 4: 5% DMSO, 5.5% Dextran 70 (Pharmacosmos), 10% HSA

Filter Retention Assay: Cellular aggregation was assessed through the use of filter retention assay. Cell concentration was adjusted to approximately 1.2×10$^7$ cells/mL prior to filtration. Filter load (number of cells per unit filter area) was held constant at approximately 2.4×10$^8$ cells/filter. Cells were cryopreserved at a concentration of 7.5×10$^6$ cells/ml in a Thermo control rate freezer to −70° C. Cells were thawed prior to use, and samples were processed shortly after thaw. A 100 μL sample of the undiluted cell suspension was taken post thaw, diluted with 900 μL of phosphate buffered saline (PBS), and cell counts were performed in duplicate using a Vi-Cell cell viability analyzer (Beckman Coulter, Fullerton, Calif.).

Results:

Cellular Aggregation

Cellular aggregation within each formulation was assessed using the Filter Retention Assay. Formulation 2 (dextran 1), formulation 3 (dextran 40) and formulation 4 (dextran 70) demonstrated cell aggregation rates equivalent to, or below, control formulation 5% DMSO, 5.5% dextran 40, and 10% HSA (FIG. 13).

Viability and Recovery

The post thaw viability for samples comprising dextran 1, dextran 40 or dextran 70 ranged from 96.0% to 97.7% viable (FIG. 14). Similarly, post thaw recovery was comparable to that of the control formulation, with cell viabilities ranging from 92% to 109% of the control formulation (FIG. 15).

Phenotype and Functionality

The ability to maintain the cells' CD10+, CD34−, CD105+, CD200+ phenotype was tested across the different dextran molecular weights by flow cytometry, and cell immunosuppressive capability was tested in a BTR assay. CD200+/CD105+ expression across all formulations tested ranged from 89.1% to 91.6%, and CD34−/CD10+ expression was >95% for all conditions (FIG. 16). Furthermore, CD4+ and CD8+ T-cell suppression across the different dextran molecular weights fell within 1 standard deviation of an expected value derived from 4 different experimental replicates of a standard control formulation comprising dextran 40 (FIG. 17).

Conclusions:

These results demonstrate that dextran 1 or dextran 70 may be substituted for dextran 40 in the formulations described herein, without impacting cellular aggregation, viability, recovery, phenotype or immunosuppressive capability.

6.3.4 Effect of Different Polysaccharides

The Example describes the effect of polysaccharides other than dextran 40 in the cell formulation on cell viability and proliferation.

Materials and Methods

Twelve million cryopreserved CD 10+, CD34−, CD105+, CD200+ placental multipotent cells were expanded in Nunc™ 10-tray Cell Factories, one for each of the formulations below, to approximately $1.2 \times 10^8$ cells. Cells were harvested by incubation for 10 min. at room temperature with 0.25% Trypsin/EDTA. Dissociated cells were transferred to a 500 mL centrifuge tube containing 250 mL of 2% fetal bovine serum (FBS) in Dulbecco's Modified Eagle's Medium (DMEM). Cells were then centrifuged at 1040 RPM in 500 mL tubes in a Sorvall RC3BP centrifuge. Cells were re-suspended in a 0.9% saline/5% dextran 40 solution. The cells were then centrifuged at 1420 RPM for 10 min, and suspended in 10 mL of the following formulations:

Formulation 1: 5% DMSO, 5.5% dextran 40, 10% HSA (Control)
Formulation 2: 5% DMSO, 5.5% Maltodextrin, 10% HSA
Formulation 3: 5% DMSO, 5.5% Sucrose, 10% HSA
Formulation 4: 5% DMSO, 5.5% Trehalose, 10% HSA
Formulation 5: 5% DMSO, 55 USP/mL Heparin, 10% HSA
Formulation 6: 5% DMSO, 3.3% Hetastarch, 10% HSA
Formulation 7: 5% DMSO, 5.5% Glycogen, 10% HSA Filter Retention Assay: Cellular aggregation was assessed through the use of filter retention assay. Cell concentration was adjusted to approximately $1.2 \times 10^7$ cells/mL prior to filtration. Filter load (number of cells per unit filter area) was held constant at approximately $2.4 \times 10^8$ cells/filter. Cells were cryopreserved in a Thermo control rate freezer to −70° C. Cells were thawed prior to use, and samples were processed shortly after thaw. A 100 μL sample of the undiluted cell suspension was taken post thaw, diluted with 900 μL of phosphate buffered saline (PBS), and cell counts were performed in duplicate using a Vi-Cell cell viability analyzer (Beckman Coulter, Fullerton, Calif.).

Results:

Cellular Aggregation

Cellular aggregation within each formulation was assessed using the Filter Retention Assay. Formulations 2-7 were determined to produce cell aggregation equivalent to, or below, control formulation 5% DMSO, 5.5% dextran 40, and 10% HSA (FIG. 18.). Formulation 4, comprising trehalose, formulation 5, comprising heparin, and formulation 7, comprising glycogen, demonstrated cell aggregation rates substantially below the control formulation.

Post Thaw Viability and Recovery

Post thaw viability, viable cell recovery and cell size data was assessed across each of formulations 1-7 to assess the formulations' cryoprotective capabilities. Post thaw viability was assessed by trypan blue exclusion Vi-Cell cell viability analyzer (Beckman Coulter, Fullerton, Calif.). Post thaw viability ranged from 95.2% to 98.6%, with sucrose and glycogen on the lower end of the range (FIG. 19). The control dextran formulation resulted in cell 98% viability. Post thaw viable cell recovery was calculated to understand cell losses across the freeze/thaw process, values ranged from 84% to 115% across the different polysaccharides (FIG. 20).

Phenotype and Functionality

The ability to maintain the cells' C10+, CD34−, CD105+, CD200+ phenotype was tested across the different polysaccharides by flow cytometry. Cells formulated in formulations 2-4 and 6 maintained this phenotype approximately as well as control formulation 1, and were 89.4% to 92.9% CD105+/CD200+. CD10+/CD34− expression was >95% for each formulation. Of cells frozen in heparin, 85.4% maintained the CD105+/CD200+ phenotype (FIG. 21).

Cell functionality was assessed through the Bead T cell Reaction (BTR) assay, which measures the ability of cells to suppress a T cell response to antigenic beads. Cells formulated in sucrose exhibited decreased T-cell suppression compared to that of the within 1 standard deviation of an expected value derived from 4 different experimental replicates of a standard control formulation comprising dextran 40 (FIG. 22). Across the other polysaccharides, CD4 and CD8 T-cell suppression fell within 1 standard deviation of the expected value.

Conclusions:

With respect to cell aggregation, post-thaw viability, post-thaw cell recovery and maintenance of phenotype, use of formulations comprising maltodextran, trehalose and hetastarch resulted in placental cell populations having approximately the same characteristics as use of the dextran 40 formulation. As such, while formulations comprising sucrose, heparin or glycogen may be used to formulate CD10+, CD34−, CD105+, CD200+ placental stem cells, the use of formulations comprising dextran 40, maltodextran, trehalose or hetastarch is preferred.

6.3.5 Effect of Protein Alternatives of HSA

This Example demonstrates that in a 5.5% dextran 40, 10% HSA and 5% DMSO formulation, the human serum albumin concentration may be reduced, and that the HSA may be substituted with bovine serum albumin or fetal bovine serum.

Formulation 1 (F1) is comprised of 5.5% dextran 40, 10% HSA and 5% DMSO. In order to understand the role of HSA within F1 and understand its impact on cell compositions, alternative formulations with similar proteins similar to human serum albumin, i.e., bovine serum albumin (BSA) and fetal bovine serum (FBS), were tested.

Materials and Methods

Twelve million cryopreserved CD10+, CD34−, CD 105+, CD200+ placental multipotent cells were expanded in Nunc™ 10-tray Cell Factories, one for each of the formulations below, to approximately $1.2 \times 10^8$ cells. Cells were harvested by incubation for 10 minutes at room temperature with 0.25% Trypsin/EDTA. Dissociated cells were transferred to a 500 mL centrifuge tube containing 250 mL of 2% fetal bovine serum (FBS) in Dulbecco's Modified Eagle's Medium (DMEM). Cells were then centrifuged at 1040 RPM in 500 mL tubes in a Sorvall RC3BP centrifuge. Cells were re-suspended in a 0.9% saline/5% dextran 40 solution.

The cells were then centrifuged at 1420 RPM for 10 min, and suspended in 10 mL of the following formulations:

Formulation 1: 5% DMSO, 5.5% dextran 40, 10% HSA (control)
Formulation 2: 5% DMSO, 5.5% dextran 40, 4% HSA
Formulation 3: 5% DMSO, 5.5% dextran 40, 10% BSA
Formulation 4: 5% DMSO, 5.5% dextran 40, 10% FBS Filter Retention Assay: Cellular aggregation was assessed through the use of filter retention assay. Cell concentration was adjusted to approximately $1.2 \times 10^7$ cells/mL prior to filtration. Filter load (number of cells per unit filter area) was held constant at approximately $2.4 \times 10^8$ million cells/filter. Cells were cryopreserved in a Thermo control rate freezer to −70° C. Cells were thawed prior to use, and samples were processed shortly after thaw. A 100 µL sample of the undiluted cell suspension was taken post thaw, diluted with 900 µL of phosphate buffered saline (PBS), and cell counts were performed in duplicate using a Vi-Cell cell viability analyzer (Beckman Coulter, Fullerton, Calif.).

Results:

Cellular Aggregation

Cellular aggregation, as measured by the Filter Retention Assay (FRA), was at or under 100 pixels per square millimeter for all conditions (FIG. 23). However, 10% HSA and 10% BSA appeared to produce discernably fewer aggregates than 4% HSA and 10% FBS.

In order to understand the cryoprotective capability of each solution, post thaw viability, recovery and cell size was assessed through the use of Trypan Blue exclusion on a Vi-Cell cell viability analyzer (Beckman Coulter, Fullerton, Calif.). Post thaw viability across each condition was within assay variability and ranged from 95% to 98% viable (FIG. 24). Similarly, post thaw cell recovery was comparable to that of the 10% HSA control, with values ranging from 100 to 127% (FIG. 25).

Phenotype and Functionality

The ability to maintain the cells' $CD10^+$, $CD34^-$, $CD105^+$, $CD200^+$ phenotype was tested across the different formulations by flow cytometry. (FIGS. 26 and 27). Cells formulated in formulations 2-4 maintained this phenotype approximately as well as the control 10% HSA formulation, with values ranging from 88.2% to 93.5% of tested cells. $CD10^+/CD34^-$ expression was >95% for each formulation.

Cell functionality was measured through the Bead T-cell Reaction assay. Compared to the other conditions suppression of CD4 and CD8 T-cells was elevated when cells were formulated in FBS with values falling within 1.5 standard deviations of the expected value derived from 4 different experimental replicates of a standard control formulation comprising 10% HSA (FIG. 28). Across all other conditions suppression was within I standard deviation of the expected value.

Conclusions:

The results above demonstrate that 4% HSA, 10% BSA, or 10% FBS may be substituted for 10% HSA without appreciable loss of cell viability, cell recovery after thawing, degradation of $CD10^+$, $CD34^-$, $CD105^+$, $CD200^+$ phenotype, or immunosuppressive activity. Thus, a range of at least between about 4% to about 10%, HSA, BSA and/or FBS is particularly suitable for the formulations described herein.

6.3.6 Compatibility with Different Cell Types

The Example demonstrates that bone marrow-derived mesenchymal stem cells and natural killer cells can be formulated in the same manner as placental multipotent cells. Thus, this Example shows that other cells, in addition to placental multipotent cells, can be formulated in the manner presented herein.

Methods and Materials:

Bone marrow-derived mesenchymal stem cells (BMMSCs) and natural killer (NK) cells were expanded and harvested using the following formulations:

F1: Culture of cells for 3 days, followed by collection and resuspension of cells in 5% DMSO, 5.5% dextran 40, 10% HSA, filtration of cells through a 70 µm filter, and cryopreservation of cells at approximately $7.5 \times 10^6$ cells/mL; and F2: Culture of cells for four days, followed by collection and resuspension of cells in Plasmalyte A comprising 5% DMSO and 10% HSA.

Cells were frozen at −70° C. using a controlled rate freezer. BMMSCs were cryopreserved in 20 mL bags in F2 formulation and 10 mL bags in F1 formulation; and $CD3^-$, $CD56^+$ NK cells were cryopreserved in 10 mL bags in F2 formulation and in 1.5 mL vials in F1 formulation. These samples were later thawed and analyzed to determine the effects of freezing formulation on cellular characteristics.

Filter Retention Assay: Cellular aggregation was assessed through the use of filter retention assay. Cell concentration was adjusted to approximately $1.2 \times 10^7$ cells/mL prior to filtration. Filter load (number of cells per unit filter area) was held constant at approximately $2.4 \times 10^8$ million cells/filter. Cells were cryopreserved in a Thermo control rate freezer to −70° C. Cells were thawed prior to use, and samples were processed shortly after thaw. A 100 µL sample of the undiluted cell suspension was taken post thaw, diluted with 900 µL of phosphate buffered saline (PBS), and cell counts were performed in duplicate using a Vi-Cell cell viability analyzer (Beckman Coulter, Fullerton, Calif.).

Results

Viability

Post-thaw samples were used to determine the viability of the cells frozen under different conditions. Viability of BMMSCs and NK cells was not significantly affected by the freezing conditions.

Phenotype

NK markers were assayed to determine the effects of F1 and F2 formulations on the NK phenotype ($CD3^-$, $CD56^+$). The two formulations used did not significantly affect the percentage of NK cells displaying the NK phenotype. BMMSC were also analyzed for the expression of CD10, CD34, CD44, CD45, CD90, CD98, CD105, CD117, CD166, CD200, Pan-cytokeratin, and KDR. The expression, or lack of expression, of these markers did not vary significantly in BMMSC formulated in F1 or F2 formulations.

Cellular Aggregation

In the Filter Retention Assay, two replicates of each of the BMMSC formulations, and one assay replicate of the NK formulations, were performed. The F1 formulation produced significantly fewer aggregates than the F2 formulation for both BMMSCs and NK cells; the effect of formulation F2, however, was more pronounced for BMMSCs than for NK cells (FIG. 29).

Conclusions:

The results above demonstrate that bone marrow-derived mesenchymal stem cells and natural killer cells can successfully be formulated in 5% DMSO, 5.5% dextran 40, 10% HSA, with cellular aggregation, viability and phenotype retention similar to that of $CD10^+$, $CD34^-$, $CD105^+$, $CD200^+$ placental multipotent cells in the same formulation. In addition, for the placental multipotent cells, Plasmalyte-containing formulations of BMMSCs and NK cells show significantly higher rates of cellular aggregation; as such, dextran-containing formulations are preferred.

Equivalents:

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method of making a composition comprising homogenous isolated human adherent placental cells that have been passaged in vitro at least two times, comprising:
    (a) contacting said cells with a first solution comprising dextran and human serum albumin (HSA) to form a cell-containing solution;
    (b) filtering out macro cell clumps from the cell-containing solution;
    (c) diluting said cells to no more than about $10\pm3\times10^6$ cells per milliliter with a second solution comprising dextran, dimethylsulfoxide (DMSO), and HSA; and
    (d) cryopreserving said cells after step (c), thereby making a composition comprising isolated human adherent placental cells.

2. The method of claim 1, wherein said dextran is dextran 40.

3. The method of claim 1, wherein said second solution comprises about 5.5% dextran 40.

4. The method of claim 1, wherein said second solution comprises about 10% HSA.

5. The method of claim 1, wherein said second solution comprises about 2.5% DMSO.

6. The method of claim 1, wherein said second solution comprises about 7.5% to about 9% dextran.

7. The method of claim 1, wherein said composition comprising cells comprises about $1.0\pm0.3\times10^6$ cells per milliliter to about $5.0\pm1.5\times10^6$ cells per milliliter.

8. A method of making a composition comprising cells, comprising:
    (a) suspending a plurality of homogenous isolated human adherent placental cells, which have been passaged in vitro at least two times, in a 5.5% dextran 40, 10% HSA solution to form a cell-containing solution;
    (b) filtering the cell-containing solution through a 70 μM filter to filter out macro cell clumps from the cell-containing solution;
    (c) diluting the cell-containing solution in 5.5% dextran 40, 10% HSA, and 5% DMSO to no more than about $10\pm3\times10^6$ cells/mL;
    (d) cryopreserving the cells; and
    (e) thawing the cells
to produce said composition comprising cells.

9. A method of making a composition comprising cells, comprising:
    (a) centrifuging a plurality of homogenous isolated human adherent placental cells, which have been passaged in vitro at least two times, to collect the cells;
    (b) resuspending the cells in 5.5% dextran 40;
    (c) centrifuging the cells to collect the cells;
    (d) resuspending the cells in a 5.5% dextran 40 solution that comprises 10% HSA to form a cell-containing solution;
    (e) filtering the cell-containing solution through a 70 μM to 100 μM filter to filter out macro cell clumps from the cell-containing solution;
    (f) diluting the cell-containing solution in 5.5% dextran 40, 10% HSA, and 5% DMSO to no more than about $10\pm3\times10^6$ cells/mL;
    (g) cryopreserving the cells; and
    (h) thawing the cells
to produce said composition comprising cells.

10. A method of making a composition comprising homogenous isolated human adherent placental cells, comprising:
    (a) providing a plurality of homogenous isolated human adherent placental cells, which have been passaged in vitro at least two times, in a solution comprising 5.5% dextran 40 and 10% HSA to form a solution comprising isolated human adherent placental cells;
    (b) filtering said solution comprising homogenous isolated human adherent placental cells to filter out macro cell clumps from the cell-containing solution to produce filtered isolated human adherent placental cells;
    (c) diluting said filtered isolated human adherent placental cells with an amount of a solution comprising 5.5% dextran 40, 10% HSA and 5% dimethylsulfoxide (DMSO) sufficient to bring said filtered isolated human adherent placental cells to about $10\pm3\times10^6$ cells per milliliter;
    (d) diluting said isolated human adherent placental cells with 10% dextran 40 at a ratio of about 1:1 to about 1:11 isolated human adherent placental cells:dextran 40 to produce said composition;
    (e) cryopreserving the cells.

11. The method of claim 1, wherein said filter is a 70 μM filter.

12. The method of claim 1, wherein said filter is a 100 μM filter.

13. The method of claim 1, wherein said isolated human adherent placental cells are $CD10^+$, $CD34^-$ and $CD105^+$.

14. The method of claim 13, wherein said $CD10^+$, $CD34^-$ and $CD105^+$ cells are $CD200^+$.

15. The method of claim 14, wherein said $CD10^+$, $CD34^-$, $CD105^+$ and $CD200^+$ cells are either $CD45^-$ or $CD90^+$.

16. The method of claim 14, wherein said $CD10^+$, $CD34^-$, $CD105^+$ and $CD200^+$ cells are $CD45^-$ and $CD90+$.

17. The method of claim 1, further comprising concentrating the composition comprising cells to about $5\times10^6$ cells per milliliter to $1\times10^8$ cells per milliliter.

18. The method of claim 17, further comprising subcutaneously administering the composition comprising cells to a subject.

19. The method of claim 8, further comprising diluting the composition comprising cells after step (e) 1:1 to 1:11 with 10% dextran 40.

20. The method of claim 9, further comprising diluting the composition comprising cells after step (h) 1:1 to 1:11 with 10% dextran 40.

21. The method of claim 1, wherein said filter is a 70 μM to 100 μM filter.

22. The method of claim 1, wherein said second solution comprises 5.0% dextran, 10% HSA, and 2.5% DMSO.

* * * * *